United States Patent
Farokhzad et al.

(10) Patent No.: US 11,123,304 B2
(45) Date of Patent: Sep. 21, 2021

(54) NANOPARTICLES HAVING POLY(ESTER AMIDE) POLYMER CORES AS DRUG DELIVERY VEHICLES

(71) Applicant: The Brigham and Women's Hospital, Inc., Boston, MA (US)

(72) Inventors: Omid C. Farokhzad, Waban, MA (US); Jun Wu, Boston, MA (US); Xi Zhu, Qingdao (CN); Jinjun Shi, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 16/483,170

(22) PCT Filed: Feb. 3, 2017

(86) PCT No.: PCT/US2017/016577
§ 371 (c)(1),
(2) Date: Aug. 2, 2019

(87) PCT Pub. No.: WO2018/144022
PCT Pub. Date: Aug. 9, 2018

(65) Prior Publication Data
US 2019/0350870 A1   Nov. 21, 2019

(51) Int. Cl.
*A61K 9/51*   (2006.01)
*A61P 3/10*   (2006.01)
(Continued)

(52) U.S. Cl.
CPC .......... *A61K 9/5153* (2013.01); *A61K 9/5192* (2013.01); *A61K 31/337* (2013.01);
(Continued)

(58) Field of Classification Search
CPC .. A61K 9/5153; A61K 9/5192; A61K 31/337; A61K 38/28; A61K 39/35;
(Continued)

(56) References Cited

U.S. PATENT DOCUMENTS

| | | | |
|---|---|---|---|
| 8,765,162 B2 | 7/2014 | Ngo et al. | |
| 2002/0176841 A1 | 11/2002 | Barker et al. | |

(Continued)

FOREIGN PATENT DOCUMENTS

| | | |
|---|---|---|
| CN | 109789103 | 5/2019 |
| EP | 3490538 | 6/2019 |

(Continued)

OTHER PUBLICATIONS

U.S. Appl. No. 15/510,597, Farokhzad, et al., filed Sep. 11, 2015.
(Continued)

*Primary Examiner* — Carlos A Azpuru
(74) *Attorney, Agent, or Firm* — Fish & Richardson P.C.

(57) ABSTRACT

This disclosure relates to nanoparticles comprising a core comprising a poly(ester amide) polymer comprising a repeating unit of Formula (Ia):

(Continued)

and a repeating unit of Formula (Ib):

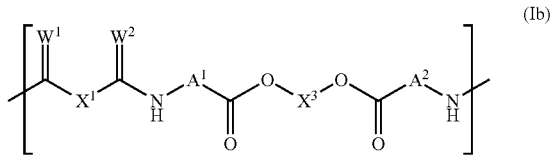

wherein $W^1$, $W^2$, $X^1$, $A^1$, $X^2$, $A^2$, and $X^3$ are as described herein, a payload molecule within the core, and a surface layer comprising a targeting ligand that binds or reacts selectively with a receptor on the outside surface of a cell. Methods of making such nanoparticles, and methods of using such nanoparticles as drug delivery vehicles, are also provided.

10 Claims, 33 Drawing Sheets

Specification includes a Sequence Listing.

(51) Int. Cl.
 *A61K 31/337* (2006.01)
 *A61K 38/28* (2006.01)
 *A61K 39/35* (2006.01)
 *A61K 39/00* (2006.01)

(52) U.S. Cl.
 CPC .............. *A61K 38/28* (2013.01); *A61K 39/35* (2013.01); *A61P 3/10* (2018.01); *A61K 2039/55516* (2013.01); *A61K 2039/55544* (2013.01); *A61K 2039/55561* (2013.01); *A61K 2039/55572* (2013.01)

(58) Field of Classification Search
 CPC .......... A61K 2039/55516; A61K 2039/55544; A61K 2039/55561; A61K 2039/55572; A61K 31/4745; A61K 9/0019; A61K 9/0053; A61K 9/5146; A61K 31/573; A61K 38/00; A61P 3/10
 See application file for complete search history.

(56) References Cited

U.S. PATENT DOCUMENTS

| | | | |
|---|---|---|---|
| 2010/0210465 A1 | 8/2010 | Li et al. | |
| 2011/0065807 A1 | 3/2011 | Radovic-Moreno et al. | |
| 2012/0135054 A1 | 5/2012 | Chu et al. | |
| 2016/0338970 A1* | 11/2016 | Farokhzad | ........... A61K 9/5153 |

FOREIGN PATENT DOCUMENTS

| | | |
|---|---|---|
| JP | 2019523285 | 8/2019 |
| KR | 20190034307 | 4/2019 |
| WO | WO2016040814 | 3/2016 |
| WO | WO2016061201 | 4/2016 |
| WO | WO2016065306 | 4/2016 |
| WO | WO2018026833 | 2/2018 |
| WO | WO2018144022 | 8/2018 |

OTHER PUBLICATIONS

U.S. Appl. No. 15/519,052, Farokhzad, et al., filed Oct. 14, 2015.
U.S. Appl. No. 15/520,796, Shi, et al., filed Oct. 23, 2015.
U.S. Appl. No. 16/322,669, Loscalzo, et al., filed Feb. 1, 2019.
U.S. Appl. No. 62/049,117, Farokhzad, et al., filed Sep. 11, 2014.
U.S. Appl. No. 62/063,601, Farokhzad, et al., filed Oct. 14, 2014.
U.S. Appl. No. 62/067,744, Shi, et al., filed Oct. 23, 2014.
U.S. Appl. No. 62/182,178, Farokhzad, et al., filed Jun. 19, 2015.
U.S. Appl. No. 62/369,412, Loscalzo, et al., filed Aug. 1, 2016.
U.S. Appl. No. 62/371,306, Loscalzo, et al., filed Aug. 5, 2016.
U.S. Appl. No. 62/374,639, Loscalzo, et al., filed Aug. 12, 2016.
Aguado et al., "Controlled-release vaccines-biodegradable polylactide/polyglycolide (PL/PG) microspheres as antigen vehicles," Immunobiology, Feb. 1, 1992, 184(2-3):113-25.
Akagi et al., "Biodegradable nanoparticles as vaccine adjuvants and delivery systems: regulation of immune responses by nanoparticle-based vaccine," Polymers in Nanomedicine, Springer, Berlin, Heidelberg, 2011, 31-64.
Akagi et al., "Stabilization of polyion complex nanoparticles composed of poly (amino acid) using hydrophobic interactions," Langmuir, Dec. 17, 2009, 26(4):2406-13.
Arora et al., "Characterisation of streptozotocin induced diabetes mellitus in swiss albino mice," Global Journal of Pharmacology, 2009, 3(2):81-4.
Bonifaz et al., "Efficient targeting of protein antigen to the dendritic cell receptor DEC-205 in the steady state leads to antigen presentation on major histocompatibility complex class I products and peripheral CD8+ T cell tolerance," Journal of Experimental Medicine, Dec. 16, 2002, 196(12):1627-38.
Bonifaz et al., "In vivo targeting of antigens to maturing dendritic cells via the DEC-205 receptor improves T cell vaccination," Journal of Experimental Medicine, Mar. 15, 2004, 199(6):815-24.
Bramwell et al., "Particulate delivery systems for biodefense subunit vaccines," Advanced Drug Delivery Reviews, Jun. 17, 2005, 57(9):1247-65.
Chan et al., "Polymeric nanoparticles for drug delivery," Cancer Nanotechnology, Humana Press, 2010, 163-75.
Duchardt et al., "A comprehensive model for the cellular uptake of cationic cell-penetrating peptides," Traffic, Jul. 2007, (7):848-66.
Dutta et al., "Search for inhibitors of endocytosis: Intended specificity and unintended consequences," Cellular Logistics, Oct. 1, 2012, 2(4):203-8.
Farokhzad et al., "Targeted nanoparticle-aptamer bioconjugates for cancer chemotherapy in vivo," Proceedings of the National Academy of Sciences, Apr. 18, 2006, 103(16):6315-20.
Friedman et al., "The smart targeting of nanoparticles," Current Pharmaceutical Design, Oct. 1, 2013, 19(35):6315-29.
Frokjaer et al., "Protein drug stability: a formulation challenge," Nature Reviews Drug Discovery, Apr. 2005, 4(4):298-306.
Gu et al., "Precise engineering of targeted nanoparticles by using self-assembled biointegrated block copolymers," Proceedings of the National Academy of Sciences, Feb. 19, 2008, 105(7):2586-91.
Hawiger et al., "Dendritic cells induce peripheral T cell unresponsiveness under steady state conditions in vivo," Journal of Experimental Medicine, Sep. 17, 2001, 194(6):769-80.
Jiang et al., "Biodegradable poly (lactic-co-glycolic acid) microparlicles for injectable delivery of vaccine antigens," Advanced Drug Delivery Reviews, Jan. 10, 2005, 57(3):391-410.
Kamaly et al., "Development and in vivo efficacy of targeted polymeric inflammation-resolving nanoparticles," Proceedings of the National Academy of Sciences, Apr. 16, 2013, 110(16):6506-11.
Kamaly et al., "Targeted polymeric therapeutic nanoparticles: design, development and clinical translation," Chemical Society Reviews, 2012, 41(7):2971-3010.
Katsarava et al., "Amino acid-based bioanalogous polymers. Synthesis, and study of regular poly (ester amide) s based on bis (α-amino acid) α, ω-alkylene diesters, and aliphatic dicarboxylic acids," Journal of Polymer Science Part A: Polymer Chemistry, Feb. 15, 1999, 37(4):391-407.
Kawabata et al., "Molecular cloning of transferrin receptor 2 A new member of the transferrin receptor-like family," Journal of Biological Chemistry, Jul. 23, 1999, 274(30):20826-32.
Krieg, "Antiinfective applications of toll-like receptor 9 agonists," Proceedings of the American Thoracic Society, Jul. 2007, 4(3):289-94.
Leader et al., "Protein therapeutics: a summary and pharmacological classification," Nature Reviews Drug Discovery, Jan. 2008, 7(1):21-39.

(56) References Cited

OTHER PUBLICATIONS

Makadia et al., "Poly lactic-co-glycolic acid (PLGA) as biodegradable controlled drug delivery carrier," Polymers, Sep. 2011, 3(3):1377-97.

McMahon et al., "Molecular mechanism and physiological functions of clathrin-mediated endocytosis," Nature Reviews Molecular Cell Biology, Aug. 2011, 12(8):517.

Mellman et al., "Antigen processing and presentation by dendritic cells: cell biological mechanisms," Mechanisms of Lymphocyte Activation and Immune Regulation X, Springer, Boston, MA, 2005, 63-67.

Mellman et al., "Dendritic cells: specialized and regulated antigen processing machines," Cell, Aug. 10, 2001, 106(3):255-8.

Mo et al., "Emerging micro- and nanotechnology based synthetic approaches for insulin delivery," Chemical Society Reviews, 2014, 43(10):3595-629.

PCT International Preliminary Report on Patentability in International Appln. PCT/US17/16577, dated May 11, 2017, 8 Pages.

PCT International Search Report and Written Opinion in International Appln. PCT/US17/16577, dated May 11, 2017, 14 Pages.

Pridgen et al., "Polymeric nanoparticle technologies for oral drug delivery," Clinical Gastroenterology and Hepatology, Oct. 1, 2014, 12(10):1605-10.

Pridgen et al., "Transepithelial transport of Fc-targeted nanoparticles by the neonatal fc receptor for oral delivery," Science Translational Medicine, 2013, 5.213(2013): 213ra167, 19 Pages.

Samstein et al., "The use of deoxycholic acid to enhance the oral bioavailability of biodegradable nanoparticles," Biomaterials, Feb. 1, 2008, 29(6):703-8.

Schmidt, "Clinical setbacks for toll-like receptor 9 agonists in cancer," Nature Biotechnology, Aug. 2, 2007, 25(8):825-6.

Stewart, "Dust mite allergens," Clinical 13(2):135-50 Reviews in Allergy and Immunology, Jun. 1, 1995, 13(2):135-50.

Summerton, "Endo-Porter: a novel reagent for safe, effective delivery of substances into cells," Annals—New York Academy of Sciences, Nov. 1, 2005, 1058:62, 11 pages.

Vermonden et al., "Hydrogels for protein delivery," Chemical Reviews, Feb. 23, 2012, 112(5):2853-88.

Wiley et al., "Transcytosis and brain uptake of transferrin-containing nanoparticles by tuning avidity to transferrin receptor," Proceedings of the National Academy of Sciences, May 21, 2013, 110(21):8662-7.

Wu et al., "Development of multinuclear polymeric nanoparticles as robust protein nanocarriers," Angewandte Chemie International Edition, Aug. 18, 2014, 53(34):8975-9.

Wu et al., "Synthesis and characterization of ionic charged water soluble arginine-based poly (ester amide)," Journal of Materials Science: Materials in Medicine, Mar. 1, 2011, 22(3):469-79.

Wu et al., "Water insoluble cationic poly (ester amide) s: synthesis, characterization and applications," Journal of Materials Chemistry B., 2013, 1(3):353-60.

Yameen et al., "Drug Delivery Nanocarriers from a Fully Degradable PEG-Conjugated Polyester with a Reduction-Responsive Backbone," Chemistry—A European Journal, Aug. 3, 2015, 21(32):11325-9.

Yu et al., "Microneedle-array patches loaded with hypoxia-sensitive vesicles provide fast glucose-responsive insulin delivery," Proceedings of the National Academy of Sciences, Jul. 7, 2015, 112(27):8260, 11 pages.

Zhang et al., "Mechanism study of cellular uptake and tight junction opening mediated by goblet cell-specific trimethyl chitosan nanoparticles," Molecular Pharmaceutics, Apr. 11, 2014, 11(5):1520-32.

Zhu et al., "Polymeric nanoparticles amenable to simultaneous installation of exterior targeting and interior therapeutic proteins," Angewandte Chemie International Edition, Mar. 1, 2016, 55(10):3309-12.

Zhu et al., "Transport across a polarized monolayer of Caco-2 cells by transferrin receptor-mediated adenovirus transcytosis," Virology, Jul. 20, 2004, 325(1):116-28.

\* cited by examiner

NANOPARTICLES HAVING POLY(ESTER AMIDE) POLYMER CORES AS DRUG DELIVERY VEHICLES

STATEMENT AS TO FEDERALLY SPONSORED RESEARCH

This invention was made with Government support under Grant Nos. EB015419, R00CA160350, and CA151884, awarded by National Institutes of Health (NIH). The Government has certain rights in the invention.

CLAIM OF PRIORITY

This application is a § 371 National Stage Application of PCT/US2017/016577, filed Feb. 3, 2017. The entire contents of the foregoing are incorporated herein by reference.

TECHNICAL FIELD

This invention relates to particles, compositions, methods of making, and methods of use thereof.

BACKGROUND

Protein-based therapies are important in the treatment of diseases. Thus, there is a need to develop improved methods for the delivery of biomolecules such as proteins to patients via, e.g., the pulmonary, nasal, subcutaneous, and oral routes.

Numerous nanoparticle (NP) platforms have been developed for the delivery of proteins. However, the capability of existing NPs for protein delivery applications remains limited, e.g., due to low loading efficiency and uncontrollable release profiles.

The clinical translation of protein drugs and protein-delivering nanomedicines has been hindered due to difficulties in the development and manufacturing of protein-based therapeutics that must be overcome to achieve clinical translation. Limitations such as synthetic chemical coupling and formulation parameters such as homogenization, sonication, extrusion, and exposure to solvents often lead to the inactivation of biomolecules. Safe and effective delivery of protein therapeutics to desired disease tissues remains a significant challenge.

Accordingly, there is a need for particles, formulations and compositions for safe and efficacious delivery of therapeutic proteins to target cells. The present application provides particles, formulations and compositions for safe and efficacious delivery of therapeutic proteins to target cells, in addition to methods of making and using these particles, formulations and compositions.

SUMMARY

A protein delivery NP platform should possess at least some of the following characteristics: effective protein loading and protection; sustainable protein release; and a simple formulation strategy that preserves the bioactivity of proteins. Moreover, NPs for oral delivery should overcome the transport barrier of the intestinal epithelium. The present disclosure describes a NP particle that has some or all of these features.

In some aspects, the present disclosure provides a particle that includes a core comprising a polymer that comprises a positively charged component and a hydrophobic component; and a payload molecule within the core. The particle can include a surface layer comprising a targeting ligand that binds or reacts selectively with a receptor on the outside surface of a cell.

In some aspects, the positively charged component comprises an aminoacid residue.

In some aspects, the hydrophobic component comprises an aminoacid residue.

In some aspects, the positively charged component and the hydrophobic component each comprise an aminoacid residue.

In some aspects, the polymer further comprises a hydrocarbon linker between the positively charged component and the hydrophobic component.

In some aspects, the hydrocarbon linker comprises 3-100 carbon atoms.

In some aspects, the hydrocarbon linker comprises 4-10 carbon atoms.

In some aspects, the polymer that comprises a positively charged component and a hydrophobic component is a poly(ester amide) polymer comprising a repeating unit of Formula (Ia):

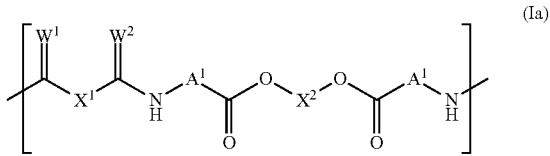

and a repeating unit of Formula (Ib):

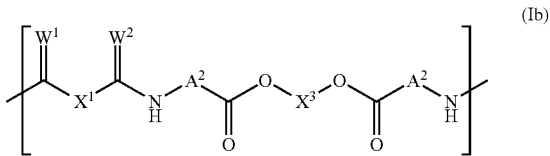

wherein:

each $X^1$ is $C_{1-100}$ alkylene, $C_{2-100}$ alkenylene, or $C_{2-100}$ alkynylene, each of which is optionally substituted with 1, 2, or 3 substituents independently selected from the group consisting of: halo, —CN, $R^1$, $OR^1$, $NR^1R^2$, —(C=O)$R^2$, —(C=O)O$R^2$, —(C=O)N$R^1R^2$, and —S(O)$_m R^2$;

$X^2$ is $C_{1-100}$ alkylene, $C_{2-100}$ alkenylene, or $C_{2-100}$ alkynylene, each of which is optionally substituted with 1, 2, or 3 substituents independently selected from the group consisting of: halo, —CN, $R^1$, $OR^1$, $NR^1R^2$, —(C=O)$R^2$, —(C=O)O$R^2$, —(C=O)N$R^1R^2$, and —S(O)$_m R^2$;

$X^3$ is $C_{1-100}$ alkylene, $C_{2-100}$ alkenylene, or $C_{2-100}$ alkynylene, each of which is optionally substituted with 1, 2, or 3 substituents independently selected from the group consisting of: halo, —CN, $R^1$, $OR^1$, $NR^1R^2$, —(C=O)$R^2$, —(C=O)O$R^2$, —(C=O)N$R^1R^2$, and —S(O)$_m R^2$;

each $R^1$ is H, $C_{1-6}$ alkyl, $C_{2-6}$ alkenyl, $C_{2-6}$ alkynyl, $C_{3-10}$ cycloalkyl, $C_{6-10}$ aryl, 5-10-membered heteroaryl, or 4-10-membered heterocycloalkyl, each of which is optionally substituted with 1, 2, or 3 substituents independently selected from the group consisting of OH, $NO_2$, CN, halo, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thiol, $C_{1-6}$ alkylthio, $C_{1-6}$ alkylsulfinyl, $C_{1-6}$ alkylsulfonyl, carboxy, $C_{1-6}$ alkylcarbonyl, and $C_{1-6}$ alkoxycarbonyl;

each $R^2$ is H, $C_{1-6}$ alkyl, $C_{2-6}$ alkenyl, $C_{2-6}$ alkynyl, $C_{3-10}$ cycloalkyl, $C_{6-10}$ aryl, 5-10-membered heteroaryl, or 4-10-membered heterocycloalkyl, each of which is optionally substituted with 1, 2, or 3 substituents independently selected from the group consisting of OH, $NO_2$, CN, halo, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thiol, $C_{1-6}$ alkylthio, $C_{1-6}$ alkylsulfinyl, $C_{1-6}$ alkylsulfonyl, carboxy, $C_{1-6}$ alkylcarbonyl, and $C_{1-6}$ alkoxycarbonyl;

each m is 0, 1 or 2;
each $W^1$ is O, S, or NH;
each $W^2$ is O, S, or NH;
each $A^1$ is a hydrophobic aminoacid residue; and
each $A^2$ is a cationic aminoacid residue.

In some aspects, the repeating unit of Formula (Ia) has Formula (IIa):

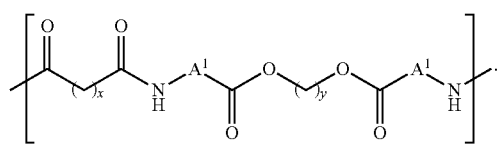

In some aspects, the repeating unit of Formula (Ib) has Formula (IIb):

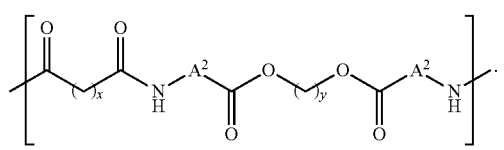

In some aspects, x is an integer from 1 to 12.
In some aspects, y is an integer from 1 to 10.
In some aspects, x is an integer from 2 to 10 and y is an integer from 2 to 8.
In some aspects, each $A^1$ is a residue of natural aminoacid.
In some aspects, each $A^1$ is a residue of unnatural aminoacid.
In some aspects, one $A^1$ group is a residue of natural aminoacid and the other $A^1$ group is a residue of unnatural aminoacid.
In some aspects, $A^2$ is a residue of natural aminoacid.
In some aspects, $A^2$ is a residue of unnatural aminoacid.
In some aspects, one $A^2$ group is a residue of natural aminoacid and the other $A^2$ group is a residue of unnatural aminoacid.
In some aspects, $A^1$ is selected from the group of the following Formulae:

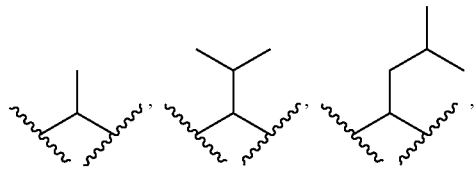

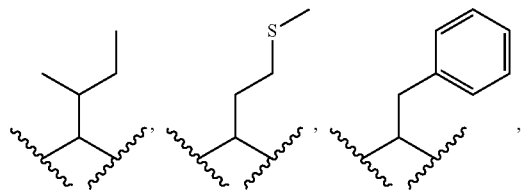

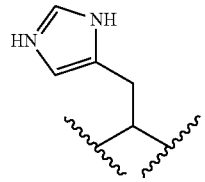

In some aspects, $A^2$ is selected from the group of the following Formulae:

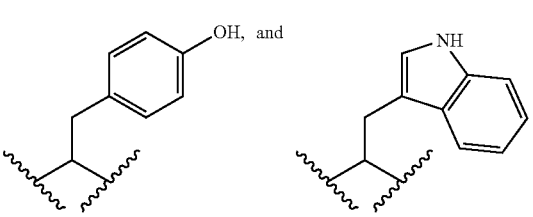

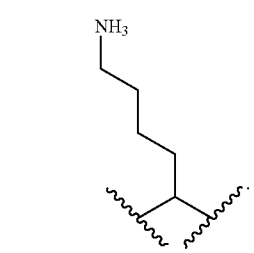

In some aspects, $A^2$ is selected from the group of the following Formulae:

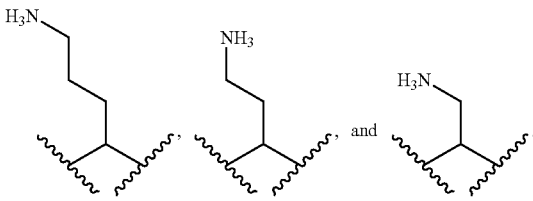

In some aspects, the repeating unit of Formula (Ia) has Formula (IIIa) of Formula (IIId):

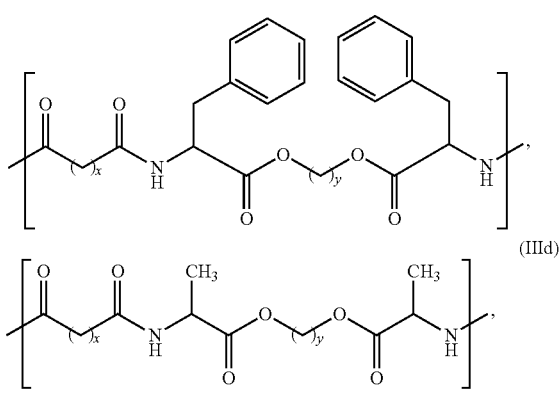

wherein x is 4, 6 or 8 and y is 6.

In some aspects, the repeating unit of Formula (Ib) has Formula (IIIb):

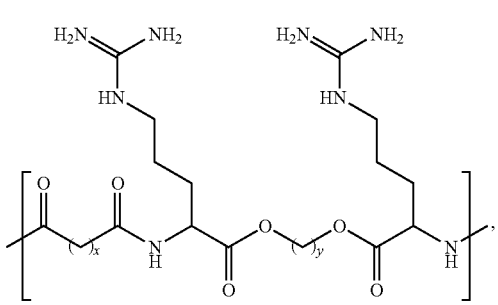

wherein x is 4, 6 or 8 and y is 6.

In some aspects, the polymer that comprises a positively charged component and a hydrophobic component is a poly(ester amide) polymer comprising a repeating unit of Formula (Ic):

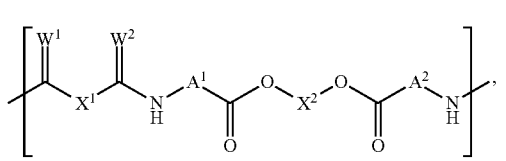

wherein:

each $X^1$ is $C_{1-100}$ alkylene, $C_{2-100}$ alkenylene, or $C_{2-100}$ alkynylene, each of which is optionally substituted with 1, 2, or 3 substituents independently selected from the group consisting of: halo, —CN, $R^1$, $OR^1$, $NR^1R^2$, —(C=O)$R^2$, —(C=O)$OR^2$, —(C=O)$NR^1R^2$, and —S(O)$_m$$R^2$;

$X^2$ is $C_{1-100}$ alkylene, $C_{2-100}$ alkenylene, or $C_{2-100}$ alkynylene, each of which is optionally substituted with 1, 2, or 3 substituents independently selected from the group consisting of: halo, —CN, $R^1$, $OR^1$, $NR^1R^2$, —(C=O)$R^2$, —(C=O)$OR^2$, —(C=O)$NR^1R^2$, and —S(O)$_m$$R^2$;

each $R^1$ is H, $C_{1-6}$ alkyl, $C_{2-6}$ alkenyl, $C_{2-6}$ alkynyl, $C_{3-10}$ cycloalkyl, $C_{6-10}$ aryl, 5-10-membered heteroaryl, or 4-10-membered heterocycloalkyl, each of which is optionally substituted with 1, 2, or 3 substituents independently selected from the group consisting of OH, $NO_2$, CN, halo, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thiol, $C_{1-6}$ alkylthio, $C_{1-6}$ alkylsulfinyl, $C_{1-6}$ alkylsulfonyl, carboxy, $C_{1-6}$ alkylcarbonyl, and $C_{1-6}$ alkoxycarbonyl;

each $R^2$ is H, $C_{1-6}$ alkyl, $C_{2-6}$ alkenyl, $C_{2-6}$ alkynyl, $C_{3-10}$ cycloalkyl, $C_{6-10}$ aryl, 5-10-membered heteroaryl, or 4-10-membered heterocycloalkyl, each of which is optionally substituted with 1, 2, or 3 substituents independently selected from the group consisting of OH, $NO_2$, CN, halo, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thiol, $C_{1-6}$ alkylthio, $C_{1-6}$ alkylsulfinyl, $C_{1-6}$ alkylsulfonyl, carboxy, $C_{1-6}$ alkylcarbonyl, and $C_{1-6}$ alkoxycarbonyl;

each m is 0, 1 or 2;

each $W^1$ is O, S, or NH;

each $W^2$ is O, S, or NH;

each $A^1$ is a hydrophobic aminoacid residue; and each $A^2$ is a cationic aminoacid residue.

In some aspects, the repeating unit of Formula (Ic) has Formula (IIc)

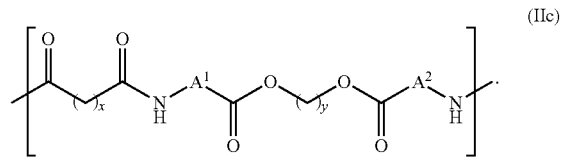

In some aspects, x is an integer from 1 to 12.

In some aspects, y is an integer from 1 to 10.

In some aspects, x is an integer from 2 to 10 and y is an integer from 2 to 8.

In some aspects, each $A^1$ is a residue of natural aminoacid.

In some aspects, each $A^1$ is a residue of unnatural aminoacid.

In some aspects, $A^2$ is a residue of natural aminoacid.

In some aspects, $A^2$ is a residue of unnatural aminoacid.

In some aspects, $A^1$ is selected from the group of the following Formulae:

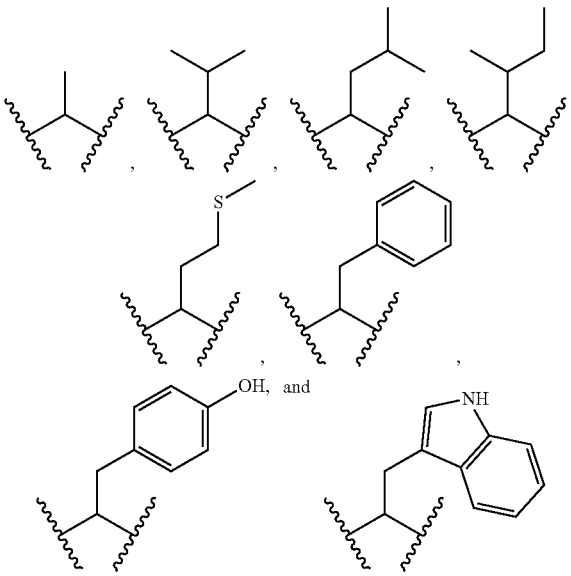

In some aspects, $A^2$ is selected from the group of the following Formulae:

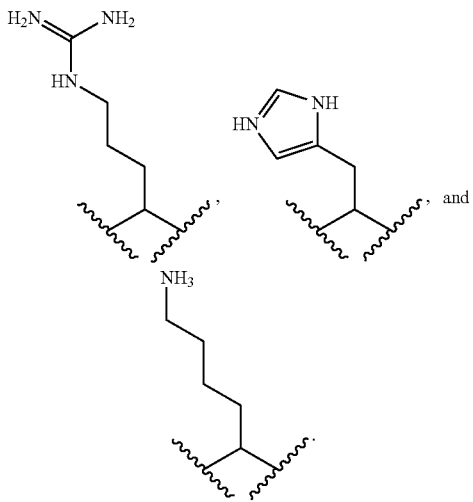

In some aspects, $A^2$ is selected from the group of the following Formulae:

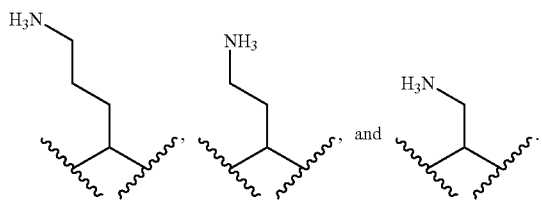 [SMILES: *C(*)CCCN ; *C(*)CCN ; *C(*)CN]

In some aspects, the repeating unit of Formula (Ic) has Formula (IIIc) or Formula (IIIe):

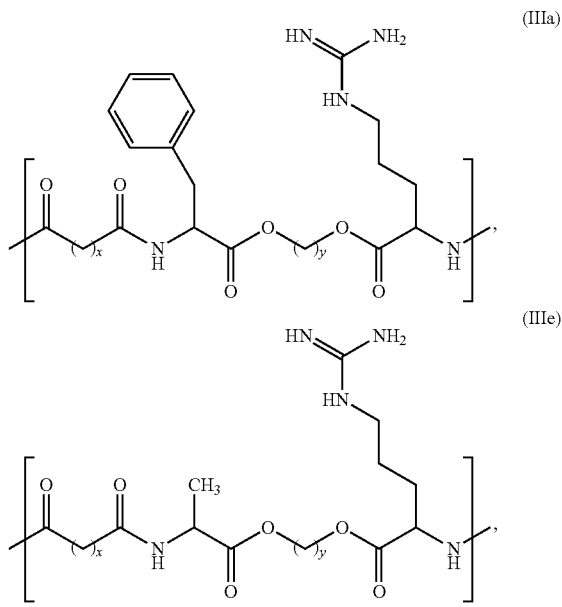

wherein x is 4, 6 or 8 and y is 6.

In some aspects, the payload molecule is a therapeutic protein.

In some aspects, the therapeutic protein is insulin.

In some aspects, the payload molecule is a chemotherapeutic agent.

In some aspects, the chemotherapeutic agent is docetaxel.

In some aspects, the payload molecule is an antigen.

In some aspects, the antigen is a dust mite allergen.

In some aspects, the core comprises a second payload molecule and the second payload molecule is an adjuvant.

In some aspects, the adjuvant is selected from resiquimod, imiquimod, gardiquimod, flagellin, monophosphoryl lipid A, N-glycolyted muramyldipeptide, CpG and cholera toxin.

In some aspects, the targeting ligand that binds or reacts selectively with a receptor on the outside surface of a cell further promotes transcytosis or endocytosis of the particle.

In some aspects, the targeting ligand is transferrin.

In some aspects, the present disclosure provides a method of preparing a particle as described herein, the method comprising:

obtaining a first solution of the polymer that comprises a positively charged component and a hydrophobic component in a water-miscible solvent;

obtaining a second aqueous solution comprising the targeting ligand that binds or reacts selectively with a receptor on the outside surface of a cell; and mixing the first solution with the second aqueous solution to form an aqueous suspension comprising a particle as described herein.

In some aspects, the water-miscible solvent is dimethyl sulfoxide (DMSO).

In some aspects, the first solution comprises a payload molecule.

In some aspects, the payload molecule is a therapeutic protein.

In some aspects, the therapeutic protein is insulin.

In some aspects, the payload molecule is an antigen.

In some aspects, the antigen is dust mite allergen.

In some aspects, the mixing is carried out at room temperature.

In some aspects, the present disclosure provides a composition comprising the particle as described herein and a pharmaceutically acceptable carrier.

In some aspects, the present disclosure provides a method of treating a disease or condition in a subject in need thereof, the method comprising administering to the subject a therapeutically effective amount of the particle described here or the composition as described herein.

In some aspects, the disease or condition is diabetes.

In some aspects, the disease or condition is cancer.

In some aspects, the present disclosure provides a method of inducing an immune response in a subject in need thereof, the method comprising administering to the subject an effective amount of the particle as described herein or the composition as described herein.

In some aspects, the present disclosure provides a method of vaccinating a subject in need thereof, the method comprising administering to the subject an effective amount of the particle as described herein or the composition as described herein (wherein, e.g., the particle or a composition comprises an antigen and optionally an adjuvant).

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features, objects, and advantages of the invention will be apparent from the description and drawings, and from the claims.

DETAILED DESCRIPTION

Effective delivery of therapeutic molecules such as proteins is a formidable challenge. Provided herein, using a unique polymer family that can be tuned to possess a wide-ranging set of cationic and/or hydrophobic features, and a novel nanoparticle (NP) platform capable of installing targeting ligands (e.g., protein ligands) on the particle surface and simultaneously carrying a payload such as a therapeutic protein inside by a self-assembly procedure. The payload such as a therapeutic protein (e.g., insulin) within the NPs can exhibit sustained and tunable release, while the surface-coated targeting ligand (e.g., proteins such as transferrin) can alter the NP cellular behaviors. In vivo results show that the transferrin-coated NPs can effectively be transported across the intestinal epithelium for oral insulin delivery, leading to a notable hypoglycemic response.

Receptor-mediated transcytosis has exhibited significant potential in promoting transepithelial absorption (see, e.g., E. M. Pridgen, F. Alexis, O. C. Farokhzad, *Clin Gastroenterol Hepatol* 2014, 12, 1605-1610). For example, neonatal FcRn-mediated transcytosis of NPs that target the FcRn receptor has recently been shown to be a feasible approach for transepithelial transport of therapeutics (see, e.g., Pridgen, et al., *Sci. Transl. Med.* 2013, 5, 213ra167). One important obstacle these NPs still face is that surface modification with protein-based ligands after protein loading should be avoided due to their susceptibility to conjugation reactions and unwanted release.

Figure 1A:
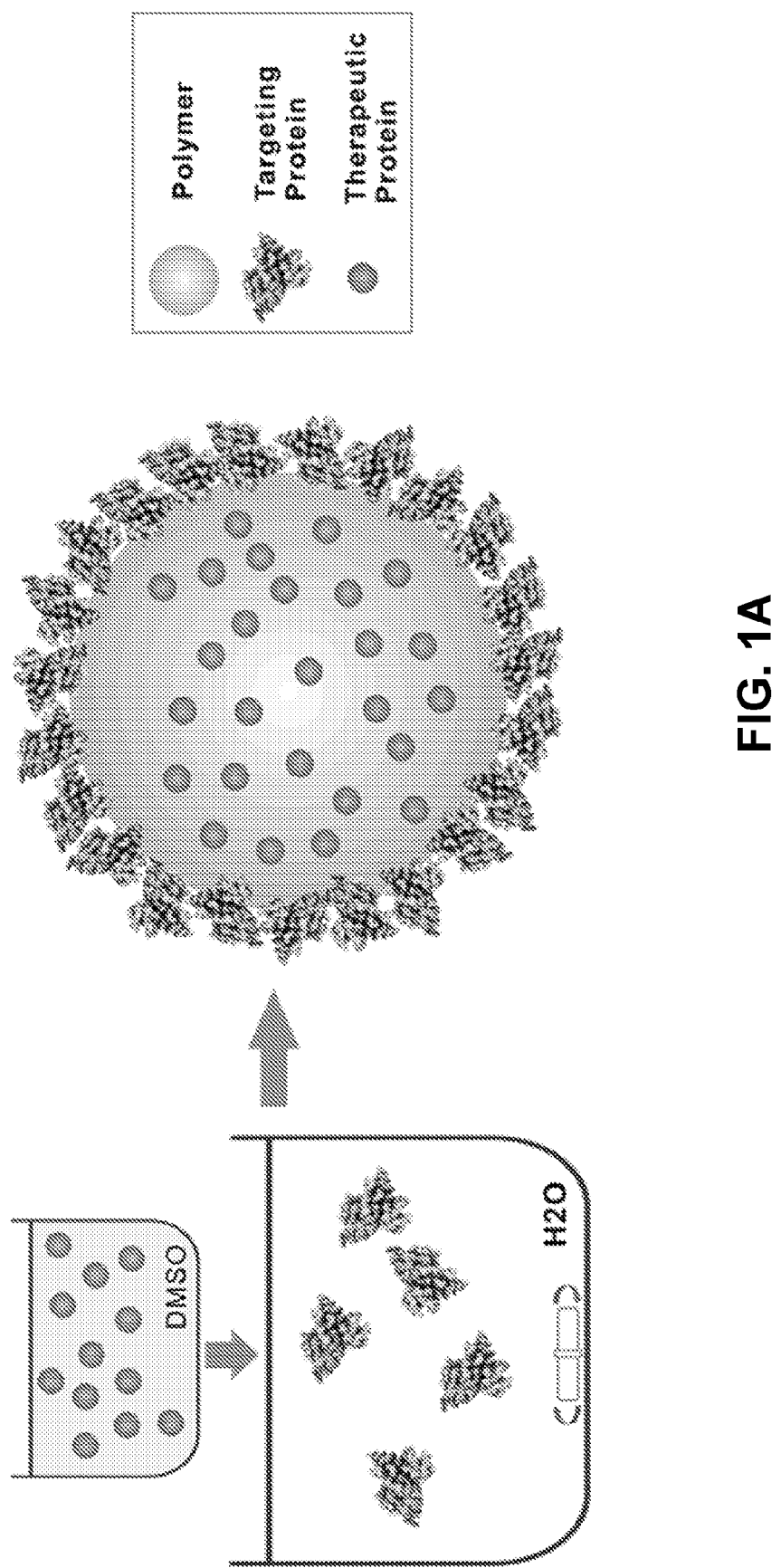
FIG. 1A is schematic diagram of the nanoparticle structure and the self-assembly process for nanoparticles (NPs).

The present disclosure describes a novel NP platform that is capable of simultaneous installation of targeting ligands (e.g., proteins) on the exterior and loading of a payload such as therapeutic proteins in the interior of the NP in a single self-assembly step (shown schematically in FIG. 1A). Since major types of proteins are negatively charged, and have hydrophobic regions (see, e.g., Frokjaer, et al., *Nat. Rev. Drug Discov.* 2005, 4, 298-306; Wu et al., *Angew. Chem. Int. Ed.*, 2014, 53, 8975-8979), polymers with combined cationic and hydrophobic characteristics may have a strong affinity with proteins. Therefore, a family of water-insoluble polymers with a wide-ranging, yet tunable, set of cationic and hydrophobic features was developed. These polymers can form NPs via self-assembly, and the payload such as a therapeutic and targeting ligand such as a protein ligand can be simultaneously and selectively installed in the interior and at the exterior, respectively, of the NP. The physically loaded targeting ligand on the NP surface can be demonstrated to alter the NP's behaviors, and the payload such as encapsulated proteins within the NPs is well protected and can exhibit sustained and tunable release.

As an illustration of the capabilities of this platform, the feasibility of protein delivery of this NP platform has been demonstrated. In particular, the oral absorption of the NPs for treating, e.g., diabetes, has been shown. Insulin was loaded inside the NPs as an example of a therapeutic protein, while transferrin (Tf), a protein that can undergo transcytosis by binding to Tf receptors on epithelial cells, was installed as a model targeting protein.

Figure 1B:
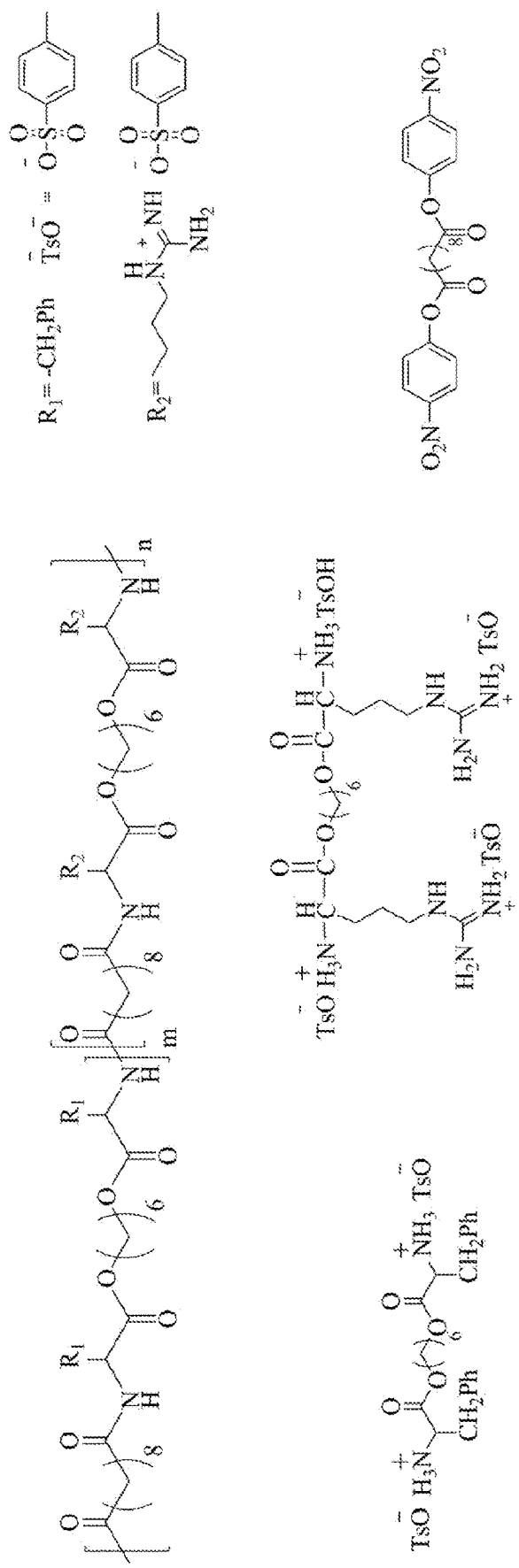
FIG. 1B contains formulae representing the chemical structures of monomers and the poly(ester amide) (PEA) polymer.

Poly(ester amide)s (PEAs) as NP material was utilized to make the nanoparticles, which are composed of amino acids, diols, and diacids (see FIG. 1B). Arginine (Arg) was used as an example of the cationic component, and phenylalanine (Phe) was used to mediate intra- and intermolecular interactions via hydrophobic force. PEAs were prepared via the solution polycondensation of monomers with various Phe to Arg ratios by changing the feed ratios of monomers I to II (FIG. 1B and FIG. 5, Example 1a, Table 1) (see, e.g., J. Wu, C.-C. Chu, *J. Mater. Chem. B* 2013, 1, 353-360).

In the present description, it is appreciated that certain features described herein, which are, for clarity, described in the context of separate embodiments, can also be provided in combination in a single embodiment. Conversely, various features described herein which are, for brevity, described in the context of a single embodiment, can also be provided separately or in any suitable subcombination.

Although methods and materials similar or equivalent to those described herein can be used in the practice or testing of the present invention, suitable methods and materials are described below. In addition, the materials, methods and examples are illustrative only and not intended to be limiting.

Definitions

Unless defined otherwise, all technical and scientific terms used herein have the same meaning as is commonly understood by one of ordinary skill in the art to which this disclosure belongs.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

The term "particle" as used herein refers to a composition having a size from about 1 nm to about 1000 μm.

The term "microparticle" as used herein refers to a particle having a size from about 1000 nm to about 1 mm.

The term "nanoparticle" as used herein refers to a particle having a size from about 1 nm to about 1000 nm.

The term "particle size" (or "nanoparticle size" or "microparticle size") as used herein refers to the median size in a distribution of nanoparticles or microparticles. The median size is determined from the average linear dimension of individual nanoparticles, for example, the diameter of a spherical nanoparticle. Size may be determined by any number of methods in the art, including dynamic light scattering (DLS) and transmission electron microscopy (TEM) techniques.

The term "Encapsulation efficiency" (EE) as used herein is the ratio of the amount of drug that is encapsulated by the particles (e.g., nanoparticles) to the initial amount of drug used in preparation of the particle.

The term "Loading capacity" (LC) or "loading efficiency" (LE) as used herein is the mass fraction of drug that is encapsulated to the total mass of the particles (e.g., nanoparticles).

"Polymer" as used herein, is given its ordinary meaning as used in the art, i.e., a molecular structure including one or more repeat units (monomers), connected by covalent bonds. "Copolymer" as used herein refers to a polymer with more than one type of repeat unit present within the polymer.

As used herein, "payload" refers to a matter contained within the particle that can be advantageously delivered e.g. to a cell or an organism. In some embodiments, payload is a biomolecule. In some embodiments, payload is a biologically active compound such as a therapeutically active compound such as a drug or a protein.

As used herein, "selectively encapsulated" refers to a payload that has a greater concentration in the core of the particle than in the outer layer. In some embodiments, the ratio of concentration of payload in the core is to the concentration of payload in outer layer is 100 to 1 or higher, 500 to 1 or higher, 1,000 to 1 or higher, 2,000 to 1 or higher, 4,000 to 1 or higher, 5,000 to 1 or higher, 6,000 to 1 or higher, 7,000 to 1 or higher, 8,000 to 1 or higher, 9,000 to 1 or higher, or 10,000 to 1 or higher.

As used herein, "room temperature" refers to ambient indoor temperature, typically a temperature from about 15° C. to about 25° C. In some embodiments, room temperature is 18° C.

As used herein, the term "adjuvant" refers to an immunological adjuvant. By this is meant a compound or composition that is able to enhance or facilitate the immune system's response to a pathogen, thereby inducing an immune response or series of immune responses in the subject. The adjuvant can facilitate the effect of the compositions, e.g., by forming depots (prolonging the half-life of the composition), provide additional T-cell help, and/or stimulate cytokine production Abbreviations The following abbreviations may be used in the present disclosure. DTX-docetaxel; DLS=differential light scattering; DMSO=dimethylsulfoxide; DSPE=1,2-distearoyl-sn-glycero-3-phosphoethanolamine; EIPA=5-(N-ethyl-N-isopropyl)amiloride; FBS=fetal bovine serum; IL=interleukin; IP=intraperitoneal; LPS=lipopolysaccharide; mAb=monoclonal antibody; miR=miRNA, microRNA or micro ribonucleic acid; mRNA=messenger ribonucleic acid; MWCO=molecular weight cutoff; NP=nanoparticle; PCR=polymerase chain reaction; PBS=phosphate-buffered saline; PEG=poly(ethylene glycol); PEI=polyethylenimine; PHB1=Prohibitin 1 protein; PLA=poly (lactic acid); PLGA=poly(lactic-co-glycolic acid); PCL=polycaprolactone, PBS=polybutylene succinate, PHA=polyhydroxylalkanoate; RNAi=ribonucleic acid interference; mRNA=messenger ribonucleic acid; shRNA=short hairpin ribonucleic acid; siRNA=small interfering ribonucleic acid, short interfering ribonucleic acid, or silencing ribonucleic acid; SD=standard deviation; SEM=standard error of the mean; TEM=transmission electron microscopy; TNF=tumor necrosis factor; DMF=deoxyribonucleic acid; PEA=poly(ester amide); GH=growth hormone; AIDS=acquired immune deficiency syndrome; HIV=human immunodeficiency virus; FVC=forced vital capacity; HPV=Human papillomavirus; DNA=deoxyribonucleic acid; cDNA=complementary deoxyribonucleic acid; PPG=polypropylene glycol; NMR=nuclear magnetic resonance; FTIR=Fourier transform infrared spectroscopy; BSA=bovine serum albumin; CBB=Coomassie Brilliant Blue; PDI=polydispersity index; SGF=simulated gastric fluid; HPLC=high performance liquid chromatography; TFA=trifluoroacetic acid; TEER=transepithelial electrical resistance.

Particles of the Present Disclosure

The present disclosure provides, inter alia, a particle comprising (i) a core comprising a polymer that comprises a positively charged component and a hydrophobic component; and (ii) a payload molecule within the core. The particle can further include (iii) a surface layer comprising a targeting ligand that binds or reacts selectively with a receptor on the outside surface of a cell.

In some embodiments, the core comprises any one of polymers that comprise a positively charged component and a hydrophobic component as described herein.

In some embodiments, the core of the particle further comprises a variety of materials.

In some embodiments, the core of the particle comprises a hydrophobic polymer. In some embodiments, the hydrophobic polymer is selected from the group consisting of polylactic acid (PLA), polypropylene oxide, poly(lactide-co-glycolide) (PLGA), poly(epsilon-caprolactone), poly(ethylethylene), polybutadiene, polyglycolide, polymethylacrylate, polyvinylbutylether, polystyrene, polycyclopentadienyl-methylnorbornene, polyethylenepropylene, polyethylethylene, polyisobutylene, polysiloxane, an acrylic polymer (e.g., methyl acrylate, ethyl acrylate, propyl acrylate, n-butyl acrylate, isobutyl acrylate, 2-ethyl acrylate, t-butyl acrylate, a methacrylic polymer (e.g., ethyl methacrylate, n-butyl methacrylate, and isobutyl methacrylate), acrylonitriles, methacrylonitrile, vinyls (e.g., vinyl acetate, vinylversatate, vinylpropionate, vinylformamide, vinylacetamide, vinylpyridines, and vinyllimidazole), aminoalkyls (e.g., aminoalkylacrylates, aminoalkylsmethacrylates, aminoalkyl(meth)acrylamides), styrenes, and lactic acids.

In some embodiments, the core comprises an amphiphilic polymer.

In some embodiments, amphiphilic polymers contain a molecular structure containing one or more repeating units (monomers) connected by covalent bonds and the overall structure includes both hydrophilic (polar) and lipophilic (apolar) properties, e.g., at opposite ends of the molecule. In some embodiments, the amphiphilic polymers are copolymers containing a first hydrophilic polymer and a first hydrophobic polymer.

In some embodiments, the amphiphilic polymer contains PLA-PEG, PLGA-PEG (e.g., the amphiphilic polymer is PLGA-PEG), polystyreneblock-polyethyleneoxide, polybutylacrylate-b-polyacrylic acid, or polybutylmethacrylate-b-polyethyleneoxide. Additional examples of amphiphilic copolymers are described in U.S. Patent Application Publication No. 2004/0091546 (incorporated herein by reference in its entirety). Additional examples of amphiphilic polymers (e.g., amphiphilic copolymers) are known in the art.

In some embodiments, the core comprises a polymer comprising an aliphatic polyester polymer.

In some embodiments, the aliphatic polyester polymer is selected from the group consisting of polycaprolactone (PCL), polybutylene succinate (PBS), and a polyhydroxylalkanoate (PHA), such as polyhydroxybutyrate. In some embodiments, aliphatic polyester polymer is selected from polylactic acid (PLA) and polyglycolic acid (PGA). In some embodiments, the aliphatic polyester polymer is selected from polylactic acids, polyglycolic acids, and copolymers of lactic acid and glycolic acid (PLGA).

In some embodiments, the core of the particle comprises poly(lactide-co-glycolide) (PLGA). In some embodiments, the poly(lactide-co-glycolide) (PLGA) comprises a range of ratios of lactic acid to glycolic acid monomers, for example, from about 1:9 to about 9:1, from about 1:4 to about 4:1, from about 3:7 to about 7:3, or from about 3:2 to about 2:3. In some embodiments, the ratio of lactic acid to glycolic acid monomers can be about 1:9; about 1:8; about 1:7; about 1:6; about 1:5; about 1:4; about 3:7; about 2:3; about 1:1; about 3:2; about 7:3; about 4:1; about 5:1; about 6:1; about 7:1; about 8:1; or about 9:1. In some embodiments, the core can consist essentially of, or consist of, such materials.

In some embodiments, the range of ratios of the poly(lactide-co-glycolide) (PLGA) in the core of the particle to a polymer that comprises a positively charged component and a hydrophobic component is from about 1:9 to about 9:1, from about 1:4 to about 4:1, from about 3:7 to about 7:3, or from about 3:2 to about 2:3 on the wt % basis. In some embodiments, the ratio of the poly(lactide-co-glycolide) (PLGA) in the core of the particle to a polymer that comprises a positively charged component and a hydrophobic component is about 1:9; about 1:8; about 1:7; about 1:6; about 1:5; about 1:4; about 3:7; about 2:3; about 1:1; about 3:2; about 7:3; about 4:1; about 5:1; about 6:1; about 7:1; about 8:1; or about 9:1 on the wt % basis. In some embodiments, the ratio of the poly(lactide-co-glycolide) (PLGA) in the core of the particle to a polymer that comprises a positively charged component and a hydrophobic component is about 1:1 on the wt % basis.

In some embodiments, the core of the particle (and particularly the surface of the core) can have a positive charge (i.e. zeta (ζ) potential). In some embodiments, a net positive charge is provided by basic groups (e.g. amine, ammonium groups, or guanidinium groups) included in a material included in the core. In some embodiments, a net positive charge is provided by basic amino acid residues (e.g. arginine, histidine, or lysine residues) included in a material included in the core.

In some embodiments, the zeta potential can range from about +0.1 mV to about +100 mV. In some embodiments, the zeta potential can range from about +1 mV to about +90 mV. In some embodiments, the zeta potential can range from about +2 mV to about +80 mV. In some embodiments, the zeta potential can range from about +3 mV to about +70 mV. In some embodiments, the zeta potential can range from about +4 mV to about +60 mV. In some embodiments, the zeta potential can range from about +5 mV to about +50 mV. In some embodiments, the zeta potential can range from about +6 mV to about +40 mV. In some embodiments, the zeta potential can range from about +11 mV to about +32 mV. In some embodiments, the zeta potential can range from about +11.8 mV to about +31.3 mV.

In some embodiments, the core comprises an inorganic material. For example, the inorganic material can be a nanoparticle comprising gold, silver, copper, zinc, titanium, iron, platinum, palladium, gadolinium, lithium, and/or silicon. Other non-limiting examples of inorganic materials include metal oxides (e.g., iron oxide), silica, and carbon (e.g., carbon nanospheres). In some embodiments, the nanoparticle of inorganic material is a gold nanosphere. In some embodiments, the size of the nanoparticle of the inorganic material can be in a range from about 1 nm to about 20 nm, from about 2 nm to about 15 nm, from about 3 nm to about 10 nm. In some embodiments, the size of the nanoparticle of the inorganic material is 5 nm. In some embodiments, the nanoparticle of the inorganic material can be conjugated with any one of the payload molecules described herein. In some embodiments, the nanoparticle of the inorganic material can be conjugated with a therapeutic protein. In some embodiments, the nanoparticle of the inorganic material can be conjugated with bovine serum albumin (e.g., BSA-Au). In some embodiments, the conjugation between the nanoparticle of the inorganic material and the payload molecule (e.g., a therapeutic protein) is covalent. In some embodiments, the conjugation between the nanoparticle of the inorganic material and the payload molecule (e.g., a therapeutic protein) is non-covalent.

In some embodiments, the core of the particle comprises a payload molecule as described herein. In some embodiments, the payload is a therapeutic protein as described herein. In some embodiments, the payload is a small molecule therapeutic.

In some embodiments, the core of the particle can comprise more than one payload molecule.

In some embodiments, the core may comprise a second payload molecule. In some embodiments, the second payload is a therapeutic protein as described herein. In some embodiments, the second payload is a small molecule therapeutic. In some embodiments, the payloads in the core may be different therapeutic proteins that offer complementary therapeutic effects for a disease or condition, and can be released at different times or under diverse environmental changes, e.g., differential pH or reducing conditions.

In some embodiments, the particle of the disclosure can have encapsulation efficiency (EE) with respect to one or more payload molecules within the core from about 1% to about 99%, from about 20% to about 98%, from about 50% to about 97%, or from about 70% to about 95%. In some embodiments, the particle of the disclosure can have encapsulation efficiency (EE) with respect to one or more payload molecules within the core of about 85% or more, about 90% or more, about 95% or more, or about 99% or more.

In some embodiments, the particle of the disclosure can have loading efficiency (LE) with respect to one or more payload molecules within the core from about 1 wt % to about 50 wt %. In some embodiments, the loading efficiency (LE) is from about 2 wt % to about 40 wt %. In some embodiments, the loading efficiency (LE) is from about 3 wt % to about 30 wt %. In some embodiments, the loading efficiency is from about 4 wt % to about 20 wt %. In some embodiments, the loading efficiency is from about 5 wt % to about 10 wt %. In some embodiments, the loading efficiency is about 1 wt % or more, about 2 wt % or more, about 3 wt % or more, about 4 wt % or more, about 5 wt % or more, about 6 wt % or more, about 7 wt % or more, about 8 wt % or more, about 9 wt % or more, or about 10 wt % or more. In some embodiments, the loading efficiency is about 9 wt %.

In some embodiments, the payload molecule is encapsulated selectively in the core of the particle so that the surface of the particle can be substantially free of the payload molecule. For example, about 80% or more, about 85% or more, about 90% or more, about 95% or more, about 98% or more, about 99% or more, or about 100% of the of the payload molecule can be encapsulated in the core of the particle.

In some embodiments, the surface layer of the particle comprises any one of the targeting ligands that binds or reacts selectively with a receptor on the outside surface of a cell as described herein.

In some embodiments, the particle of the present disclosure is a nanoparticle. In some embodiments, the size of the nanoparticle can be in a range from about 20 nm to about 500 nm. In some embodiments, the size can be in a range from about 40 nm to about 300 nm. In some embodiments, the size can be in a range from about 50 nm to about 200 nm. In some embodiments, the size can be in a range from about 60 nm to about 130 nm. In some embodiments, the size can be in a range from about 80 nm to about 110 nm. In some embodiments, the size of the nanoparticle of the present disclosure is about 100 nm.

In some embodiments the particle of the present disclosure is a microparticle with a size in the range from about 1000 nm to about 1 mm, e.g., from about 1000 nm to about 0.1 mm.

In some embodiments, the shape of the nanoparticle is spherical, cylindrical, hemispherical, rod-shaped, or conical. In some embodiments, the nanoparticle is spherical or substantially spherical.

In some embodiments, the nanoparticles present within a population, e.g., in a composition, can have substantially the same shape and/or size (i.e., they are "monodisperse"). For example, the particles can have a distribution such that no more than about 5% or about 10% of the nanoparticles have a diameter greater than about 10% greater than the average diameter of the particles, and in some cases, such that no more than about 8%, about 5%, about 3%, about 1%, about 0.3%, about 0.1%, about 0.03%, or about 0.01% have a diameter greater than about 10% greater than the average diameter of the nanoparticles.

In some embodiments, the diameter of no more than 25% of the nanoparticles varies from the mean nanoparticle diameter by more than 150%, 100%, 75%, 50%, 25%, 20%, 10%, or 5% of the mean nanoparticle diameter. It is often desirable to produce a population of nanoparticles that is relatively uniform in terms of size, shape, and/or composition so that most of the nanoparticles have similar properties. For example, at least 80%, at least 90%, or at least 95% of the nanoparticles produced using the methods described herein can have a diameter or greatest dimension that falls within 5%, 10%, or 20% of the average diameter or greatest dimension. In some embodiments, a population of nanoparticles can be heterogeneous with respect to size, shape, and/or composition. In some embodiments, the nanoparticle is any one of nanoparticles described, for example, in Zhu et al. Polymeric Nanoparticles Amenable to Simultaneous Installation of Exterior Targeting and Interior Therapeutic Proteins *Angewandte Chemie International Edition*, 2016, 55(10), 3235-3280, the disclosure of which is incorporated herein by reference in its entirety.

Polymers Comprising a Positively Charged Component and a Hydrophobic Component

The present disclosure provides, inter alia, a polymer that comprises a positively charged component and a hydrophobic component. In some embodiments, the polymer may be used to prepare a particle as described herein.

In some embodiments, the positively charged component comprises an aminoacid residue. In some embodiments, the hydrophobic component comprises an aminoacid residue. In some embodiments, the positively charged component and the hydrophobic component each comprise an aminoacid residue.

In some embodiments, the aminoacid residue is a natural amino acid residue.

In some embodiments, the aminoacid residue is an unnatural amino acid residue.

In some embodiments, the number of hydrophobic aminoacid residues in the polymer ranges from about 10 to about 1000, from about 10 to about 800, from about 10 to about 500, from about 10 to about 200, from about 20 to about 200, from about 20 to about 500, from about 20 to about 1000, from about 30 to about 200, from about 40 to about 200, from about 50 to about 100, or from about 60 to about 80.

In some embodiments, the number of positively charged aminoacid residues in the polymer ranges from about 10 to about 1000, from about 10 to about 800, from about 10 to about 500, from about 10 to about 200, from about 20 to about 200, from about 20 to about 500, from about 20 to about 1000, from about 30 to about 200, from about 40 to about 200, from about 50 to about 100, or from about 60 to about 80.

In some embodiments, the hydrophobic aminoacid residue is a residue of alanine, valine, leucine, isoleucine, methionine, phenylalanine, tyrosine, or tryptophan. In some embodiments, the hydrophobic aminoacid residue is phenylalanine In some embodiments, the positively charged aminoacid residue is a residue of arginine, histidine or lysine. In some embodiments, the positively charged aminoacid residue is arginine.

In some embodiments, the polymer further comprises a hydrocarbon linker between the positively charged component and the hydrophobic component.

In some embodiments, the hydrocarbon linker comprises 3-100 carbon atoms.

In some embodiments, the hydrocarbon linker comprises 4-10 carbon atoms.

In some embodiments, the hydrocarbon linker has the following Formula L-1:

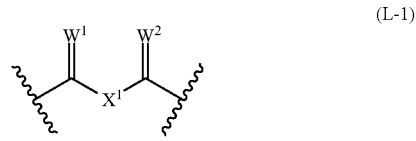

In some embodiments of Formula L-1, $W^1$ is O, S, or NH. In some embodiments of Formula L-1, $W^1$ is O or S. In some embodiments of Formula L-1, $W^1$ is O.

In some embodiments of Formula L-1, $W^2$ is O, S, or NH. In some embodiments of Formula L-1, $W^2$ is O or S. In some embodiments of Formula L-1, $W^2$ is O.

In some embodiments of Formula L-1, $X^1$ is $C_{1-100}$ alkylene, $C_{2-100}$ alkenylene, or $C_{2-100}$ alkynylene, each of which is optionally substituted with 1, 2, or 3 substituents independently selected from the group consisting of: halo, —CN, OH, amino, $C_{1-3}$ alkylamino, $C_{1-3}$ dialkylamino or carboxy.

In some embodiments of Formula L-1, $X^1$ is $C_{1-100}$ alkylene optionally substituted with 1, 2, or 3 substituents independently selected from the group consisting of: halo, —CN, OH, amino, $C_{1-3}$ alkylamino, $C_{1-3}$ dialkylamino or carboxy.

In some embodiments of Formula L-1, $X^1$ is $C_{2-20}$ alkylene.

In some embodiments, the hydrocarbon linker is a derivative of adipic, sebacic, malonic, succinic, glutaric, pimelic, suberic, or azelaic acid.

In some embodiments, the hydrocarbon linker is a derivative of adipic or sebacic acid. In some embodiments, the hydrocarbon linker is a derivative of adipic acid. In some embodiments, the hydrocarbon linker is a derivative of sebacic acid.

In some embodiments, the polymer that comprises a positively charged component and a hydrophobic component is a poly(ester amide) polymer comprising a repeating unit of Formula (Ia):

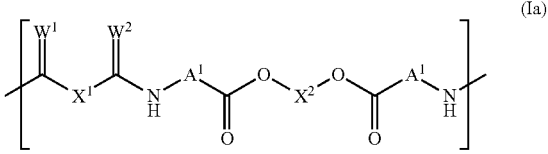

and a repeating unit of Formula (Ib):

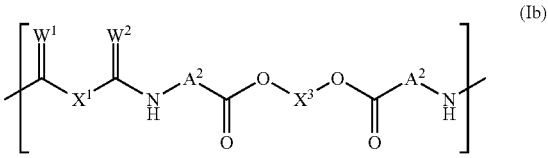

wherein:

each $X^1$ is $C_{1-100}$ alkylene, $C_{2-100}$ alkenylene, or $C_{2-100}$ alkynylene, each of which is optionally substituted with 1, 2, or 3 substituents independently selected from the group consisting of: halo, —CN, $R^1$, $OR^1$, $NR^1R^2$, —(C=O)$R^2$, —(C=O)$OR^2$, —(C=O)$NR^1R^2$, and —S(O)$_m R^2$;

$X^2$ is $C_{1-100}$ alkylene, $C_{2-100}$ alkenylene, or $C_{2-100}$ alkynylene, each of which is optionally substituted with 1, 2, or 3 substituents independently selected from the group consisting of: halo, —CN, $R^1$, $OR^1$, $NR^1R^2$, —(C=O)$R^2$, —(C=O)$OR^2$, —(C=O)$NR^1R^2$, and —S(O)$_m R^2$;

$X^3$ is $C_{1-100}$ alkylene, $C_{2-100}$ alkenylene, or $C_{2-100}$ alkynylene, each of which is optionally substituted with 1, 2, or 3 substituents independently selected from the group consisting of: halo, —CN, $R^1$, $OR^1$, $NR^1R^2$, —(C=O)$R^2$, —(C=O)$OR^2$, —(C=O)$NR^1R^2$, and —S(O)$_m R^2$;

each $R^1$ is H, $C_{1-6}$ alkyl, $C_{2-6}$ alkenyl, $C_{2-6}$ alkynyl, $C_{3-10}$ cycloalkyl, $C_{6-10}$ aryl, 5-10-membered heteroaryl, or 4-10-membered heterocycloalkyl, each of which is optionally substituted with 1, 2, or 3 substituents independently selected from the group consisting of OH, $NO_2$, CN, halo, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thiol, $C_{1-6}$ alkylthio, $C_{1-6}$ alkylsulfinyl, $C_{1-6}$ alkylsulfonyl, carboxy, $C_{1-6}$ alkylcarbonyl, and $C_{1-6}$ alkoxycarbonyl;

each $R^2$ is H, $C_{1-6}$ alkyl, $C_{2-6}$ alkenyl, $C_{2-6}$ alkynyl, $C_{3-10}$ cycloalkyl, $C_{6-10}$ aryl, 5-10-membered heteroaryl, or 4-10-membered heterocycloalkyl, each of which is optionally substituted with 1, 2, or 3 substituents independently selected from the group consisting of OH, $NO_2$, CN, halo, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thiol, $C_{1-6}$ alkylthio, $C_{1-6}$ alkylsulfinyl, $C_{1-6}$ alkylsulfonyl, carboxy, $C_{1-6}$ alkylcarbonyl, and $C_{1-6}$ alkoxycarbonyl;

each m is 0, 1 or 2;
each $W^1$ is O, S, or NH;
each $W^2$ is O, S, or NH;
each $A^1$ is a hydrophobic aminoacid residue; and
each $A^2$ is a cationic aminoacid residue.

In some embodiments, each $X^1$ is $C_{1-100}$ alkylene optionally substituted with 1, 2, or 3 substituents independently selected from the group consisting of: halo, —CN, $R^1$, $OR^1$, $NR^1R^2$, —(C=O)$R^2$, —(C=O)$OR^2$, —(C=O)$NR^1R^2$, and —S(O)$_m R^2$.

In some embodiments, each $X^1$ is $C_{1-100}$ alkylene optionally substituted with 1, 2, or 3 substituents independently selected from the group consisting of: halo, —CN, OH, amino, $C_{1-3}$ alkylamino, $C_{1-3}$ dialkylamino or carboxy.

In some embodiments, each $X^1$ is $C_{2-20}$ alkylene,
In some embodiments, each $X^1$ is butylene.
In some embodiments, each $X^1$ is octylene.

In some embodiments, each $X^2$ is $C_{1-100}$ alkylene optionally substituted with 1, 2, or 3 substituents independently selected from the group consisting of: halo, —CN, $R^1$, $OR^1$, $NR^1R^2$, —(C=O)$R^2$, —(C=O)$OR^2$, —(C=O)$NR^1R^2$, and —S(O)$_m R^2$.

In some embodiments, each $X^2$ is $C_{1-100}$ alkylene optionally substituted with 1, 2, or 3 substituents independently selected from the group consisting of: halo, —CN, OH, amino, $C_{1-3}$ alkylamino, $C_{1-3}$ dialkylamino or carboxy.

In some embodiments, each $X^2$ is $C_{2-20}$ alkylene.
In some embodiments, each $X^2$ is butylene.
In some embodiments, each $X^2$ is hexylene.

In some embodiments, each $X^3$ is $C_{1-100}$ alkylene optionally substituted with 1, 2, or 3 substituents independently selected from the group consisting of: halo, —CN, $R^1$, $OR^1$, $NR^1R^2$, —(C=O)$R^2$, —(C=O)$OR^2$, —(C=O)$NR^1R^2$, and —S(O)$_m R^2$.

In some embodiments, each $X^3$ is $C_{1-100}$ alkylene optionally substituted with 1, 2, or 3 substituents independently selected from the group consisting of: halo, —CN, OH, amino, $C_{1-3}$ alkylamino, $C_{1-3}$ dialkylamino or carboxy.

In some embodiments, each $X^3$ is $C_{2-20}$ alkylene,
In some embodiments, each $X^3$ is butylene.
In some embodiments, each $X^3$ is hexylene.

In some embodiments, $R^1$ is H, $C_{1-6}$ alkyl, $C_{2-6}$ alkenyl or $C_{2-6}$ alkynyl.
In some embodiments $R^1$ is H.
In some embodiments, $R^2$ is H, $C_{1-6}$ alkyl, $C_{2-6}$ alkenyl or $C_{2-6}$ alkynyl.
In some embodiments $R^2$ is H.
In some embodiments, $W^1$ is O or S.
In some embodiments, $W^1$ is O.
In some embodiments, $W^2$ is O or S.
In some embodiments, $W^2$ is O.

In some embodiments, the repeating unit of Formula (Ia) has Formula (IIa)

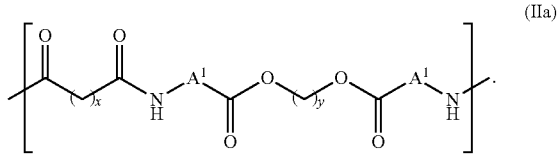

In some embodiments, the repeating unit of Formula (Ib) has Formula (IIb):

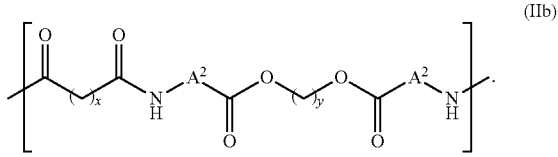

In some embodiments, x is an integer from 1 to 12. In some embodiments, x is 1, 2, 3, 4, 5, 6, 7, 8, 9, 10, 11, or 12. In some embodiments, x is 4. I some embodiments, x is 6. I some embodiments, x is 8.

In some embodiments, y is an integer from 1 to 10. In some embodiments, y is 1, 2, 3, 4, 5, 6, 7, 8, 9 or 10. In some embodiments, y is 4. In some embodiments, y is 6.

In some embodiments, x is an integer from 2 to 10 and y is an integer from 2 to 8.

In some embodiments, x is 4 and y is 4.
In some embodiments, x is 4 and y is 6.
In some embodiments, x is 6 and y is 4.
In some embodiments, x is 6 and y is 6.

In some embodiments, each $A^1$ is a residue of natural aminoacid.

In some embodiments, $A^1$ is a residue of alanine, valine, leucine, isoleucine, methionine, phenylalanine, tyrosine, or tryptophan. In some embodiments, $A^1$ is a residue of phenylalanine. In some embodiments, $A^1$ is a residue of alanine.

In some embodiments, each $A^1$ is a residue of unnatural aminoacid.

In some embodiments, each $A^1$ is a residue of a derivative of alanine, valine, leucine, isoleucine, methionine, phenylalanine, tyrosine, or tryptophan.

In some embodiments, one $A^1$ group is a residue of natural aminoacid and the other $A^1$ group is a residue of unnatural aminoacid.

In some embodiments, $A^2$ is a residue of natural aminoacid.

In some embodiments, $A^2$ is a residue of arginine, histidine or lysine. In some embodiments, $A^2$ is a residue of arginine In some embodiments, $A^2$ is a residue of unnatural aminoacid.

In some embodiments, $A^2$ is a residue of a derivative of arginine, histidine or lysine.

In some embodiments, one $A^2$ group is a residue of natural aminoacid and the other $A^2$ group is a residue of unnatural aminoacid.

In some embodiments, $A^1$ is selected from the group of the following Formulae:

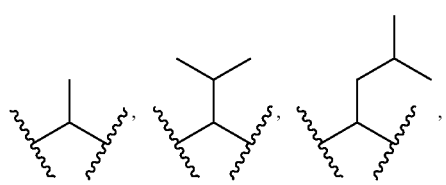

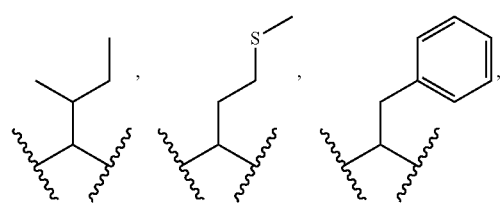

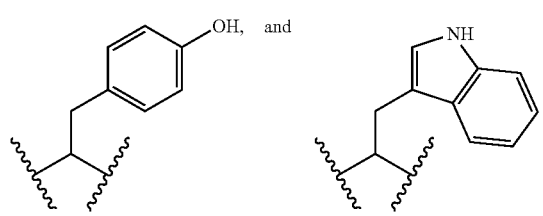

In some embodiments, $A^1$ is

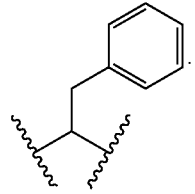 [SMILES: *C(*)Cc1ccccc1]

In some embodiments, the aminoacid residue of $A^1$ is in D configuration.

In some embodiments, the aminoacid residue of $A^1$ is in L configuration.

In some embodiments, $A^2$ is selected from the group of the following Formulae:

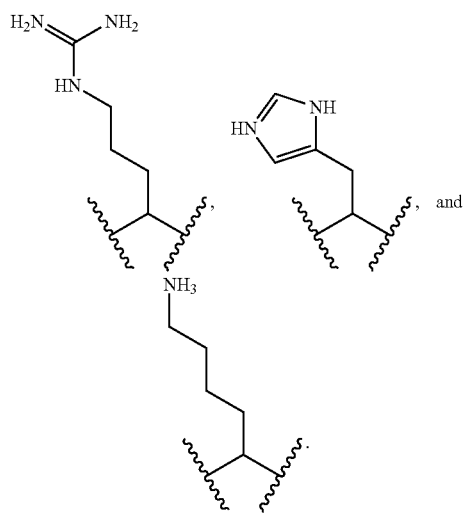

In some embodiments, $A^2$ is

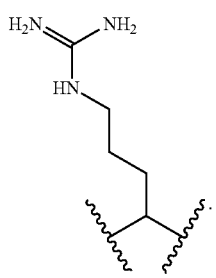 [SMILES: *C(*)CCCNC(=N)N]

In some embodiments, the aminoacid residue of $A^2$ is in D configuration.

In some embodiments, the aminoacid residue of $A^2$ is in L configuration.

In some embodiments, the repeating unit of Formula (Ia) has Formula (IIIa):

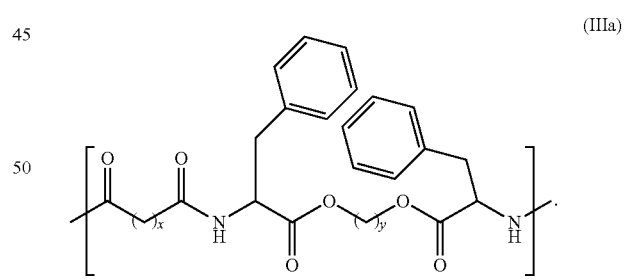

(IIIa)

In some embodiments, the repeating unit of Formula (Ia) has Formula (IIId):

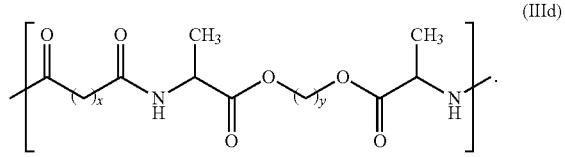

(IIId)

In some embodiments of Formula (IIIa) or (IIId), x is 1, 2, 3, 4, 5, 6, 7 or 8.

In some embodiments of Formula (IIIa) or (IIId), y is 1, 2, 3, 4, 5 or 6.

In some embodiments of Formula (IIIa) or (IIId), x is 4 and y is 6.

In some embodiments of Formula (IIIa) or (IIId), x is 8 and y is 6.

In some embodiments of Formula (IIIa) or (IIId), x is 6 and y is 6.

In some embodiments, the repeating unit of Formula (Ib) has Formula (IIIb):

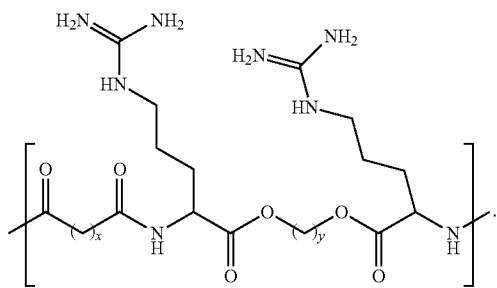

In some embodiments of Formula (IIIb), x is 1, 2, 3, 4, 5, 6, 7 or 8.

In some embodiments of Formula (IIIb), y is 1, 2, 3, 4, 5 or 6.

In some embodiments of Formula (IIIb), x is 4 and y is 6.
In some embodiments of Formula (IIIb), x is 8 and y is 6.
In some embodiments of Formula (IIIb), x is 6 and y is 6.

In some embodiments, the polymer that comprises a positively charged component and a hydrophobic component is a poly(ester amide) polymer comprising a repeating unit of Formula (Ic):

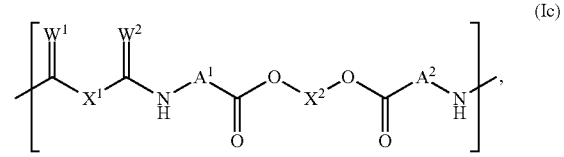

wherein:

each $X^1$ is $C_{1-100}$ alkylene, $C_{2-100}$ alkenylene, or $C_{2-100}$ alkynylene, each of which is optionally substituted with 1, 2, or 3 substituents independently selected from the group consisting of: halo, —CN, $R^1$, $OR^1$, $NR^1R^2$, —(C=O)$R^2$, —(C=O)O$R^2$, —(C=O)N$R^1R^2$, and —S(O)$_m R^2$;

$X^2$ is $C_{1-100}$ alkylene, $C_{2-100}$ alkenylene, or $C_{2-100}$ alkynylene, each of which is optionally substituted with 1, 2, or 3 substituents independently selected from the group consisting of: halo, —CN, $R^1$, $OR^1$, $NR^1R^2$, —(C=O)$R^2$, —(C=O)O$R^2$, —(C=O)N$R^1R^2$, and —S(O)$_m R^2$;

each $R^1$ is H, $C_{1-6}$ alkyl, $C_{2-6}$ alkenyl, $C_{2-6}$ alkynyl, $C_{3-10}$ cycloalkyl, $C_{6-10}$ aryl, 5-10-membered heteroaryl, or 4-10-membered heterocycloalkyl, each of which is optionally substituted with 1, 2, or 3 substituents independently selected from the group consisting of OH, $NO_2$, CN, halo, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thiol, $C_{1-6}$ alkylthio, $C_{1-6}$ alkylsulfinyl, $C_{1-6}$ alkylsulfonyl, carboxy, $C_{1-6}$ alkylcarbonyl, and $C_{1-6}$ alkoxycarbonyl;

each $R^2$ is H, $C_{1-6}$ alkyl, $C_{2-6}$ alkenyl, $C_{2-6}$ alkynyl, $C_{3-10}$ cycloalkyl, $C_{6-10}$ aryl, 5-10-membered heteroaryl, or 4-10-membered heterocycloalkyl, each of which is optionally substituted with 1, 2, or 3 substituents independently selected from the group consisting of OH, $NO_2$, CN, halo, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thiol, $C_{1-6}$ alkylthio, $C_{1-6}$ alkylsulfinyl, $C_{1-6}$ alkylsulfonyl, carboxy, $C_{1-6}$ alkylcarbonyl, and $C_{1-6}$ alkoxycarbonyl;

each m is 0, 1 or 2;
each $W^1$ is O, S, or NH;
each $W^2$ is O, S, or NH;
each $A^1$ is a hydrophobic aminoacid residue; and
each $A^2$ is a cationic aminoacid residue.

In some embodiments of Formula (Ic), each $X^1$ is $C_{1-100}$ alkylene optionally substituted with 1, 2, or 3 substituents independently selected from the group consisting of: halo, —CN, $R^1$, $OR^1$, $NR^1R^2$, —(C=O)$R^2$, —(C=O)O$R^2$, —(C=O)N$R^1R^2$, and —S(O)$_m R^2$.

In some embodiments of Formula (Ic), each $X^1$ is $C_{1-100}$ alkylene optionally substituted with 1, 2, or 3 substituents independently selected from the group consisting of: halo, —CN, OH, amino, $C_{1-3}$ alkylamino, $C_{1-3}$ dialkylamino or carboxy.

In some embodiments of Formula (Ic), each $X^1$ is $C_{2-20}$ alkylene,

In some embodiments of Formula (Ic), each $X^1$ is butylene.

In some embodiments of Formula (Ic), each $X^1$ is octylene.

In some embodiments of Formula (Ic), each $X^2$ is $C_{1-100}$ alkylene optionally substituted with 1, 2, or 3 substituents independently selected from the group consisting of: halo, —CN, $R^1$, $OR^1$, $NR^1R^2$, —(C=O)$R^2$, —(C=O)O$R^2$, —(C=O)N$R^1R^2$, and —S(O)$_m R^2$.

In some embodiments of Formula (Ic), each $X^2$ is $C_{1-100}$ alkylene optionally substituted with 1, 2, or 3 substituents independently selected from the group consisting of: halo, —CN, OH, amino, $C_{1-3}$ alkylamino, $C_{1-3}$ dialkylamino or carboxy.

In some embodiments of Formula (Ic), each $X^2$ is $C_{2-20}$ alkylene.

In some embodiments of Formula (Ic), each $X^2$ is butylene.

In some embodiments of Formula (Ic), each $X^2$ is hexylene.

In some embodiments of Formula (Ic), $R^1$ is H, $C_{1-6}$ alkyl, $C_{2-6}$ alkenyl or $C_{2-6}$ alkynyl.

In some embodiments of Formula (Ic), $R^1$ is H.

In some embodiments of Formula (Ic), $R^2$ is H, $C_{1-6}$ alkyl, $C_{2-6}$ alkenyl or $C_{2-6}$ alkynyl.

In some embodiments of Formula (Ic), $R^2$ is H.
In some embodiments of Formula (Ic), $W^1$ is O or S.
In some embodiments of Formula (Ic), $W^1$ is O.
In some embodiments of Formula (Ic), $W^2$ is O or S.
In some embodiments of Formula (Ic), $W^2$ is O.

In some embodiments, the repeating unit of Formula (Ic) has Formula (IIc)

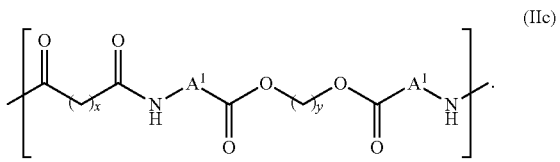
(IIc)

In some embodiments of Formula (IIc), x is an integer from 1 to 12.

In some embodiments of Formula (IIc), y is an integer from 1 to 10.

In some embodiments of Formula (IIc), x is an integer from 2 to 10 and y is an integer from 2 to 8.

In some embodiments of Formula (IIc), x is 1, 2, 3, 4, 5, 6, 7 or 8.

In some embodiments of Formula (IIc), y is 1, 2, 3, 4, 5 or 6.

In some embodiments of Formula (IIc), x is 4 and y is 6.
In some embodiments of Formula (IIc), x is 8 and y is 6.
In some embodiments of Formula (IIc), x is 6 and y is 6.

In some embodiments of Formula (Ic) or (IIc), $A^1$ is a residue of natural aminoacid. In some embodiments of Formula (Ic) or (IIc), $A^1$ is a residue of unnatural aminoacid. In some embodiments of Formula (Ic) or (IIc), the aminoacid residue of $A^1$ is in D configuration. In some embodiments of Formula (Ic) or (IIc), the aminoacid residue of $A^1$ is in L configuration.

In some embodiments of Formula (Ic) or (IIc), $A^2$ is a residue of natural aminoacid. In some embodiments of Formula (Ic) or (IIc), $A^2$ is a residue of unnatural aminoacid. In some embodiments of Formula (Ic) or (IIc), $A^2$ is a residue of unnatural aminoacid. In some embodiments of Formula (Ic) or (IIc), the aminoacid residue of $A^2$ is in D configuration. In some embodiments of Formula (Ic) or (IIc), the aminoacid residue of $A^2$ is in L configuration.

In some embodiments of Formula (Ic) or (IIc), $A^1$ is selected from the group of the following Formulae:

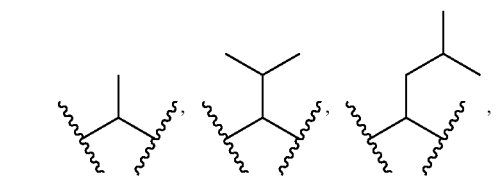

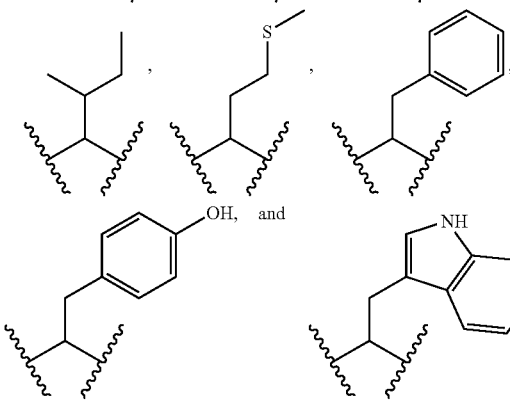

In some embodiments of Formula (Ic) or (IIc), $A^2$ is selected from the group of the following Formulae:

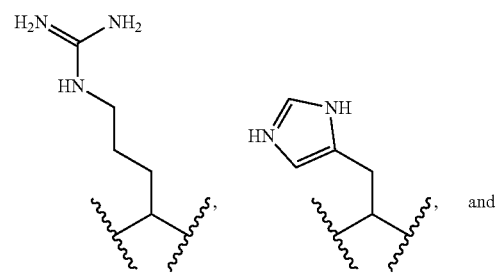

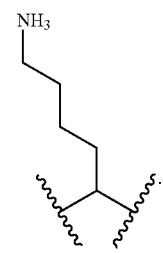

In some embodiments of Formula (Ic) or (IIc), $A^2$ is selected from the group of the following Formulae:

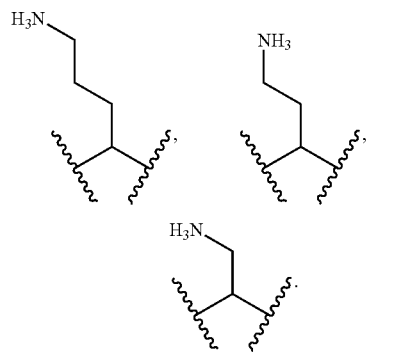

In some embodiments of Formula (Ic) or (IIc), the repeating unit of Formula (Ic) has Formula (IIIc):

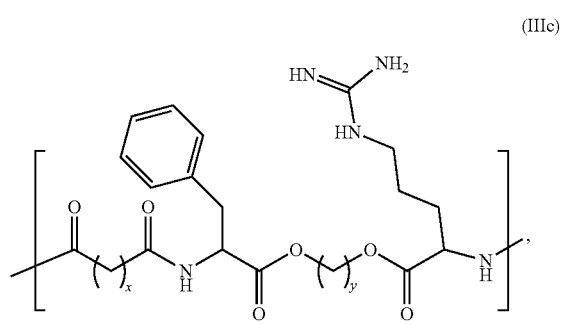
(IIIc)

wherein x is 4, 6 or 8 and y is 6.

In some embodiments of Formula (Ic) or (IIc), the repeating unit of Formula (Ic) has Formula (IIIe):

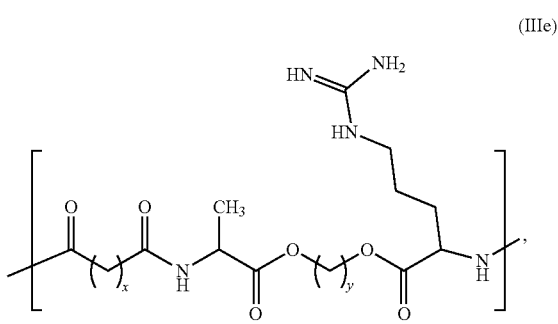

(IIIe)

wherein x is 4, 6 or 8 and y is 6.

In some embodiments, the number average molecular weight of the PEA polymer is from about 2 kg mol$^{-1}$ to about 50.0 kg mol$^{-1}$, from about 3 kg mol$^{-1}$ to about 40 kg mol$^{-1}$, from about 5.0 kg mol$^{-1}$ to about 35.0 kg mol$^{-1}$, from about 10.0 kg mol$^{-1}$ to about 30.0 kg mol$^{-1}$, or from about 15.0 kg mol$^{-1}$ to about 25.0 kg mol$^{-1}$. In some embodiments, the number average molecular weight of the PEA polymer is about 20.0 kg mol$^{-1}$.

In some embodiments, the PEA polymer is substantially water insoluble.

In some embodiments, the PEA polymer is soluble in water-miscible solvent, such as e.g. DMSO or DMF.

In some embodiments, theoretical molar percent of a monomer comprising hydrophobic aminoacid residue in PEA polymer is about 10, about 25, about 50, about 75, or about 90.

In some embodiments, actual molar percent of a monomer comprising hydrophobic aminoacid residue in PEA polymer is about 14, about 31, about 54, about 78, or about 94.

In some embodiments, theoretical molar percent of a monomer comprising L-Phe in PEA polymer is about 10, about 25, about 50, about 75, or about 90. In some embodiments, actual molar percent of a monomer comprising L-Phe in PEA polymer is about 14, about 31, about 54, about 78, or about 94.

In some embodiments, theoretical molar percent of a monomer comprising Ala in PEA polymer is about 10, about 25, about 50, about 75, or about 90.

Payload Molecules

The methods, particles, polymers and compositions described herein are useful for delivering a payload to a cell or an organism. In some embodiments, the payload is delivered to a biological target. The payload can be used, e.g., for labeling (e.g., a detectable agent such as a fluorophore), or for therapeutic purposes (e.g., insulin or other therapeutic molecule). In some embodiments, the payload is a conjugated biomolecule. In some embodiments, the biomolecule may be conjugated with an inorganic nanoparticle. In some embodiments, the biomolecule may be conjugated with a fluorophore. In some embodiments, the biomolecule may be conjugated with a small molecule therapeutic.

The proportion of the payload relative to the nanoparticle depends on the characteristics of the payload, the properties of the nanoparticle, and the application. In some embodiments, the payload is loaded in the range from about 0.01% by weight to about 99% by weight of the total weight of the nanoparticle. The payload can be in the range from about 1% by weight to about 80% by weight, from about 1% by weight to about 75% by weight, from about 1% by weight to about 70% by weight, from about 1% by weight to about 65% by weight, from about 1% by weight to about 60% by weight, from about 1% by weight to about 55% by weight, from about 1% by weight to about 50% by weight, from about 1% by weight to about 45% by weight, from about 1% by weight to about 40% by weight, from about 1% by weight to about 35% by weight, from about 1% by weight to about 30% by weight, from about 1% by weight to about 25% by weight, from about 1% by weight to about 20% by weight, from about 1% by weight to about 15% by weight, from about 1% by weight to about 10% by weight, and/or from about 1% by weight to about 5% by weight.

In some embodiments, the payload is about 1%, about 2%, about 3%, about 4%, about 5%, about 6%, about 7%, about 8%, about 8%, about 9%, or about 10%.

In some embodiments, the payload molecule is negatively charged, e.g. payload molecule comprises a functional group that is negatively charged at physiological pH, e.g., acids, including carboxylic acids (carboxylates), sulfonic acids (sulfonates), sulfates, and phosphonates.

Therapeutic Biomolecules

In some embodiments, the payload is a biomolecule. In some embodiments, the biomolecule is therapeutic. In some embodiments, biomolecules are organic molecules having a molecular weight of 200 daltons or more produced by living organisms or cells, including large polymeric molecules such as polypeptides, proteins, glycoproteins, polysaccharides, polynucleotides and nucleic acids, or analogs or derivatives of such molecules.

Therapeutic Proteins and Peptides

In some embodiments, the biomolecule is a therapeutic protein or peptide, such as an antibody, a hormone, a transmembrane protein, a growth factor, an enzyme, or a structural protein.

In some embodiments, therapeutic protein is a therapeutic peptide (e.g., containing 50 or fewer amino acids, 40 or fewer amino acids, 30 or fewer amino acids, 20 or fewer amino acids, or any number of amino acids that does not exceed 50). In some embodiments, therapeutic peptide is Cpd86, ZPGG-72, ZP3022, MOD-6030, ZP2929, HM12525A, VSR859, NN9926, TTP273/TTP054, ZYOG1, MAR709, TT401, HM11260C, PB1023, ZP1848, ZP4207, ZP2929, Dulaglutide, Semaglutide, or ITCA. In some embodiments, therapeutic peptide in any one of peptides described in Fosgerau et al. Drug Discovery Today, Volume 20, Issue 1, January 2015, Pages 122-128, Kaspar et al., Drug Discovery Today, Volume 18, Issues 17-18, September 2013, Pages 807-817, the disclosures of which are incorporated herein by reference in their entirety.

In some embodiments, the therapeutic peptide is negatively charged.

In some embodiments, the therapeutic protein is negatively charged, e.g., the therapeutic protein comprises a functional group that is negatively charged as physiological pH, e.g., acids, including carboxylic acids (carboxylates), sulfonic acids (sulfonates), sulfates, and phosphonates.

In some embodiments, the protein therapeutic is any one of protein therapeutics described in, e.g., Leader et al., *Nature Reviews* 2008, 7, 21-39, the disclosure of which is incorporated herein by reference in its entirety.

In some embodiments, the therapeutic protein is a cytokine, such as transforming growth factor-beta (TGF-beta), interferons (e.g., interferon-alpha, interferon-beta, interferon-gamma), colony stimulating factors (e.g., granulocyte colony stimulating factor (GM-CSF)), and thymic stromal lymphopoietin (TSLP).

In some embodiments, the interferon is interferon-αcon1, interferon-alpha2a, interferon-αa2b, interferon-αn3, interferon-β1a, or interferon-γ1b.

In some embodiments, the cytokine is an interleukin, such as interleukin-1, interleukin-2, interleukin-3, interleukin-4, interleukin-5, interleukin-6, interleukin-7, interleukin-8, interleukin-10, interleukin-12, interleukin-13, interleukin-15, interleukin-17, interleukin-18, interleukin-22, interleukin-23, and interleukin-35.

In some embodiments, the therapeutic protein is a polypeptide hormone, such as amylin, anti-Müllerian hormone, calcitonin, cholecystokinin, corticotropin, endothelin, enkephalin, erythropoietin (EPO), darbepoetin, follicle-stimulating hormone, gallanin, gastrin, ghrelin, glucagon, gonadotropin-releasing hormone, growth hormone-releasing hormone, hepcidin, human chorionic gonadotropin, growth hormone (GH), human growth hormone (hGH), inhibin, insulin, isophane insulin, insulin detemir, insulin glargine, pramlintide, pramlintide acetate, insulin-like growth factor, leptin, luteinizing hormone, luteinizing hormone releasing hormone, melanocyte stimulating hormone, motilin, orexin, oxytocin, pancreatic polypeptide, parathyroid hormone, prolactin, secretin, somatostatin, thrombopoietin, thyroid-stimulating hormone, vasoactive intestinal peptide, somatotropin, mecasermin, mecasermin rinfabate, human follicle-stimulating hormone, lutropin, teriparatide, exenatide, octreotide, dibotermin-α, bone morphogenetic protein 7, keratinocyte growth factor, platelet-derived growth factor, trypsin, nesiritide and vasopressin.

In some embodiments, the therapeutic protein is factor VIIa, factor VIII, factor IX, antithrombin III, protein C, drotrecogin-α, filgrastim, pegfilgrastim, sargramostim, Lepirudin, Bivalirudin, or oprelvekin.

In some embodiments, the therapeutic protein is botulinium toxin type A, botulinium toxin type B.

In some embodiments, the polypeptide hormone is useful in treating endocrine disorders (hormone deficiencies). In some embodiments, the polypeptide hormone is useful in treating haemostasis and thrombosis.

In some embodiments, the therapeutic protein is an enzyme. In some embodiments, the enzyme is agalsidase beta, imiglucerase, velaglucerase alfa, taliglucerase, alglucosidase alfa, laronidase, idursulfase, β-gluco-cerebrosidase, alglucosidase-α, laronidase, α-L-iduronidase, idursulphase, iduronate-2-sulphatase, galsulphase, agalsidase-β, human α-galactosidase A, α-1-proteinase, α-1-proteinase inhibitor, pancreatic enzyme, lactase, lipase, amylase, protease, adenosine deaminase, alteplase, reteplase, tenecteplase, urokinase, collagenase, human deoxyribonuclease I, dornase-α, hyaluronidase, papain, asparaginase (e.g. L-Asparaginase), rasburicase, streptokinase, anistreplase, or galsulfase.

In some embodiments, the enzyme is useful in treating metabolic enzyme deficiencies. In some embodiments, the enzyme is useful in treating pulmonary and gastrointestinal-tract disorders. In some embodiments, the enzyme is useful in treating immunodeficiencies.

In some embodiments, the therapeutic protein is albumin, human albumin, or immunoglobulin.

In some embodiments, the therapeutic protein is an antibody (e.g., monoclonal antibodies, e.g., bispecific monoclonal antibodies), including therapeutic antibodies. In some embodiments, the antibody is useful in treating cancer. In some embodiments, the antibody useful in treating cancer is abagovomab, adecatumumab, afutuzumab, alacizumab pegol, altumomab pentetate, amatuximab, anatumomab mafenatox, apolizumab, arcitumomab, bavituximab, bectumomab, belimumab, bevacizumab, bivatuzumab mertansine, blinatumomab, brentuximab vedotin, cantuzumab mertansine, cantuzumab ravtansine, capromab pendetide, cetuximab, citatuzumab bogatox, cixutumumab, clivatuzumab tetraxetan, dacetuzumab, demcizumab, detumomab, drozitumab, ecromeximab, eculizumab, elotuzumab, ensituximab, epratuzumab, etaracizumab, farletuzumab, figitumumab, flanvotumab, galiximab, gemtuzumab ozogamicin, girentuximab, ibritumomab tiuxetan, imgatuzumab, ipilimumab, labetuzumab, lexatumumab, lorvotuzumab mertansine, nimotuzumab, ofatumumab, oregovomab, panitumumab, pemtumomab, pertuzumab, tacatuzumab tetraxetan, tositumomab, trastuzumab, totumumab, or zalutumumab.

In some embodiments, the antibody is useful in treating an inflammatory disease or condition. In some embodiments, the antibody useful in treating an inflammatory disease or condition is adalimumab, alemtuzumab, atlizumab, basiliximab, canakinumab, certolizumab, certolizumab pegol, daclizumab, muromonab, efalizumab, fontolizumab, golimumab, infliximab, mepolizumab, natalizumab, omalizumab, ruplizumab, ustekinumab, visilizumab, zanolimumab, vedolizumab, belimumab, otelixizumab, teplizumab, rituximab, ofatumumab, ocrelizumab, epratuzumab, eculizumab, or briakinumab.

In some embodiments, the therapeutic protein in useful in treating infectious disease. In some embodiments, the therapeutic protein useful in treating infectious disease is enfuvirtide.

In some embodiments, the therapeutic protein is abciximab, pegvisomant, crotalidae polyvalent immune Fab, digoxin immune serum Fab, ranibizumab, or ordenileukin diftitox.

In some embodiments, the therapeutic protein is useful in treating endocrine disorders (hormone deficiencies). In some aspects of these embodiments, the therapeutic protein is useful in treating diabetes, diabetes mellitus, diabetic ketoacidosis, hyperkalaemia, hyperglycemia, growth failure due to GH deficiency or chronic renal insufficiency, Prader-Willi syndrome, Turner syndrome, AIDS wasting or cachexia with antiviral therapy, growth failure in children with GH gene deletion or severe primary IGF1 deficiency, postmenopausal osteoporosis, severe osteoporosis, type 2 diabetes resistant to treatment with metformin and a sulphonylurea, or acromegaly.

In some embodiments, the therapeutic protein is useful in treating haemostasis and thrombosis. In some aspects of these embodiments, the therapeutic protein is useful in treating haemophilia A, haemophilia B, hereditary AT-III deficiency in connection with surgical or obstetrical procedures or for thromboembolism, venous thrombosis and purpura fulminans in patients with severe hereditary protein C deficiency, pulmonary embolism, myocardial infarction, acute ischaemic stroke, occlusion of central venous access devices, acute myocardial infarction, haemorrhage in patients with haemophilia A or B and inhibitors to factor VIII or factor IX, severe sepsis with a high risk of death, heparin-induced thrombocytopaenia, blood-clotting risk in coronary angioplasty, acute evolving transmural myocardial infarction, deep vein thrombosis, arterial thrombosis, occlusion of arteriovenous cannula, and thrombolysis in patients with unstable angina.

In some embodiments, the therapeutic protein is useful in treating metabolic enzyme deficiencies. In some aspects of these embodiments, the therapeutic protein is useful in treating Gaucher's disease, Pompe disease, glycogen storage disease type II, Hurler and Hurler-Scheie forms of mucopolysaccharidosis I, mucopolysaccharidosis II, Hunter syndrome, mucopolysaccharidosis VI, or Fabry disease.

In some embodiments, the therapeutic protein is useful in treating pulmonary and gastrointestinal-tract disorders. In some aspects of these embodiments, the therapeutic protein is useful in treating congenital α-1-antitrypsin deficiency, gas, bloating, cramps and diarrhea due to inability to digest lactose, cystic fibrosis, chronic pancreatitis, pancreatic insufficiency, post-Billroth II gastric bypass surgery, pancreatic duct obstruction, steatorrhoea, poor digestion, gas, or bloating.

In some embodiments, the therapeutic protein is useful in treating immunodeficiencies. In some aspects of these embodiments, the therapeutic protein is useful in treating severe combined immunodeficiency disease due to adenosine deaminase deficiency or primary immunodeficiencies.

In some embodiments, the therapeutic protein is useful in treating haematopoiesis. In some aspects of these embodiments, the therapeutic protein is useful in treating anaemia, myleodysplasia, anaemia due to renal failure or chemotherapy, preoperative preparation, anaemia in patients with chronic renal insufficiency and chronic renal failure (+/− dialysis), neutropaenia, neutropaenia in AIDS or post-chemotherapy or bone marrow transplantation, severe chronic neutropaenia, leukopaenia, myeloid reconstitution post-bone-marrow transplantation, HIV/AIDS, thrombocytopaenia (especially after myelosuppressive chemotherapy).

In some embodiments, the therapeutic protein is useful in treating infertility. In some aspects of these embodiments, the therapeutic protein is useful in assisted reproduction and treating infertility with luteinizing hormone deficiency.

In some embodiments, the therapeutic protein is useful in immunoregulation. In some aspects of these embodiments, the therapeutic protein is useful in treating chronic hepatitis C infection, hairy cell leukemia, chronic myelogenous, leukemia, Kaposi's sarcoma, hepatitis B, melanoma, Kaposi's sarcoma, follicular lymphoma, hairy-cell leukemia, condylomata acuminata, hepatitis C, condylomata acuminata (genital warts, caused by human papillomavirus), multiple sclerosis, chronic granulomatous disease, severe osteopetrosis, metastatic renal cell cancer, or melanoma.

In some embodiments, the therapeutic protein is useful in treating diseases or conditions associated with growth regulation. In some aspects of these embodiments, the therapeutic protein is useful in treating acromegaly, symptomatic relief of VIP-secreting adenoma and metastatic carcinoid tumours, spinal fusion surgery, bone injury repair, tibial fracture nonunion, lumbar, spinal fusion, precocious puberty, severe oral mucositis in patients undergoing chemotherapy or debridement adjunct for diabetic ulcers.

In some embodiments, the therapeutic protein is useful in treating decubitus ulcer, varicose ulcer, debridement of eschar, dehiscent wound, sunburn, or acute decompensated congestive heart failure.

In some embodiments, the therapeutic protein is useful in enzymatic degradation of macromolecules. In some aspects of these embodiments, the therapeutic protein is useful in treating many types of dystonia (e.g., cervical), debridement of chronic dermal ulcers and severely burned areas, cystic fibrosis, respiratory tract infections, respiratory tract infections in selected patients with FVC greater than 40% of predicted, debridement of necrotic tissue, or debridement of necrotic tissue or liquefication of slough in acute and chronic lesions (e.g., pressure ulcers, varicose and diabetic ulcers, burns, postoperative wounds, pilonidal cyst wounds, carbuncles, and other wounds).

In some embodiments, the therapeutic protein is useful in treating cancer. In some aspects of these embodiments, the cancer is any one of cancers described herein.

In some embodiments, the therapeutic protein is useful in treating inflammatory disease or condition. In some aspects of these embodiments, the inflammatory disease or condition is any one diseases or conditions described herein (e.g. rheumatoid arthritis, Crohn's disease, psoriasis, and multiple sclerosis).

In some embodiments, the therapeutic protein is useful in organ transplantation (e.g. treating acute kidney transplant rejection).

In some embodiments, the therapeutic protein is useful in treating pulmonary disorders (e.g., respiratory syncytial virus infection, asthma).

In some embodiments, the therapeutic protein is useful in treating infectious disease. In some aspects of these embodiments, infectious disease is HIV infection.

Further examples of useful therapeutic proteins can be found in U.S. Pat. Nos. 8,349,910; and 8,043,833; U.S. patent applications 2013/0195888; and 2007/0092486; and PCT WO 2014/130064, each of which is hereby incorporated by reference in its entirety. In some embodiments, biomolecules can be sensitive to physiological environments, e.g., to physiologic enzymes or local pH, before delivery to the target tissue or target cell.

In some embodiments, the biomolecule is an antibody-drug conjugate. In some embodiments, the antibody-drug conjugate is trastuzumab-emtansine, brentuximab-vedotin, or T-DM1.

In some embodiments, the biomolecule is an antibody fragment-drug conjugates; protein-drug conjugates; peptide-drug conjugates (e.g., paclitaxel-Angiopep 2, BMTP-11 (Arrowhead Research), zoptarelin doxorubicin, and NGR-hTNF).

In some embodiments, the biomolecule is a fusion protein (i.e., a chimeric protein formed by the expression of two or more genes that encode for different proteins). In some embodiments the fusion protein is Fc fusion protein, which contain an antibody Fc unit that can offer stability or selective targeting of a cell or tissue type, including therapeutic proteins, such as atacicept, abatacept, aflibercept, alefacept, belatacept, etanercept, sotatercept, romiplostim, and rilonacept In some embodiments, the biomolecule is a bispecific fusion protein (i.e., bispecific antibodies), which comprise two arms from different antibodies, and are thereby able to target two different types of antigens, such as Ec-LDP-Hr-AE, MM-111 (Merrimack Pharmaceuticals), and IMCgp100 (Immunocore Ltd.).

In some embodiments, the biomolecule is a multimeric fusion protein, which is a fusion protein created by engineered multimerization (e.g., with streptavidin or using leucine zippers), such as polyvalent IgG2a Fc (M045).

Antigens and Adjuvants

In some embodiments of the present disclosure, the payload is an antigen.

In some embodiments, the antigen is hepatitis B surface antigen. In some embodiments, the antigen is strains 6, 11, 16, or 18 of HPV (Human papillomavirus). In some embodiments, the antigen is a capsid protein from HPV. In some embodiments, the antigen is OspA. In some embodiments, the antigen is lipoprotein on outer surface of Borrelia burgdorferi. In some embodiments, the antigen is Anti-Rhesus (Rh) immunoglobulin G. In some embodiments, the antigen is HIV antigen. In some embodiments, the antigen is hepatitis C antigen.

In some embodiments, the antigen is Influenza virus antigen. In some embodiments, the antigen is influenza B virus antigen. In some embodiments, the antigen is influenza A virus antigen.

In some embodiments, the antigen is poliovirus antigen.

In some embodiments, the antigen is a dust mite allergen. In some embodiments, the dust mite allergen is any one of dust mite allergens disclosed in, e.g., Stewart, *Clinical Reviews in Allergy and Immunology* 1995, 13, 135-150, the disclosure of which is incorporated herein by reference in its entirety.

In some embodiments, the antigen is a peptide. In some embodiments, the peptide is SIINFEKL (Ova257-264). In some embodiments, the antigen is palmitic acid conjugated to SIINFEKL peptide (C16-SIINFEKL).

In some embodiments of the present disclosure, when the payload is an antigen, the core of the particle optionally comprises an adjuvant as an additional payload. In some embodiments, adjuvant is as immunostimulatory agent. In some embodiments, the adjuvant is selected from the group consisting of resiquimod, imiquimod, gardiquimod, flagellin, monophosphoryl lipid A, N-glycolyted muramyldipeptide, CpG, R848 and Cholera toxin. In some embodiments, adjuvant is palmitic acid conjugated to R848 (C16-R848). In some embodiments, adjuvant is an inorganic compound. In some embodiments, adjuvant is alum, aluminum hydroxide, aluminum phosphate, or calcium phosphate hydroxide. In some embodiments, adjuvant is paraffin oil. In some embodiments, adjuvant is Bordetella pertussis, Mycobacterium bovis, or toxoids. In some embodiments, adjuvant is squalene, thimerosal, quil A, quillaja, soaybean, polygala senega, IL-1, IL-2, IL-12, Freund's complete adjuvant, Freund's incomplete adjuvant, Adjuvant 65. In some embodiments, adjuvant is a peanut oil based.

Small Molecule Drugs

Small molecule drugs are low molecular weight organic compounds (typically about 2000 daltons or less). In some embodiments, the molecular weight of the drug molecule is in the range from about 200 to about 2000, from about 200 to about 1800, from about 200 to about 1600, from about 200 to about 1400, from about 200 to about 1200, from about 200 to about 1000, from about 200 to about 800, from about 200 to about 600 daltons, from about 300 to about 2000, from about 300 to about 1800, from about 300 to about 1600, from about 300 to about 1400, from about 300 to about 1200, from about 300 to about 1000, from about 300 to about 800, and/or from about 300 to about 600 daltons.

The small molecule drugs can include negatively charged compounds, e.g. compounds that have a functional group that is negatively charged as physiological pH, e.g., acids, including carboxylic acids (carboxylates), sulfonic acids (sulfonates), sulfates, and phosphonates.

Examples of small molecule drugs include cytochalasin B, gramicidin D, ethidium bromide, emetine, mitomycin, etoposide, tenoposide, colchicin, daunorubicin, dihydroxy anthracin dione, mithramycin, actinomycin D, 1-dehydrotestosterone, glucocorticoids, procaine, tetracaine, lidocaine, amphotericin B, propranolol, puromycin, maytansinoids, e.g., maytansinol (see U.S. Pat. No. 5,208,020), CC-1065 (see U.S. Pat. Nos. 5,475,092, 5,585,499, 5,846, 545) and analogs or homologs thereof.

Other small molecule drugs include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), antifungal agents (e.g., butenafine, terbinafine, and naftifine), immunomodulating drugs (e.g., glatiramer acetate, fingolimod, teriflunomide, and dimethyl fumarate), and anti-mitotic agents (e.g., vincristine, vinblastine, paclitaxel, and maytansinoids).

Examples of suitable chemotherapeutic agents include any of: abarelix, aldesleukin, alitretinoin, allopurinol, altretamine, anastrozole, arsenic trioxide, asparaginase, azacitidine, bexarotene, bleomycin, bortezomib, busulfan, calusterone, capecitabine, carboplatin, carmustine, chlorambucil, cisplatin, cladribine, clofarabine, cyclophosphamide, cytarabine, dacarbazine, dactinomycin, dalteparin, dasatinib, daunorubicin, decitabine, denileukin, dexrazoxane, docetaxel, doxorubicin, dromostanolone, epirubicin, erlotinib, estramustine, etoposide, exemestane, filgrastim, floxuridine, fludarabine, fluorouracil, fulvestrant, gefitinib, gemcitabine, goserelin acetate, histrelin acetate, idarubicin, ifosfamide, imatinib, irinotecan, lapatinib ditosylate, lenalidomide, letrozole, leucovorin, leuprolide, levamisole, lomustine, mechlorethamine, megestrol, melphalan, mercaptopurine, methotrexate, methoxsalen, mitomycin C, mitotane, mitoxantrone, nandrolone, nelarabine, nofetumomab, oxaliplatin, paclitaxel, pamidronate, pegaspargase, pegfilgrastim, pemetrexed, pentostatin, pipobroman, plicamycin, procarbazine, quinacrine, rasburicase, ruxolitinib, sorafenib, streptozocin, sunitinib, tamoxifen, temozolomide, teniposide, testolactone, thalidomide, thioguanine, thiotepa, topotecan, toremifene, tretinoin, uracil mustard, valrubicin, vinblastine, vincristine, vinorelbine, vorinostat, and zoledronate, or a pharmaceutically acceptable salt thereof. In some embodiments, the payload is docetaxel.

Small molecules useful in the compositions and methods described herein bind with high affinity to a biopolymer, such as protein, nucleic acid, or polysaccharide, or other biological target. Other examples include small molecules that bind specifically to receptors for hormones, such as steroid hormones (e.g., dihydrotestosterone and estradiol), melatonin, dopamine, or other signaling molecules, that may be delivered as described herein.

Polynucleotides and Nucleic Acids

In some embodiments, payload is a polynucleotide or a nucleic acid, such as, e.g., RNA (e.g., mRNA, microRNA, siRNA, or shRNA) or DNA (e.g., cDNA).

The nucleic acid may be double-stranded (e.g., double-stranded DNA) or single-stranded (e.g., single-stranded RNA). The nucleic acid can comprise a vector (e.g., a plasmid or a viral vector, e.g., one derived from a retrovirus, a lentivirus, an adenovirus, or an adeno-associated virus). In some embodiments, the nucleic acid can reduce expression of a protein (e.g., a protein associated with a disease state, e.g., a kinase upregulated in a cancer, such as BRAF-mutated melanoma). In some embodiments, the nucleic acid can introduce or enhance expression of a protein (e.g., to encode for a protein that is depleted in a disease state, e.g., normal CFTR protein to treat cystic fibrosis).

In some embodiments, the siRNA is siMYC (i.e., anti-MYC siRNA). In some embodiments, the siRNA is si-c-MYC (i.e., anti-c-MYC siRNA). In some embodiments, the siRNA is siBRAF (i.e., anti-BRAF siRNA). In some embodiments, the siRNA is siBRAF$^{V600E}$ (i.e., anti-BRAF$^{V600E}$ siRNA).

In some embodiments, polynucleotide (e.g., siRNA, miR, mRNA) may target the expression and/or activity of one or more proteins (e.g., an enzyme, e.g., a kinase) associated with cancer In some embodiments, the polynucleotide can target a protein selected from the group consisting of: kinesin spindle protein (KSP), RRM2, keratin 6a (K6a), HER1, ErbB2, a vascular endothelial growth factor (VEGF) (e.g., VEGFR1, VEGFR3), a platelet-derived growth factor receptor (PDGFR) (e.g., PDGFR-α, PDGFR-β), epidermal growth factor receptor (EGFR), a fibroblast growth factor receptor (FGFR) (e.g., FGFR1, FGFR2, FGFR3, FGFR4), EphA2, EphA3, EphA4, HER2, HER3, HER4, INS-R, IGF-1R, IR-R, CSF1R, KIT, FLK-II, KDR/FLK-1, FLK-4, flt-1, c-Met, Ron, Sea, TRKA, TRKB, TRKC, FLT3, VEGFR/Flt2, Flt4, EphA1, EphB2, EphB4, Pim1, Pim2, Pim3, Tie2PKN3, PLK1, PLK2, PLK3, Src, Fyn, Lck, Fgr, Btk, Fak, SYK, FRK, JAK, Abl, Kit, KDR, CaM-kinase, phosphorylase kinase, MEKK, ERK, mitogen activated protein (MAP) kinase, phosphatidylinositol-3-kinase (PI3K), an AKT (e.g., Akt1, Akt2, Akt3), TGF-βR, KRAS, BRAF, a cyclin-dependent kinase (e.g., CDK1, CDK2, CDK4, CDK5, CDK6, CDK7, and CDK9), GSK3, a CDC-like kinase (CLK) (e.g., CLK1, CLK4), an Aurora kinase (e.g., Aurora A, Aurora B, and Aurora C), a mitogen-activated protein kinase kinase (MEK) (e.g., MEK1, MEK2), mTOR, protein kinase A (PKA), protein kinase C (PKC), protein kinase G (PKG), and PHB1.

Targeting Ligands

The present disclosure provides, inter alia, a targeting ligand that binds or reacts selectively with a receptor on the outside surface of a cell, wherein the targeting ligand may be selectively accumulated at the surface layer of a particle.

In some embodiments, the targeting ligand promotes transcytosis or endocytosis of the particle. In some embodiments, endocytosis is a caveolae-mediated endocytosis or a clathrin-mediated endocytosis. In some embodiments, the targeting ligand selectively binds to a transferrin receptor. In some embodiments, the targeting ligand is clathrin. In some embodiments, the targeting ligand is caveolin. In some embodiments, the targeting ligand is transferrin. In some embodiments, the targeting ligand is human transferrin.

In some embodiments, the targeting ligand is a fragment of transferrin. In some embodiments the fragment of transferrin is a transferrin polypeptide or peptide. In some embodiments, the fragment of transferrin retains the ability to bind to the transferrin receptor.

Transferrin receptor is a disulfide-linked homodimeric glycoprotein. Transferrin receptor is highly expressed at the cell surface of many tumor cells.

In some embodiments, human transferrin (Tf-h) consists of a single polypeptide chain with 698 amino acid residues and a molecular weight of approximately 80 kDa. In some embodiments, the targeting ligand is apo-transferrin, monoferric transferrin, or diferric transferrin. In some embodiments, transferrin does not comprise iron. In some embodiments, the targeting ligand is a transferrin fragment with 50 to 56 amino acids. In some embodiments, the fragment of transferrin is about 10 amino acids, about 20 amino acids, about 30 amino acids, about 50 amino acids, about 100 amino acids, about 200 amino acids, about 500 amino acids, or about 600 amino acids in length or more.

In some embodiments, the targeting ligand is an antibody, e.g., monoclonal antibody, e.g., a bispecific monoclonal antibody. The antibody can be a therapeutic antibody.

In some embodiments, the targeting ligand is an antibody and the antibody is abagovomab, adecatumumab, afutuzumab, alacizumab pegol, altumomab pentetate, amatuximab, anatumomab mafenatox, apolizumab, arcitumomab, bavituximab, bectumomab, belimumab, bevacizumab, bivatuzumab mertansine, blinatumomab, brentuximab vedotin, cantuzumab mertansine, cantuzumab ravtansine, capromab pendetide, cetuximab, citatuzumab bogatox, cixutumumab, clivatuzumab tetraxetan, dacetuzumab, demcizumab, detumomab, drozitumab, ecromeximab, eculizumab, elotuzumab, ensituximab, epratuzumab, etaracizumab, farletuzumab, figitumumab, flanvotumab, galiximab, gemtuzumab ozogamicin, girentuximab, ibritumomab tiuxetan, imgatuzumab, ipilimumab, labetuzumab, lexatumumab, lorvotuzumab mertansine, nimotuzumab, ofatumumab, oregovomab, panitumumab, pemtumomab, pertuzumab, tacatuzumab tetraxetan, tositumomab, trastuzumab, totumumab, or zalutumumab.

In some embodiments, the targeting ligand is an antibody and the antibody is adalimumab, alemtuzumab, atlizumab, basiliximab, canakinumab, certolizumab, certolizumab pegol, daclizumab, muromonab, efalizumab, fontolizumab, golimumab, infliximab, mepolizumab, natalizumab, omalizumab, ruplizumab, ustekinumab, visilizumab, zanolimumab, vedolizumab, belimumab, otelixizumab, teplizumab, rituximab, ofatumumab, ocrelizumab, epratuzumab, eculizumab, or briakinumab.

In some embodiments, the targeting ligand is a peptide. In some embodiments, the peptide is EGF, CANF, or Angiopep-2. In some embodiments, the targeting ligand is RGD peptide.

In some embodiments, the surface layer of a particle of the present disclosure comprises one or more targeting ligands (e.g., one targeting ligand, two targeting ligands, three targeting ligands, etc.)

In some embodiments, targeting ligand may be any one of biomolecules described herein.

Compositions

The present application also provides, inter alia, a composition comprising a particle described herein. The composition can be a pharmaceutical composition in which the particle is included together with a pharmaceutically acceptable carrier.

In some embodiments, when the payload is any one of antigens described herein, the composition comprises any one of adjuvants as described hetein.

The compositions of the disclosure offer the ability to deliver biomolecules, for example, therapeutically useful proteins, that may be sensitive to organic solvents without exposure to the solvents which are needed in other preparations. Such compositions retain a high bioactivity of the biomolecule compared with the native form but with an enhanced stability. In some embodiments, the bioactivity of the biomolecule in the composition is in a range from about 70% to about 100%, from about 80% to about 100%, or from about 90% to about 100% of the bioactivity of a native biomolecule. In some embodiments, the bioactivity of the biomolecule in the composition is about 90%, about 95%, about 97%, or greater than 99% of the bioactivity of a native biomolecule. Thus, in some aspects there are provided compositions as described herein comprising a nanoparticle comprising a core and a surface layer comprising a polymer surrounding the core; and a biomolecule selectively encapsulated in the core of the nanoparticle, wherein the bioactivity of the biomolecule in the composition is in a range from about 70% to about 100%, from about 80% to about 100%, or from about 90% to about 100% of the bioactivity of a native biomolecule, or wherein the bioactivity of the biomolecule in the composition is about 90%, about 95%, about 97%, or greater than 99% of the bioactivity of a native biomolecule.

The compositions of the disclosure can provide for controlled release or sustained release of a biomolecule in a biological system, e.g., when a biomolecule is delivered to a subject in need of therapy. Controlled release refers to delivery of an agent at a controlled rate for an extended time or in response to a stimulus (e.g., upon a change in pH or temperature, or in the presence of an enzyme). Controlled release of a biomolecule can provide a well-characterized and reproducible dosage form. Sustained release refers to the release of an agent over an extended period of time. In sustained release, the rate and duration of biomolecule release can be controlled to achieve a particular profile. A sustained release profile can include zero-order release, exponential decay, step-function release, or other release profiles that carry over a period of time, e.g., one to several hours (e.g., about 8 hours or 24 hours), one to several days (e.g., about 2, 3, 4, 5, 6, 7, 10, or 14 days), one to several weeks (e.g., about 2, 3, or 4 weeks) or one to several months (e.g., about 2, 3, 4, 5, or 6 months). The terms "zero-order release", "exponential decay" and "step-function release" as well as other sustained release profiles are well known in the art.

The controlled release profiles can afford enhanced pharmacokinetic profiles of a biomolecule within a subject, compared with a biomolecule in a subject that has not been loaded into a TNP. An enhanced pharmacokinetic profile can exhibit an improved property of one or more selected from AUC, half-life, clearance, mean residence time, and volume of distribution (Vss). In some embodiments, the AUC of a biomolecule in a composition of the disclosure is in a range from about 100% to about 1000%, from about 150% to about 700%, or from about 200% to about 500% of the AUC of a native biomolecule, or wherein the AUC of the biomolecule in the composition is about 150%, about 200%, about 250%, about 300%, about 350%, about 400%, about 450%, about 500%, or greater than 500% of the AUC of a native biomolecule. In some embodiments, the half-life of a biomolecule in a composition of the disclosure is in a range of from about 100% to about 100,000%, from about 100% to about 1000%, from about 100% to about 500%, from about 150% to about 400%, or from about 200% to about 300% of the half-life of a native biomolecule, or wherein the half-life of the biomolecule in the composition is about 150%, about 200%, about 250%, about 300%, or greater than 400% of the half-life of a native biomolecule. In some embodiments, the clearance of a biomolecule in a composition of the disclosure is in a range from about 1% to about 100%, from about 10% to about 90%, from about 20% to about 80%, from about 30% to about 70%, or from about 40% to about 80% of the clearance of a native biomolecule, or wherein the clearance of the biomolecule in the composition is about 3%, about 5%, about 10%, about 15%, about 20%, about 25%, about 30%, about 40%, about 50%, about 60%, about 70%, or about 80% of the clearance of a native biomolecule. In some embodiments, the mean residence time of a biomolecule in a composition of the disclosure is in a range from about 100% to about 1000%, from about 150% to about 700%, or from about 200% to about 500% of the mean residence time of a native biomolecule, or wherein the mean residence time of the biomolecule in the composition is about 150%, about 200%, about 250%, about 300%, about 350%, about 400%, about 450%, about 500%, or greater than 500% of the mean residence time of a native biomolecule.

As used herein, "substantially free of organic solvents" refers to compositions which are mostly or entirely free of organic solvents. For example, an aqueous mixture substantially free of organic solvents is an aqueous mixture which has been subjected to processes that have removed most or all organic solvents from the mixture. In some embodiments, a composition substantially free of organic solvents can comprise about 5% or less, about 2% or less, about 1% or less, about 0.5% or less, 0.1% or less 0.05% or less, or about 0.01% or less by weight of organic solvents. In some embodiments, a composition substantially free of organic solvents can comprise about 5%, about 2%, about 1%, 0.5%, about 0.1%, about 0.05%, or about 0.01% organic solvents. In some embodiments, a composition substantially free of organic solvents can comprise aqueous solutions comprising a pharmaceutically acceptable buffer. In some embodiments, a composition substantially free of organic solvents can comprise aqueous solutions comprising a pharmaceutically acceptable salt. Common pharmaceutically acceptable buffers include acetate (acetic acid and sodium acetate), citrate (citric acid and sodium citrate), and phosphate (sodium phosphate and disodium phosphate) buffers. Pharmaceutically acceptable salt solutions include dilute saline solutions. For example, the composition can be in a pH-buffered phosphate solution or a saline solution. In some embodiments, a composition substantially free of organic solvents is a composition in water. In some embodiments, a composition substantially free of organic solvents can be free of salts.

The present application also provides pharmaceutical compositions comprising a particle comprising an effective amount of a payload molecule, and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

If required, the solubility and bioavailability of the payload molecules of the present application in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of the present application optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the present application include those suitable for oral, rectal, nasal, topical (including buccal and sublingual), vaginal or parenteral (including subcutaneous, intramuscular, intravenous and intradermal) administration. Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, a particle comprising a payload molecule is administered orally. Compositions of the present application suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

The pharmaceutical compositions of the present application may be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g., U.S. Pat. No. 6,803,031.

Topical administration of the pharmaceutical compositions of the present application is especially useful when the desired treatment involves areas or organs readily accessible by topical application.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form.

In some embodiments, the topical composition comprises a combination of a particle comprising a payload molecule, and one or more additional ingredients, carriers, excipients, or diluents including, but not limited to, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

Lists of ingredients, which are well known in the art, are disclosed, for example, in "Cosmetics: Science and Technology," edited by M. S. Balsam and E. Sagarin, 2nd Edition, 1972, Wiley Pub. Co.; "The Chemistry and Manufacture of Cosmetics" by M. G. DeNavasse; and "Harry's Cosmeticology," J. B. Wilkinson et al., 7th Edition, 1982, Chem. Pub. Co.; the disclosures of each of the above being incorporated herein by reference in their entirety. In some embodiments, diluents, carriers, and excipients may include, but are not limited to, polyethylene glycols (such as PEG200, PEG300, PEG400, PEG540, PEG600, PEG1450 or mixtures thereof) and coconut oils (such as propylene glycol dicaprate, coco-caprylate/caprate, propylene glycol dicaprylate/dicaprate, caprylic/capric triglyceride, caprylic/capric/lauric triglyceride, caprylic/capric/linoleic triglyceride, tricaprin, tricaprylin, glyceryl trioleate, neopentyl glycol dicaprylate/dicaprate, caprylic/capric/palmitic/stearic triglceride, or mixtures thereof). In some embodiments, suitable carriers include, but are not limited to, mineral oil, sorbitan monostearate, polysorbate 60, cetyl esters wax, cetearyl alcohol, 2-octyldodecanol, benzyl alcohol, and water. In some embodiments, preservatives may include, but are not limited to, 1,2-hexanediol, benzoic acid, benzothonium chloride, borax, bronopol, butylparaben, caprylyl glycol, chlorophene, chloroxylenol, chlorphenesin, dehydroacetic acid, diazolidinyl urea, DMDM hydantoin, ethylhexylglycerin, ethylparaben, formaldehyde-releasing preservative, Germaben II, hoelen, imidazolidinyl urea, iodopropynyl butylcarbamate, isobutylparaben, methylchloroisothiazolinone, methyldibromo glutaronitrile, Methylisothiazolinone, methylparaben, o-cymen-5-ol, phenoxyethanol, phenoxyisopropanol, phytosphingosine, polyaminopropyl biguanide, potassium sorbate, propylparaben, quaternium-15, sodium benzoate, sodium citrate, sodium dehydroacetate, sodium hexametaphosphate, sodium hydroxymethylglycinate, sodium lactobionate, sodium metabisulfite, sodium sulfite, sorbic acid, and styrax benzoin. In some embodiments, slip agents may include, but are not limited to, amodimethicone, bis-PEG-18 methyl ether dimethyl silane, bis-phenylpropyl dimethicone, butylene glycol, cetyl dimethicone, cetyl dimethicone copolyol, cetyl PEG/PPG-10/1-dimethicone, cyclohexasiloxane, cyclomethicone, cyclopentasiloxane, cyclotetrasiloxane, decylene glycol, diisostearoyl trimethylolpropane siloxy silicate, dimethicone, dimethicone copolyol, dimethicone crosspolymer, dimethiconol, dipropylene glycol, hexylene glycol, hydrolyzed silk, isododecane, methicone, methyl trimethicone, methylsilanol mannuronate, methylsilanol PEG-7 glyceryl cocoate, PEG-10 dimethicone, PEG-10 dimethicone/vinyl dimethicone crosspolymer, PEG-12 dimethicone, PEG/PPG-18/18 dimethicone, PEG/PPG-20/15 dimethicone, pentylene glycol, phenyl trimethicone, polymethylsilsesquioxane, PPG-3 benzyl ether myristate, silica dimethyl silylate, silk powder, siloxane, simethicone, sorbitol, stearyl dimethicone, stearyl methicone, triethoxycaprylylsilane, trimethylsiloxysilicate, xylitol, and zinc stearate. In some embodiments, sunscreen actives may include, but are not limited to, avobenzone, benzephenone-3, benzophenones, bumetrizole, butyl methoxydibenzoylmethane, ecamsule, ensulizole, ethylhexyl methoxycinnamate, homosalate, menthyl anthranilate, meradmiate, Mexoryl SX, octinoxate, octisalate, octocrylene, octyl methoxycinnamate, octyl salicylate, oxybenzone, padimate O, para-aminobenzoic acid (PABA), Parsol 1789, terephthalylidine dicamphor sulfonic acid, Tinosorb M, Tinosorb S, and titanium dioxide. In some embodiments, emulsifiers, surfactants, and detergents may include, but are not limited to, ammonium laureth sulfate, ammonium lauryl sulfate, arachidyl glucoside, behenic acid, bis-PEG-18 methyl ether dimethyl silane, $C_{20-40}$ pareth-40, cocamidopropyl betaine, cocamidopropyl dimethylamine, cocamidopropyl hydroxysultaine, coco-glucoside, coconut oil, decyl glucoside, dicetyl phosphate, dihydrocholeth-30, disodium cocoamphodiacetate, disodium cocoyl glutamate, disodium lauraminopropionate, glyceryl behanate, hydrogenated vegetable glycerides citrate, isohexadecane, isostearamide DEA, lauramphocarboxyglycinate, laureth-23, laureth-4, laureth-7, lauryl PEG-9 polydimethylsiloxyethyl dimethicone, lauryl alcohol, lauryl glucoside, magnesium laureth sulfate, magnesium oleth sulfate, myristic acid, nonoxynols, oleic acid, oleth 10, palm kernel acid, palmitic acid, PEG-60 almond glycerides, PEG-75 shea butter glycerides, PEG 90M, PEG-10 dimethicone, PEG-10 dimethicone/vinyl dimethicone crosspolymer, PEG-10 rapeseed sterol, PEG-100 stearate, PEG-12 dimethicone, PEG-120 methyl glucose dioleate, PEG-20 methyl glucose sesquistearate, PEG-40 stearate, PEG-60 hydrogenated castor oil, PEG-7 glyceryl cocoate, PEG-8, PEG-80 sorbitan laurate, PEG/PPG-17/6 copolymer (polyethylene glycol/polypropylene glycol-17/6 copolymer), PEG/PPG-18/18 dimethicone, PEG/PPG-20/15 dimethicone, poloxamer 184, Poloxamer 407, poloxamers, polyglyceryl-3 beeswax, polyglyceryl-4 isostearate, polyglyceryl-6 isostearate, polysorbate 20, polysorbate 60, polysorbate 80, potassium cetyl phosphate, potassium hydroxide, potassium myristate, PPG-12 buteth-16, PPG-26-Buteth-26, Salvia officinalis, Saponaria officinalis extract, soapwort, sodium $C_{14-16}$ olefin sulfonate, sodium cetearyl sulfate, sodium cocoamphoacetate, sodium cocoate, sodium cocoyl glutamate, sodium cocoyl isethionate, sodium dilauramidoglutamide lysine, sodium hexametaphosphate, sodium hydroxide, sodium laureth sulfate, sodium laureth-13 carboxylate, sodium lauroamphoacetate, sodium lauroyl lactylate, sodium lauroyl sarcosinate, sodium lauryl glucose carboxylate, sodium lauryl sulfate, sodium methyl cocoyl taurate, sodium methyl taurate, sodium myreth sulfate, sodium palm kernelate, sodium palmate, sodium PEG-7 olive oil carboxylate, sodium trideceth sulfate, steareth-20, TEA-lauryl sulfate (triethanolamine-lauryl sulfate), and tribehenin PEG-20 esters.

In the pharmaceutical compositions of the present application, a particle comprising a payload molecule is present in an effective amount (e.g., a therapeutically effective amount).

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In some embodiments, an effective amount of a particle comprising a payload molecule can range, for example, from about 1 mg to about 200 mg, from about 1 to about 100 mg, from about 1 to about 50 mg, from about 1 mg to about 30 mg, from about 1 mg to about 15 mg, from about 10 mg to about 2000 mg, from about 10 mg to about 1900 mg, from about 10 mg to about 1800 mg, from about 10 mg to about 1700 mg, from about 10 mg to about 1600 mg, from about 10 mg to about 1500 mg, from about 10 mg mg to about 1400 mg, from about 10 mg to about 1300 mg, from about 10 mg to about 1200 mg, from about 10 mg to about 1100 mg, from about 10 mg to about 1000 mg, from 10 mg about to about 900 mg, from about 10 mg to about 800 mg, from about 10 mg to about 700 mg, from about 10 mg to about 600 mg, from about 10 mg to about 500 mg, from about 10 mg to about 400 mg, from about 10 mg to about 300 mg, from about 10 mg to about 200 mg, from about 10 mg to about 100 mg, and from about 10 mg to about 50 mg. In some aspects of these embodiments, the composition containing an effective amount of a particle comprising a payload molecule is administered once daily. In some aspects of these embodiments, the composition containing an effective amount of a particle comprising a payload molecule is administered twice daily. In some aspects of these embodiments, the composition containing an effective amount of a particle comprising a payload molecule is administered thrice daily.

In some embodiments, an effective amount of a particle comprising a payload molecule can range, for example, from about 0.01 mg/kg to about 0.5 mg/kg, from about 0.01 mg/kg to about 0.4 mg/kg, from about 0.01 mg/kg to about 0.3 mg/kg, from about 0.01 mg/kg to about 0.2 mg/kg, from about 0.01 mg/kg to about 0.1 mg/kg, from about 0.1 mg/kg to about 0.5 mg/kg, from about 0.2 mg/kg to about 0.5 mg/kg, from about 1 mg/kg to about 500 mg/kg, from about 1 mg/kg to about 200 mg/kg, from about 1 mg/kg to about 100 mg/kg, from about 1 mg/kg to about 50 mg/kg, from about 1 mg/kg to about 40 mg/kg, from about 1 mg/kg to about 30 mg/kg, from about 1 mg/kg to about 20 mg/kg, from about 1 mg/kg to about 10 mg/kg, from about 2 mg/kg to about 400 mg/kg, from about 3 mg/kg to about 300 mg/kg, from about 4 mg/kg to about 200 mg/kg, from about 5 mg/kg to about 100 mg/kg, from about 10 mg/kg to about 500 mg/kg, from about 10 mg/kg to about 400 mg/kg, from about 10 mg/kg to about 300 mg/kg, from about 10 mg/kg to about 200 mg/kg, from about 10 mg/kg to about 100 mg/kg, and from about 10 mg/kg to about 50 mg/kg In some embodiments, an effective amount of a particle comprising a payload molecule can be, for example, 0.01 mg/kg, 0.02 mg/kg, 0.03 mg/kg, 0.05 mg/kg, 0.1 mg/kg, 0.2 mg/kg, 0.3 mg/kg, 0.5 mg/kg, 1 mg/kg, 5 mg/kg, 10 mg/kg, 20 mg/kg, 30 mg/kg, 40 mg/kg, 50 mg/kg, or 100 mg/kg.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

Methods of Making

The Particle

This disclosure provides preparation of the particles as described herein using robust self-assembly precipitation method.

This disclosure provides a method of preparing a particle described herein, the method comprising: (i) obtaining a first solution of the polymer that comprises a positively charged component and a hydrophobic component in a water-miscible solvent; (ii) obtaining a second aqueous solution comprising the targeting ligand that binds or reacts selectively with a receptor on the outside surface of a cell; and (iii) mixing the first solution with the second aqueous solution to form an aqueous suspension comprising a particle.

In some embodiments, the method is a self-assembly one-step nanoprecipitation method.

In some embodiments, the method of preparing particles as provided herein can avoid use of detergents, sonication, or other harsh formulation techniques, and thus offers a simple and convenient synthetic approach which may be amenable to clinical use.

In some embodiments, the water-miscible solvent is an alcohol. In some aspects of these embodiments, the water-miscible solvent is ethanol, methanol, 1-propanol, 1,3-propanediol, 1,5-pentanediol, 2-propanol, propylene glycol, 1,2-butandiol, 1,3-butandiol, 1,4-butandiol, 2-butoxyethanol, furfuryl alcohol or glycerol.

In some embodiments, the water-miscible solvent is acetaldehyde, acetic acid, acetone, acetonitrile, butyric acid, diethanolamine, diethylenetriamine, dimethylformamide (DMF), dimethoxyethane, dimethyl sulfoxide (DMSO), 1,4-dioxane, ethylamine, formic acid, methyl diethanolamine, propanoic acid, pyridine, tetrahydrofuran or triethyleneglycol. In some embodiments, the water-miscible solvent is dimethyl sulfoxide (DMSO).

In some embodiments, concentration of the polymer that comprises a positively charged component and a hydrophobic component in a water-miscible solvent is from about 0.1 mg/mL to about 100 mg/mL, from about 1 mg/mL to about 90 mg/mL, from about 2 mg/mL to about 80 mg/mL, from about 3 mg/mL to about 70 mg/mL, from about 4 mg/mL to about 60 mg/mL, from about 5 mg/mL to about 50 mg/mL, from about 6 mg/mL to about 40 mg/mL, from about 7 mg/mL to about 30 mg/mL, from about 8 mg/mL to about 20 mg/mL, from about 9 mg/mL to about 12 mg/mL. In some embodiments, the concentration of the polymer that comprises a positively charged component and a hydrophobic component in a water-miscible solvent is about 7 mg/mL, about 8 mg/mL, about 9 mg/mL, or about 10 mg/mL. In some embodiments, the concentration of the polymer that comprises a positively charged component and a hydrophobic component in a water-miscible solvent is about 10 mg/mL.

In some embodiments, the first solution may further comprises a payload. In some embodiments, the payload is any one of payloads described herein. In some embodiments, the payload is a therapeutic protein. In some embodiments, the therapeutic protein is insulin. In some embodiments, the payload molecule is an antigen. In some embodiments, the antigen is a dust mite allergen.

In some embodiments, concentration of the payload in a water-miscible solvent is about 0.1 mg/mL, about 0.5 mg/mL, about 0.75 mg/mL, about 1 mg/mL, about 1.25 mg/mL, about 1.75 mg/mL, about 2 mg/mL, about 3 mg/mL, about 5 mg/mL, or about 10 mg/mL. In some embodiments, concentration of the payload in a water-miscible solvent is about 1 mg/mL.

In some embodiments, the method comprises obtaining a second aqueous solution comprising targeting ligand that binds or reacts selectively with a receptor on the outside surface of a cell.

In some embodiments, concentration of the targeting ligand in the second aqueous solution is about 0.01 mg/mL, about 0.05 mg/mL, about 0.1 mg/mL, about 0.5 mg/mL, about 1 mg/mL, about 2 mg/mL, about 5 mg/mL, or about 10 mg/mL. In some embodiments, concentration of the targeting ligand is about 0.1 mg/mL.

In some embodiments, the second aqueous solution comprises one or more targeting ligands (e.g., one targeting ligand, two targeting ligands, three targeting ligands, etc.)

In some embodiments, the targeting ligand selectively binds with a receptor that promotes transcytosis or endocytosis of the particle. In some embodiments, the targeting ligand is transferrin.

In some embodiments, the method comprises mixing the first solution with the second aqueous solution to form an aqueous suspension comprising a particle.

In some embodiments, the mixing comprises addition of the first solution to the second aqueous solution. In some embodiments, the addition is dropwise. In some embodiments, the addition is portionwise.

In some embodiments, the mixing comprises addition of second aqueous solution to the first solution. In some embodiments, the addition is dropwise. In some embodiments, the addition is portionwise.

In some embodiments, the mixing comprises simultaneous combining of the first solution and the second solution.

In some embodiments, the mixing is carried out at room temperature. In some embodiments, the mixing is carried out a temperature in the range from about 0° C. to about 60° C., from about 2° C. to about 50° C., from about 5° C. to about 40° C., from about 10° C. to about 30° C., or from about 15° C. to about 25° C. In some embodiments, mixing is carried out at 18° C.

In some embodiments, the method further comprises stirring the aqueous suspension comprising the particle. In some embodiments, the stirring is carried out for 15 min. at room temperature to maximize the surface protein capture.

In some embodiments, the particle is formed instantly upon mixing.

In some embodiments, the payload is selectively encapsulated within the core of the particle. In some embodiments, the targeting ligand is selectively accumulated in the surface layer of the particle. In some embodiments, the payload is selectively encapsulated within the core of the particle and the targeting ligand is selectively accumulated in the surface layer of the particle.

In some embodiments, the particle may be prepared as described in Example 2. In some embodiments, the particle may be prepared as described in FIG. 1A. In some embodiments, the particle may be prepared without the payload. In some embodiments, the particle may be prepared with a payload. In some embodiments, the particle is a nanoparticle.

The PEA Polymer

Figure 5:
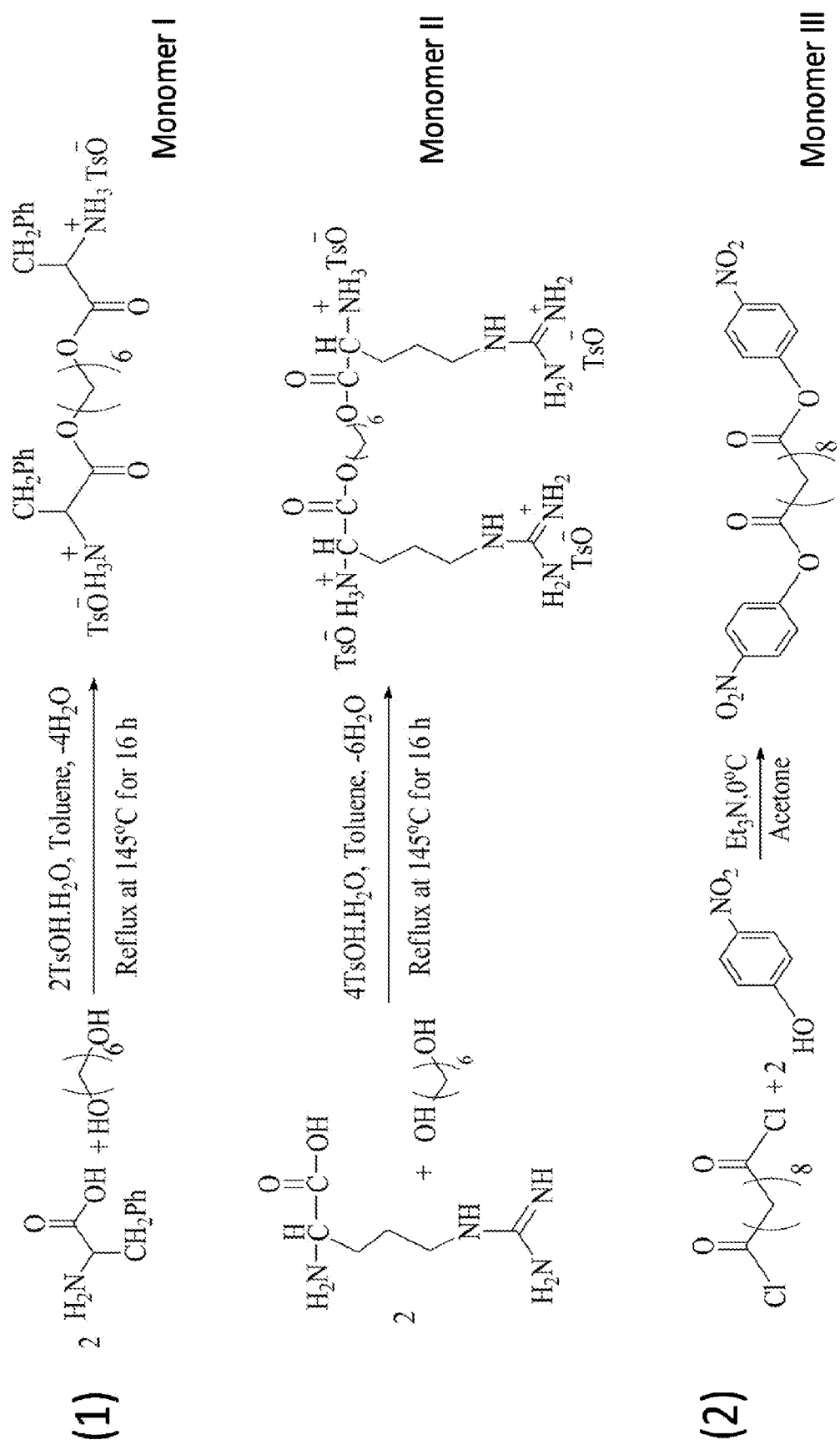
FIG. 5 contains schemes showing synthesis procedures for preparation of monomers and PEA polymer.
Figure 5:
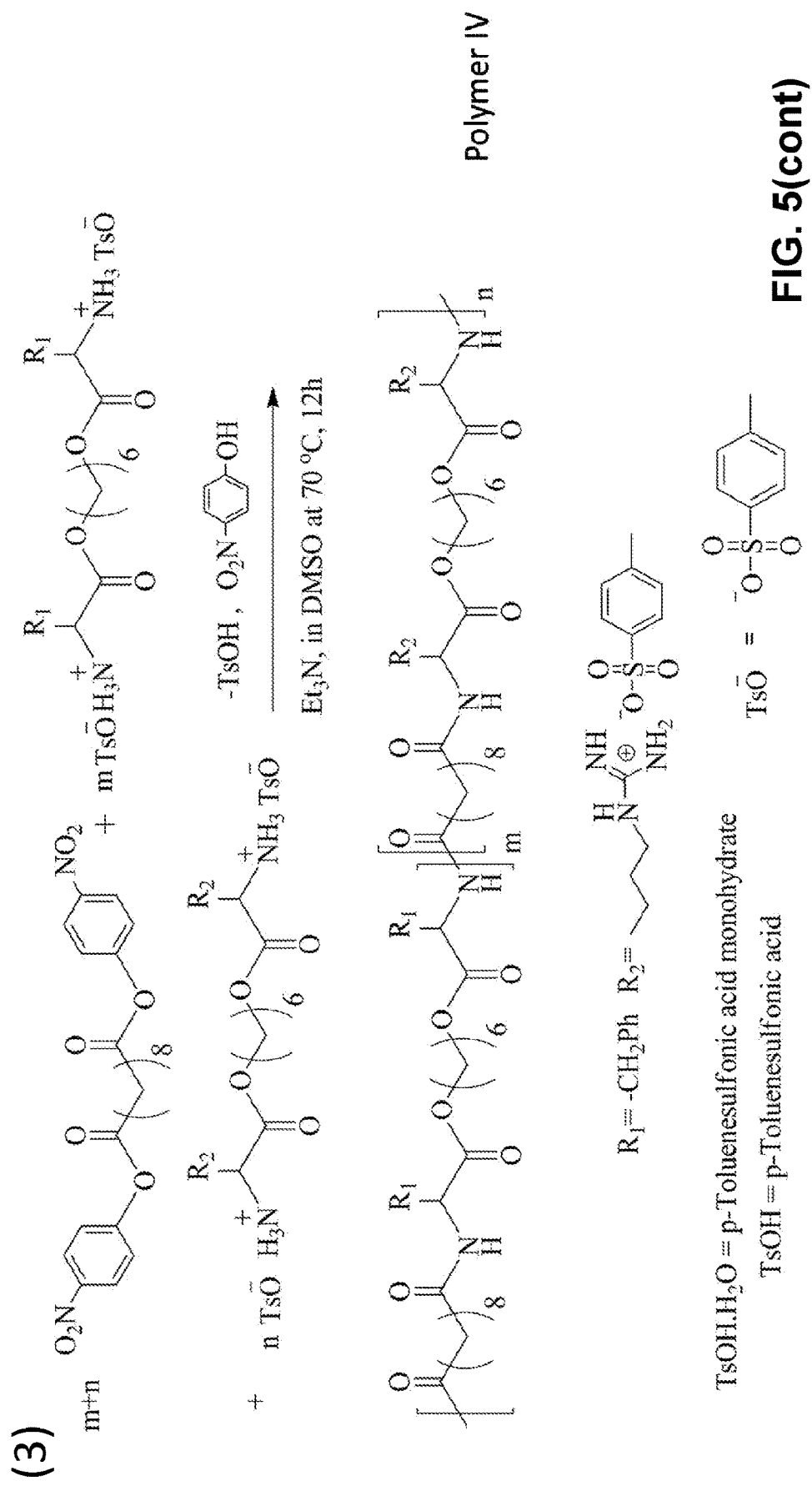
Figure 6A:
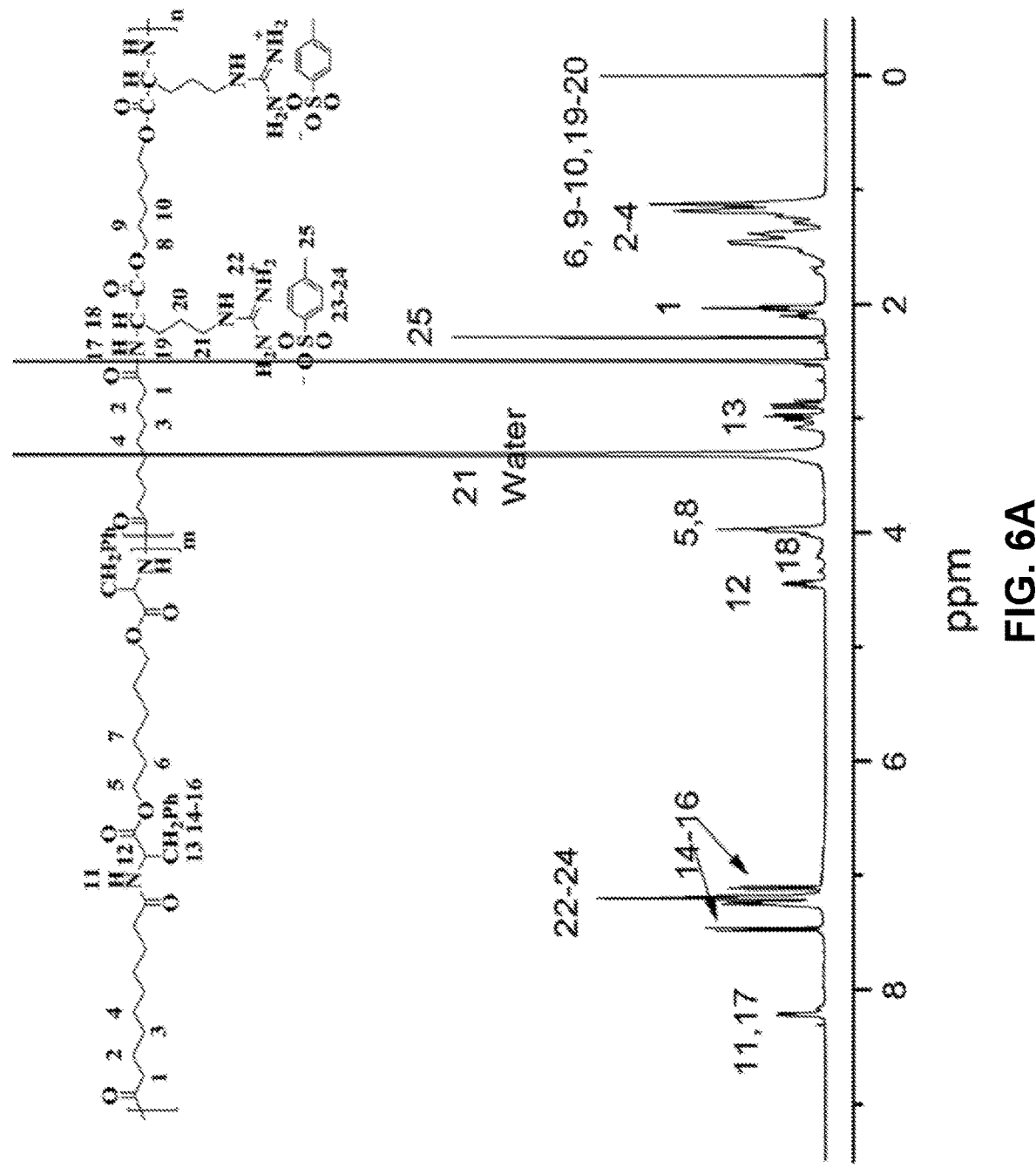
FIG. 6A is a plot showing assignments of $^1$H-NMR spectral peaks of PEA polymer.
Figure 6B:
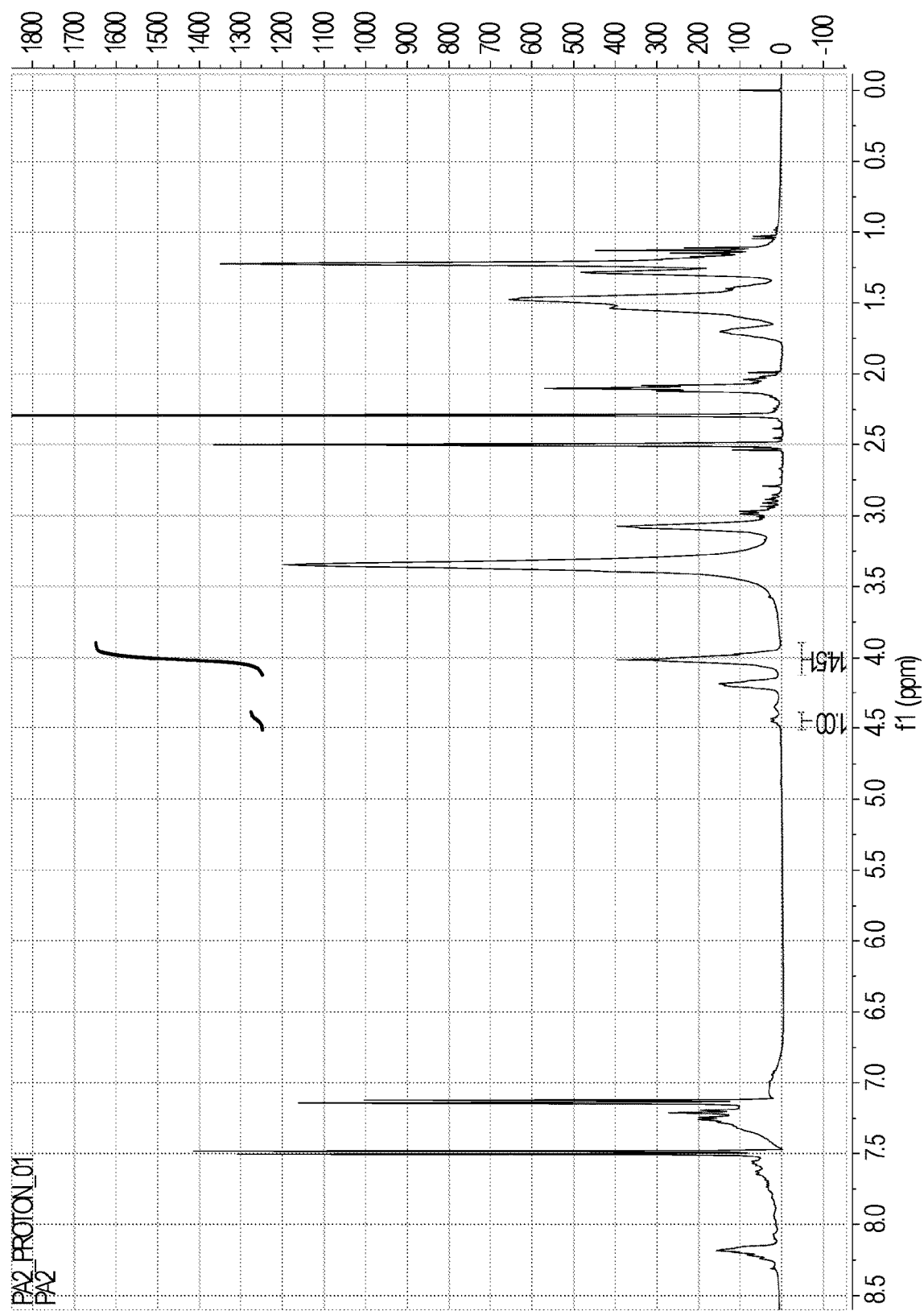
FIG. 6B is a $^1$H-NMR spectrum of PEA10.
Figure 6C:
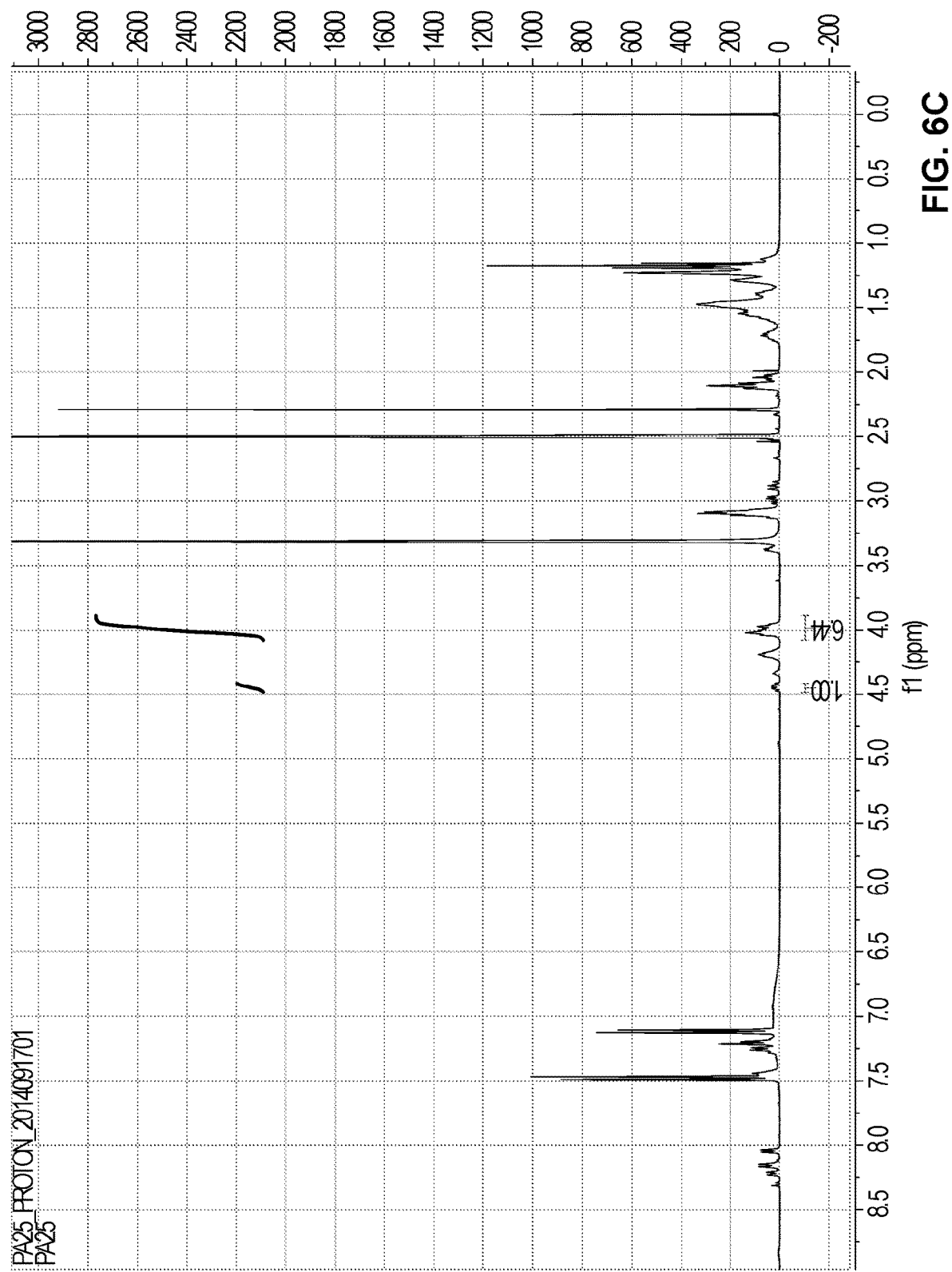
FIG. 6C is a $^1$H-NMR spectrum of PEA25.
Figure 6D:
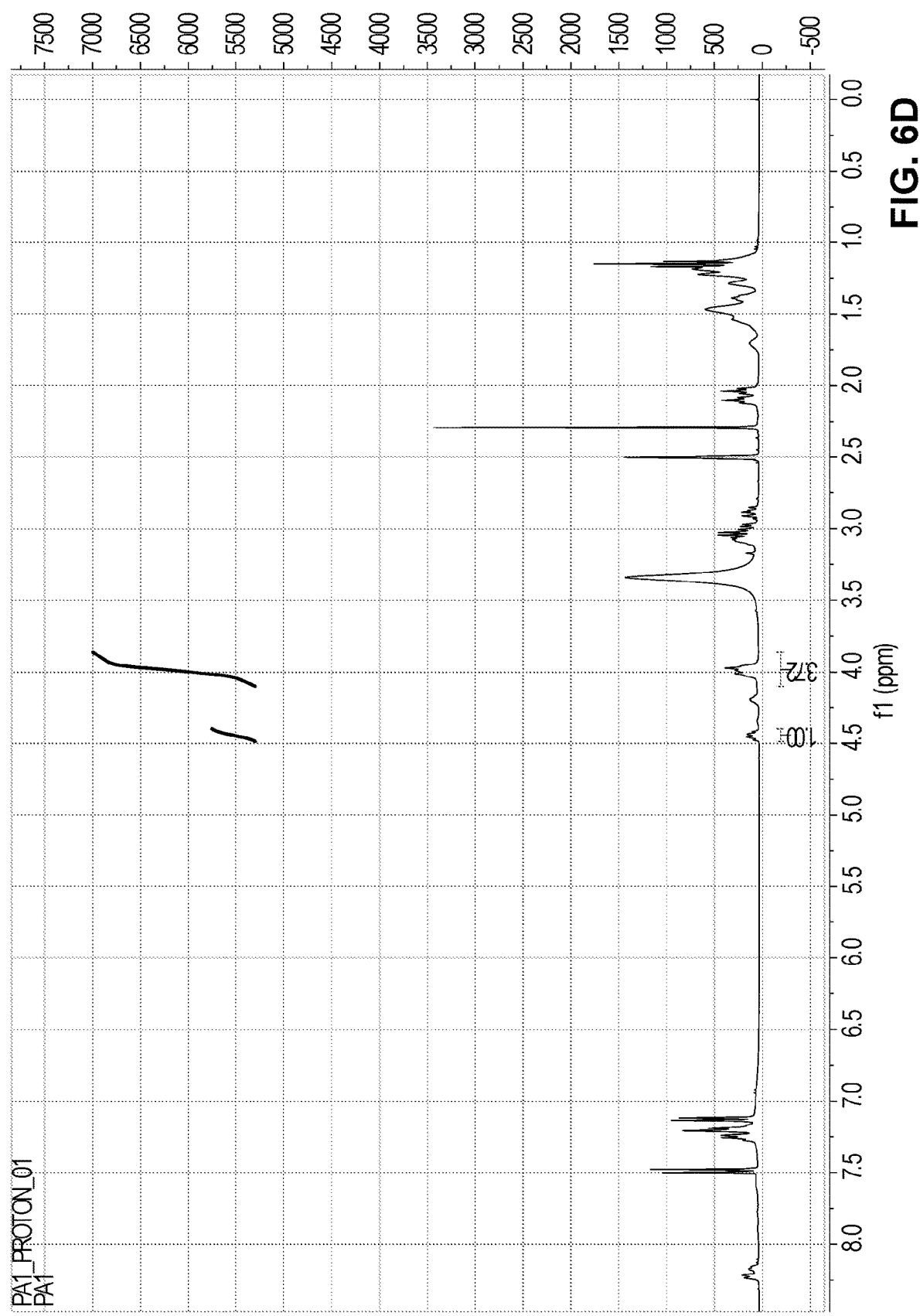
FIG. 6D is a $^1$H-NMR spectrum of PEA50.
Figure 6E:
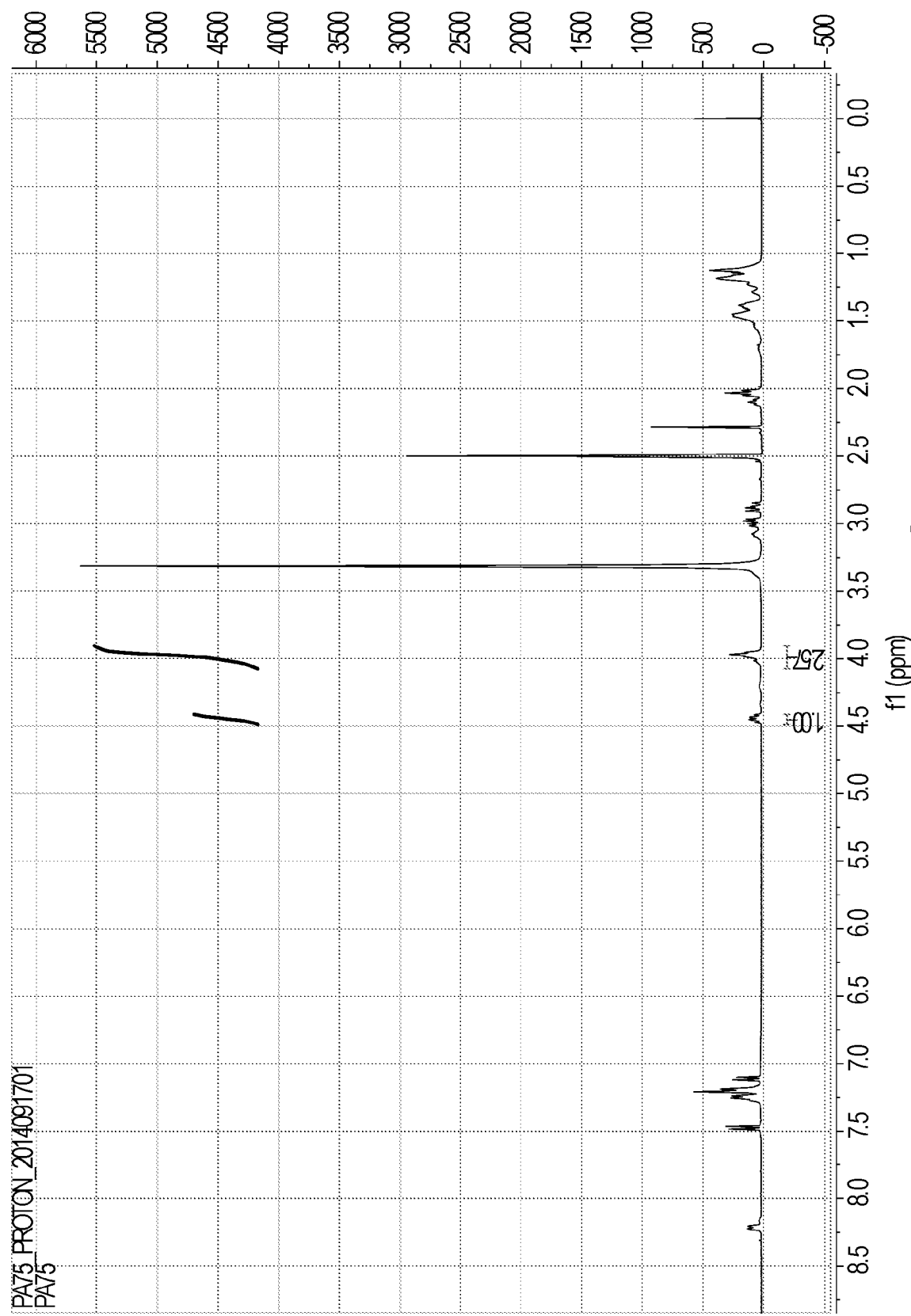
FIG. 6E is a $^1$H-NMR spectrum of PEA75.
Figure 6F:
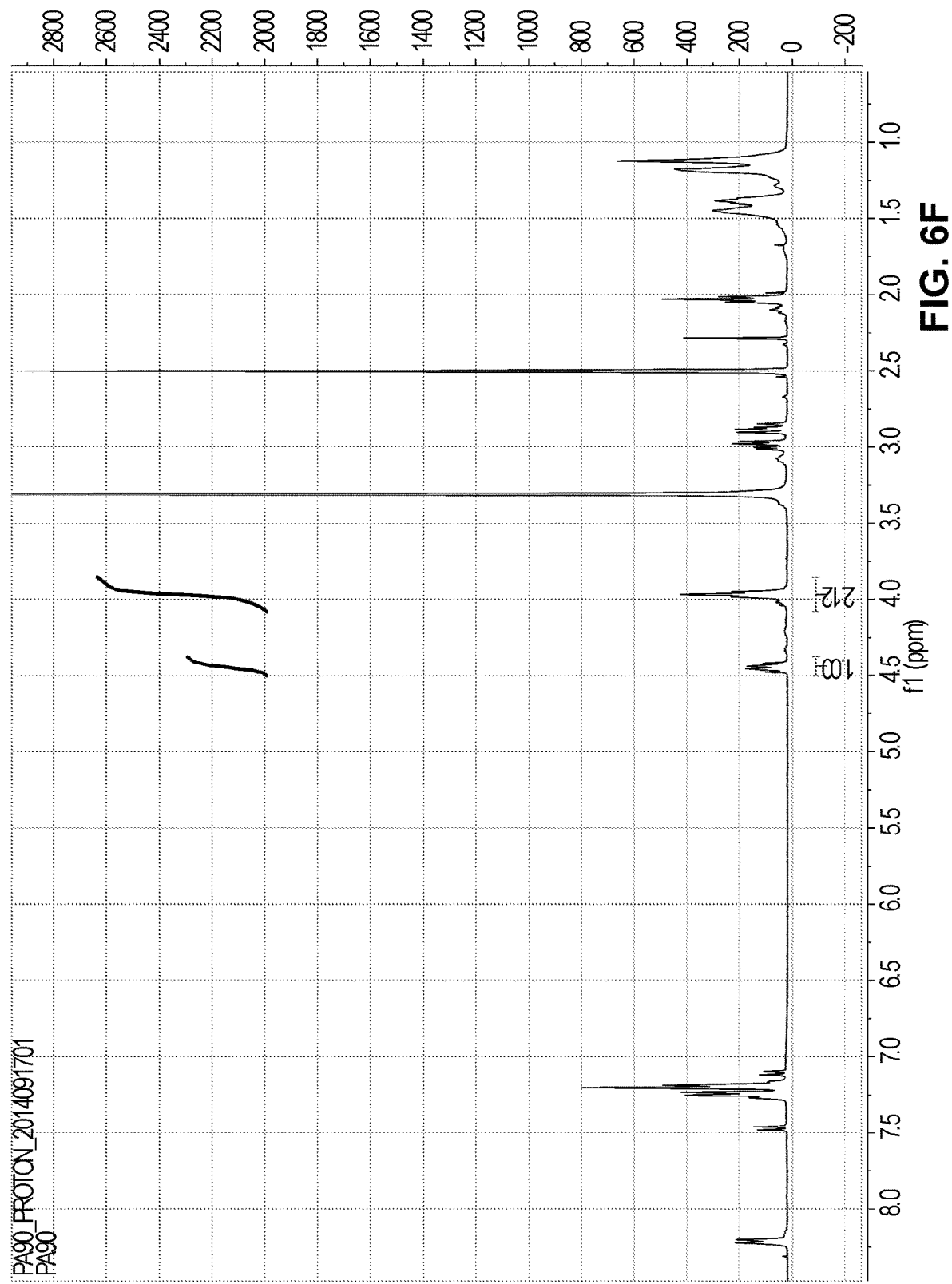
FIG. 6F is a $^1$H-NMR spectrum of PEA90.
Figure 7A:
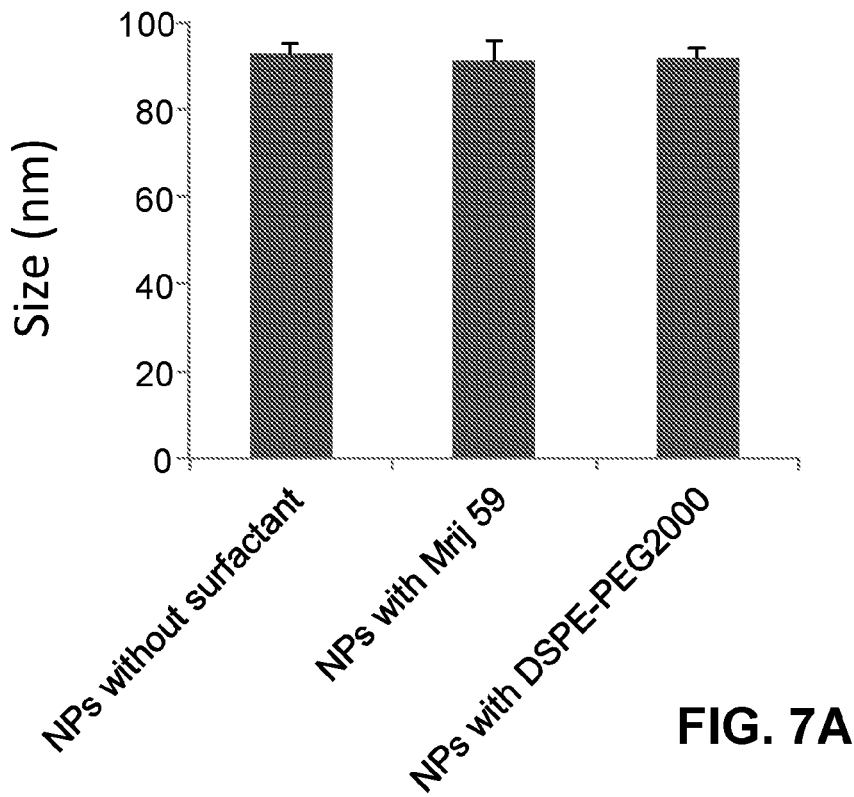
FIG. 7A is a plot of the size of PEA75 NPs measured by dynamic light scattering (DLS) before or after the addition of Mrij 59 or DSPE-PEG2000.
Figure 7B:
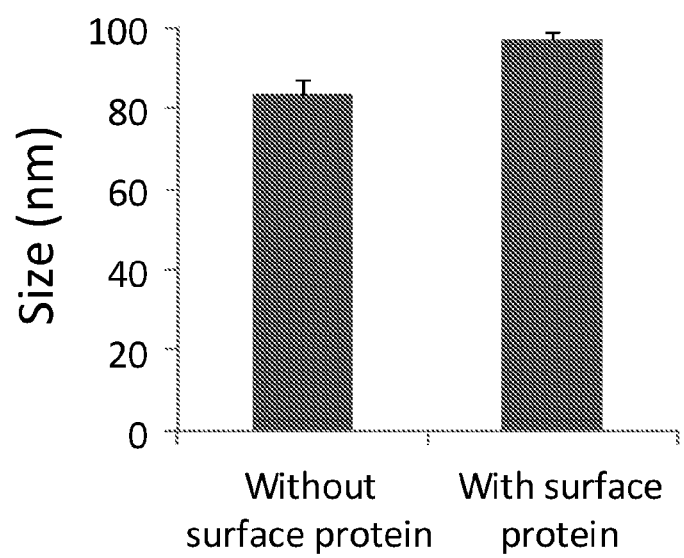
FIG. 7B is a plot of the size of PEA75 NPs measured by dynamic light scattering (DLS) with or without the surface loaded proteins.
Figure 17:
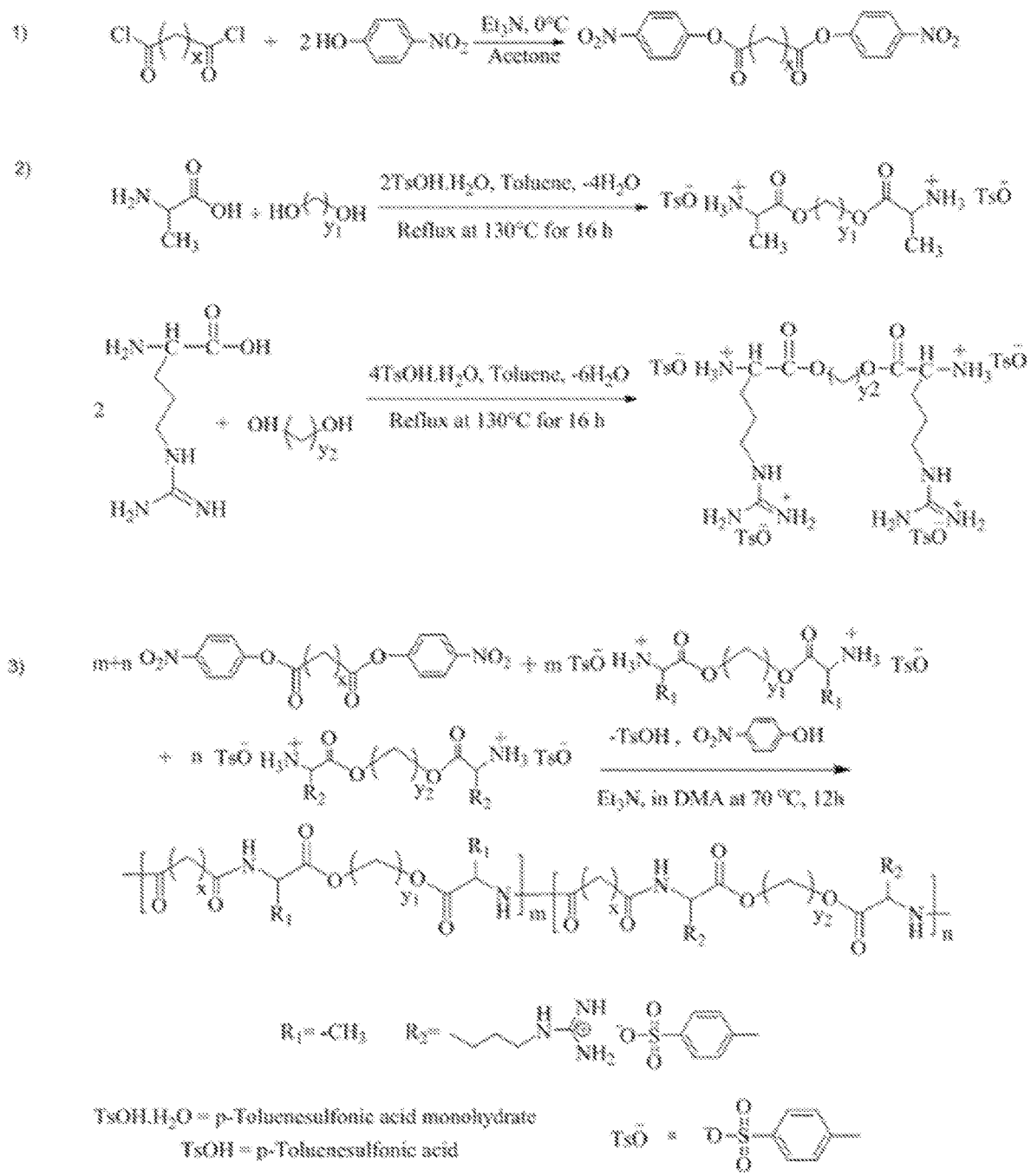
FIG. 17 contains scheme showing synthesis procedures for preparation of alanine and arginine based (Ala-Arg) PEA polymers.

In some embodiments, the polymer that comprises a positively charged component and a hydrophobic component may be prepared as described in Examples 1a and 1b and shown in FIGS. 5 and 17. In some embodiments, the polymer that comprises a positively charged component and a hydrophobic component may be prepared as described in Wu et al., *J. Mater. Chem. B* 2013, 1, 353-360, the disclosure of which is incorporated herein by reference in its entirety.

In some embodiments, the polymer that comprises a positively charged component and a hydrophobic component may be prepared from (i) a monomer of Formula M-1:

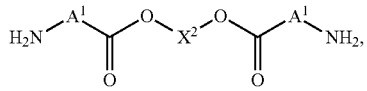

(M-1)

or a salt thereof, wherein $A^1$ and $X^2$ are as defined herein, (ii) a monomer of Formula M-2:

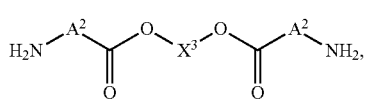

(M-2)

or a salt thereof, wherein $A^2$ and $X^3$ are as defined herein, and (iii) a monomer of Formula M-3:

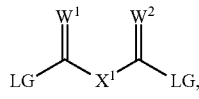

(M-3)

wherein $W^1$, $W^2$ and $X^1$ are as defined herein and LG is a suitable leaving group. In some embodiments, the leaving group is a halogen. In some embodiments, the halogen is Cl, Br, or I. In some embodiments, the leaving group is a p-nitro phenol. In some embodiments, the leaving group is perfluoroalkylsulfonate. In some embodiments, the leaving group is tosylate. In some embodiments, the leaving group is mesylate. In some embodiments, the leaving group is carboxylate.

In some embodiments, the PEA polymer may be prepared by solution polycondensation reaction, wherein the solution comprises a monomer of Formula M-1, a monomer of Formula M-2 and a monomer of Formula M-3.

In some embodiments, the polymer that comprises a positively charged component and a hydrophobic component may be prepared from (iv) a monomer of Formula M-4:

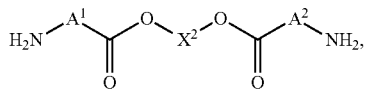

(M-4)

or a salt thereof, wherein $A^1$, $A^2$ and $X^2$ are as defined herein, (v) a monomer of Formula M-3:

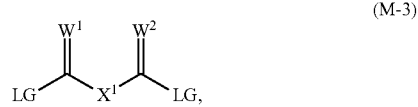

(M-3)

wherein LG, $W^1$, $W^2$, $X^1$ are as described herein.

In some embodiments, the PEA polymer may be prepared according to Scheme 1:

Scheme 1

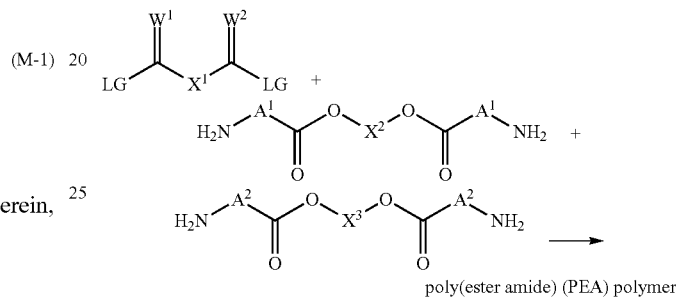

poly(ester amide) (PEA) polymer

In some embodiments, the PEA polymer may be prepared according to Scheme 2:

Scheme 2

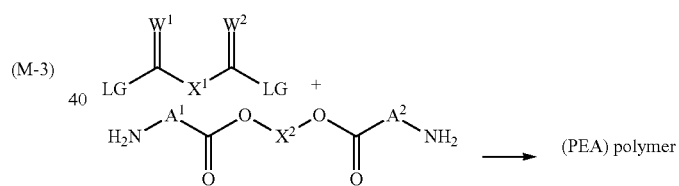

(PEA) polymer

In some embodiments, the solution polycondensation reaction according to Scheme 1 or Scheme 2 is carried out in a polar solvent. In some embodiments, polar solvent is DMSO or DMF. In some embodiments, the solvent is DMSO.

In some embodiments, the polycondensation reaction is carried out at elevated temperature. In some embodiments, the temperature is from about 30° C. to about 200° C., from about 35° C. to about 180° C., from about 40° C. to about 160° C., from about 45° C. to about 150° C., from about 50° C. to about 140° C., from about 55° C. to about 130° C., from about 60° C. to about 120° C., or from about 70° C. to about 100° C. In some embodiments, the temperature is about 70° C.

In some embodiments, the polycondensation reaction is carried out with stirring. In some embodiments, the polycondensation reaction is carried out for a period of time from about 6 h to about 20 h, from about 7 h to about 18 h, or from about 10 h to about 15 h. In some embodiments, the polycondensation reaction is carried out for about 12 h. In some embodiments, the reaction is carried out in the presence of trimethylamine.

In some embodiments, the molar ratio of monomer of Formula M-1 to the monomer of Formula M-2 to the monomer of Formula M-3, or salt of any of the aforementioned, is about 0.25:0.75:1.

In some embodiments, the PEA polymer is precipitated out by adding cold solvent. In some embodiments, the solvent is ethyl acetate.

In some embodiments, the monomer of Formula M-1 is a compound of Formula M-1a:

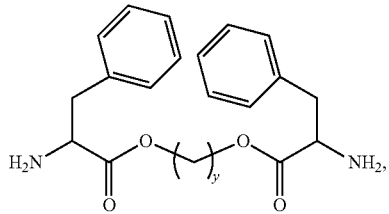

(M-1a)

or salt thereof, wherein y is as defined herein. In some embodiments, y is 6.

In some embodiments, the monomer of Formula M-1 is a compound of Formula M-1b:

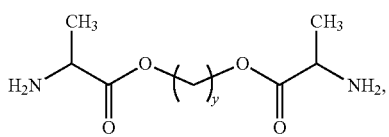

(M-1b)

or salt thereof, wherein y is as defined herein. In some embodiments, y is 6.

In some embodiments, the monomer of Formula M-2 is a compound of Formula M-2a:

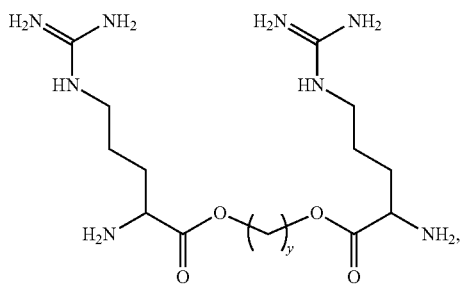

(M-2a)

or salt thereof, wherein y is as defined herein. In some embodiments, y is 6.

In some embodiments, the monomer of Formula M-3 is a compound of Formula M-3a:

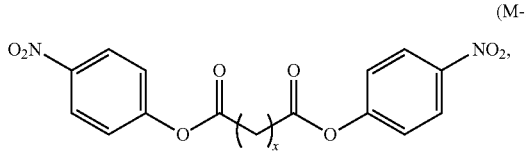

(M-3a)

wherein x is as defined herein. In some embodiments, x is 8.

In some embodiments, the monomer of Formula M-4 is a compound of Formula M-4a:

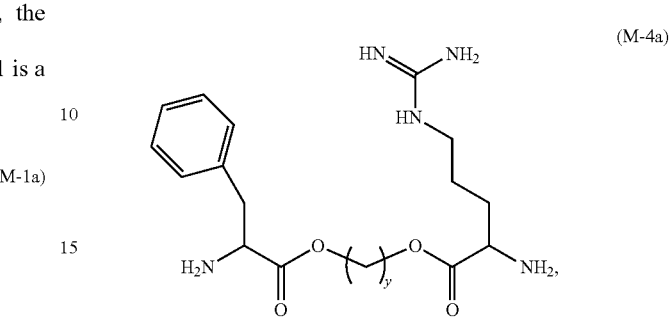

(M-4a)

wherein x is as defined herein. In some embodiments, x is 6.

In some embodiments, the monomer of Formula M-4 is a compound of Formula M-4b:

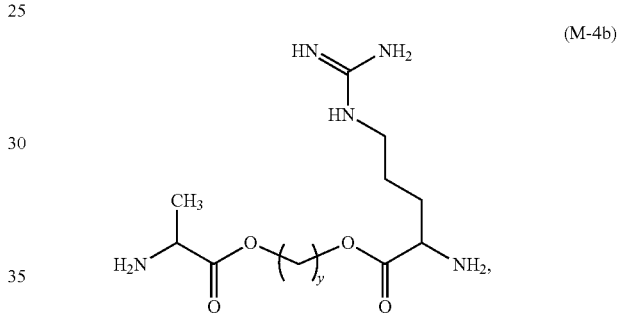

(M-4b)

wherein x is as defined herein. In some embodiments, x is 6.

In some embodiments, monomers of Formulae M-1, M-1a, M-1b, M-2, M-2a, M-4 and M-4a. M-4b may be prepared from an appropriate amino acid and a compound of formula HO—$(CH_2)_n$—OH, wherein n is an integer from 1 to 10. In some embodiments, n is 6. In some embodiments, the preparation is carried out in toluene at about 145° C. or at about 130° C. for about 16 h.

In some embodiments, monomers of Formula M-3 and M-3a may be prepared from adipic, sebacic, malonic, succinic, glutaric, pimelic, suberic, or azelaic acid chlorides and appropriate leaving groups. In some embodiments, monomers of Formula M-3 and M-3a may be prepared from sebacic acid chloride and a p-nitro phenol.

Suitable synthetic methods of starting materials, intermediates and products may be identified by reference to the literature, including reference sources such as: Advances in Heterocyclic Chemistry, Vols. 1-107 (Elsevier, 1963-2012); Journal of Heterocyclic Chemistry Vols. 1-49 (Journal of Heterocyclic Chemistry, 1964-2012); Carreira, et al. (Ed.) Science of Synthesis, Vols. 1-48 (2001-2010) and Knowledge Updates KU2010/1-4; 2011/1-4; 2012/1-2 (Thieme, 2001-2012); Katritzky, et al. (Ed.) Comprehensive Organic Functional Group Transformations, (Pergamon Press, 1996); Katritzky et al. (Ed.); Comprehensive Organic Functional Group Transformations II (Elsevier, 2nd Edition, 2004); Katritzky et al. (Ed.), Comprehensive Heterocyclic Chemistry (Pergamon Press, 1984); Katritzky et al., Comprehensive Heterocyclic Chemistry II, (Pergamon Press, 1996); Smith et al., March's Advanced Organic Chemistry: Reactions, Mechanisms, and Structure, 6th Ed. (Wiley, 2007); Trost et al. (Ed.), Comprehensive Organic Synthesis (Pergamon Press, 1991).

The reactions for preparing the compounds provided herein can be carried out in suitable solvents which can be readily selected by one of skill in the art of organic synthesis.

Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, Protective Groups in Organic Synthesis, 4th Ed., Wiley & Sons, Inc., New York (2006).

Methods of Use

The methods of the disclosure offer the ability to deliver a payload, e.g., a biomolecule (e.g., a therapeutic protein), to the desired biological target without exposing the payload to the harsh gastric conditions.

This disclosure provides for a method of delivering a payload to a cell, comprising contacting the cell with an effective amount of a composition as described herein. In some embodiments, the contacting is in vitro. In some embodiments, the contacting is in vivo. In some embodiments, the cell is a blood cell, a cancer cell, and immune cell (e.g., a macrophage cell), an epithelial cell (e.g., a skin cell), a bacterial cell, or a virus-infected cell.

In some embodiments, the cell is a macrophage cell. For example, the macrophage cell can be a RAW 264.7 cell. The macrophage cell can be unstimulated or stimulated by, for example, lipopolysaccharide (LPS).

In some embodiments, the cell is a cancer cell. In some embodiments, the cancer cell is selected from a breast cancer cell, a colon cancer cell, a leukemia cell, a bone cancer cell, a lung cancer cell, a bladder cancer cell, a brain cancer cell, a bronchial cancer cell, a cervical cancer cell, a colorectal cancer cell, an endometrial cancer cell, an ependymoma cancer cell, a retinoblastoma cancer cell, a gallbladder cancer cell, a gastric cancer cell, a gastrointestinal cancer cell, a glioma cancer cell, a head and neck cancer cell, a heart cancer cell, a liver cancer cell, a pancreatic cancer cell, a melanoma cancer cell, a kidney cancer cell, a laryngeal cancer cell, a lip or oral cancer cell, a lymphoma cancer cell, a mesothelioma cancer cell, a mouth cancer cell, a myeloma cancer cell, a nasopharyngeal cancer cell, a neuroblastoma cancer cell, an oropharyngeal cancer cell, an ovarian cancer cell, a thyroid cancer cell, a penile cancer cell, a pituitary cancer cell, a prostate cancer cell, a rectal cancer cell, a renal cancer cell, a salivary gland cancer cell, a sarcoma cancer cell, a skin cancer cell, a stomach cancer cell, a testicular cancer cell, a throat cancer cell, a uterine cancer cell, a vaginal cancer cell, and a vulvar cancer cell. For example, the cancer cell can be a breast cancer cell, such as an MCF-7 cell.

As used herein, a subject is a mammal, which can include a mouse, a rat, a guinea pig, a farm animal, such as a pig, a goat, a horse, or a cow, a non-human primate, such as a cynomolgus monkey, or a human. In some embodiments, the subject is a human.

The particles and compositions of the disclosure may be used in any method of treating a disease or condition beneficially treated by administration of a payload, e.g., a biomolecule, in a subject.

In some embodiments, the present disclosure provides a method of treating a disease or condition in a subject in need thereof, the method comprising administering to the subject a therapeutically effective amount of a particle or a composition as described herein.

In some embodiments, the disease or condition is an endocrine disorder.

In some embodiments, the endocrine disorder is diabetes, diabetes mellitus, diabetic ketoacidosis, hyperkalaemia, hyperglycemia, growth failure due to GH deficiency or chronic renal insufficiency, Prader-Willi syndrome, Turner syndrome, AIDS wasting or cachexia with antiviral therapy, growth failure in children with GH gene deletion or severe primary IGF1 deficiency, postmenopausal osteoporosis, severe osteoporosis, type 2 diabetes resistant to treatment with metformin and a sulphonylurea, or acromegaly.

In some embodiments, the disease or condition is diabetes, which includes type 1, type 2, gestational, surgically induced, and chemically induced diabetes, and latent autoimmune diabetes in adults (LADA or type 1.5 diabetes).

In some embodiments, the disease or condition can be characterized by an insufficient amount of growth hormone, e.g., human growth hormone (hGH). For example, hGH can be used as a replacement therapy in children or adults with an hGH deficiency. The methods of the disclosure can also be used to deliver, e.g., human growth hormone to treat conditions which produce short stature but is not related to deficiencies in hGH, or in maintaining muscle mass to ameliorate muscle wasting as a result of diseases such as AIDS.

In some embodiments, the disease or condition is cancer.

In some embodiments, the cancer is selected from the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

In some embodiments, cancer is selected from the group selected from sarcoma, angiosarcoma, fibrosarcoma, rhabdomyosarcoma, liposarcoma, myxoma, rhabdomyoma, fibroma, lipoma, teratoma, lung cancer, bronchogenic carcinoma squamous cell, undifferentiated small cell, undifferentiated large cell, adenocarcinoma, alveolar bronchiolar carcinoma, bronchial adenoma, sarcoma, lymphoma, chondromatous hamartoma, mesothelioma, gastrointestinal cancer, cancer of the esophagus, squamous cell carcinoma, adenocarcinoma, leiomyosarcoma, lymphoma, cancer of the stomach, carcinoma, lymphoma, leiomyosarcoma, cancer of the pancreas, ductal adenocarcinoma, insulinoma, glucagonoma, gastrinoma, carcinoid tumor, vipoma, cancer of the small bowel, adenocarcinoma, lymphoma, carcinoid tumors, Kaposi's sarcoma, leiomyoma, hemangioma, lipoma, neurofibroma, fibroma, cancer of the large bowel or colon, tubular adenoma, villous adenoma, hamartoma, leiomyoma, genitourinary tract cancer, cancer of the kidney adenocarcinoma, Wilm's tumor (nephroblastoma), lymphoma, leukemia, cancer of the bladder, cancer of the urethra, squamous cell carcinoma, transitional cell carcinoma, cancer of the prostate, cancer of the testis, seminoma, teratoma, embryonal carcinoma, teratocarcinoma, choriocarcinoma, sarcoma, interstitial cell carcinoma, fibroma, fibroadenoma, adenomatoid tumors, lipoma, liver cancer, hepatoma hepatocellular carcinoma, cholangiocarcinoma, hepatoblastoma, angiosarcoma, hepatocellular adenoma, hemangioma, bone cancer, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochrondroma (osteocartilaginous exostoses), benign chondroma, chondroblastoma, chondromyxofibroma, osteoid osteoma giant cell tumor, nervous system cancer, cancer of the skull, osteoma, hemangioma, granuloma, xanthoma, osteitis deformans, cancer of the meninges meningioma, meningiosarcoma, gliomatosis, cancer of the brain, astrocytoma, medulloblastoma, glioma, ependymoma, germinoma (pinealoma), glioblastoma multiforme, oligodendroglioma, schwannoma, retinoblastoma, congenital tumors, cancer of the spinal cord, neurofibroma, meningioma, glioma, sarcoma, gynecological cancer, cancer of the uterus, endometrial carcinoma, cancer of the cervix, cervical carcinoma, pre tumor cervical dysplasia, cancer of the ovaries, ovarian carcinoma, serous cystadenocarcinoma, mucinous cystadenocarcinoma, unclassified carcinoma, granulosa-theca cell tumor, Sertoli Leydig cell tumor, dysgerminoma, malignant teratoma, cancer of the vulva, squamous cell carcinoma, intraepithelial carcinoma, adenocarcinoma, fibrosarcoma, melanoma, cancer of the vagina, clear cell carcinoma, squamous cell carcinoma, botryoid sarcoma, embryonal rhabdomyosarcoma, cancer of the fallopian tubes, hematologic cancer, cancer of the blood, acute myeloid leukemia (AML), chronic myeloid leukemia (CML), acute lymphoblastic leukemia (ALL), chronic lymphoblastic leukemia, chronic lymphocytic leukemia, myeloproliferative diseases, multiple myeloma, myelodysplastic syndrome, Hodgkin's lymphoma, non-Hodgkin's lymphoma (malignant lymphoma), Waldenstrom's macroglobulinemia, skin cancer, malignant melanoma, basal cell carcinoma, squamous cell carcinoma, Kaposi's sarcoma, moles dysplastic nevi, lipoma, angioma, dermatofibroma, keloids, psoriasis, adrenal gland cancer, and neuroblastoma.

In some embodiments, the disease or condition is an inflammatory disease or condition. In some embodiments, the inflammatory disease or condition is selected from arthritis, multiple sclerosis, rheumatoid arthritis, psoriasis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis, Paget's disease of bone, palindromic rheumatism, patellofemoral pain syndrome, Pellegrini-Stieda syndrome, pigmented villonodular synovitis, piriformis syndrome, plantar fasciitis, polyarteritis nodos, polymyalgia rheumatica, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, reperfusion injury, retrocalcaneal bursitis, rheumatic fever, rheumatoid vasculitis, rotator cuff tendinitis, sacroiliitis, salmonella osteomyelitis, sarcoidosis, saturnine gout, Scheuermann's osteochondritis, scleroderma, septic arthritis, seronegative arthritis, shigella arthritis, shoulder-hand syndrome, sickle cell arthropathy, Sjogren's syndrome, slipped capital femoral epiphysis, spinal stenosis, spondylolysis, staphylococcus arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, and yersinial arthritis In some embodiments, the disease or condition is associated with haemostasis and thrombosis. In some embodiments, the disease or condition associated with haemostasis and thrombosis is selected from haemophilia A, haemophilia B, hereditary AT-III deficiency in connection with surgical or obstetrical procedures or for thromboembolism, venous thrombosis and purpura fulminans in patients with severe hereditary protein C deficiency, pulmonary embolism, myocardial infarction, acute ischaemic stroke, occlusion of central venous access devices, acute myocardial infarction, haemorrhage in patients with haemophilia A or B and inhibitors to factor VIII or factor IX, severe sepsis with a high risk of death, heparin-induced thrombocytopaenia, blood-clotting risk in coronary angioplasty, acute evolving transmural myocardial infarction, deep vein thrombosis, arterial thrombosis, occlusion of arteriovenous cannula, and thrombolysis in patients with unstable angina.

In some embodiments, the disease or condition is associated with metabolic enzyme deficiencies. In some embodiments, the disease or condition associated with metabolic enzyme deficiencies is Gaucher's disease, Pompe disease, glycogen storage disease type II, Hurler and Hurler-Scheie forms of mucopolysaccharidosis I, mucopolysaccharidosis II, Hunter syndrome, mucopolysaccharidosis VI, or Fabry disease.

In some embodiments, the disease or condition is pulmonary or gastrointestinal-tract disorder. In some embodiments, the pulmonary or gastrointestinal-tract disorder is congenital α-1-antitrypsin deficiency, gas, bloating, cramps and diarrhea due to inability to digest lactose, cystic fibrosis, chronic pancreatitis, pancreatic insufficiency, post-Billroth II gastric bypass surgery, pancreatic duct obstruction, steatorrhoea, poor digestion, gas, or bloating.

In some embodiments, the disease or condition is associated with immunodeficiencies. In some embodiments, the disease or condition is associated with immunodeficiencies is severe combined immunodeficiency disease due to adenosine deaminase deficiency or primary immunodeficiencies.

In some embodiments, the disease or condition is associated with haematopoiesis. In some embodiments, the disease or condition is associated with haematopoiesis is anaemia, myleodysplasia, anaemia due to renal failure or chemotherapy, preoperative preparation, anaemia in patients with chronic renal insufficiency and chronic renal failure (+/−dialysis), neutropaenia, neutropaenia in AIDS or post-chemotherapy or bone marrow transplantation, severe chronic neutropaenia, leukopaenia, myeloid reconstitution post-bone-marrow transplantation, or thrombocytopaenia (especially after myelosuppressive chemotherapy).

In some embodiments, the disease or condition is associated with infertility. In some embodiments, the disease or condition is associated with infertility is assisted reproduction and treating infertility with luteinizing hormone deficiency.

In some embodiments, the disease or condition is associated with immunoregulation. In some embodiments, the disease or condition is associated with immunoregulation is chronic hepatitis C infection, hairy cell leukaemia, chronic myelogenous, leukaemia, Kaposi's sarcoma, hepatitis B, melanoma, Kaposi's sarcoma, follicular lymphoma, hairy-cell leukaemia, condylomata acuminata, hepatitis C, condylomata acuminata (genital warts, caused by human papillomavirus), multiple sclerosis, chronic granulomatous disease, severe osteopetrosis, metastatic renal cell cancer, or melanoma.

In some embodiments, the disease or condition is associated with growth regulation. In some embodiments, the disease or condition is associated with growth regulation is acromegaly, symptomatic relief of VIP-secreting adenoma and metastatic carcinoid tumours, spinal fusion surgery, bone injury repair, tibial fracture nonunion, lumbar, spinal fusion, precocious puberty, severe oral mucositis in patients undergoing chemotherapy or debridement adjunct for diabetic ulcers.

In some embodiments, the disease or condition is decubitus ulcer, varicose ulcer, debridement of eschar, dehiscent wound, sunburn, or acute decompensated congestive heart failure.

In some embodiments, the disease or condition is associated with enzymatic degradation of macromolecules. In some embodiments, the disease or condition is associated with enzymatic degradation of macromolecules is dystonia (e.g. cervical), debridement of chronic dermal ulcers and severely burned areas, cystic fibrosis, respiratory tract infections, respiratory tract infections in selected patients with FVC greater than 40% of predicted, debridement of necrotic tissue, or debridement of necrotic tissue or liquefication of slough in acute and chronic lesions (e.g., pressure ulcers, varicose and diabetic ulcers, burns, postoperative wounds, pilonidal cyst wounds, carbuncles, and other wounds).

In some embodiments, the disease or condition is respiratory syncytial virus infection, asthma.

In some embodiments, the disease or condition is infectious disease. In some embodiments, the infectious disease is HIV infection, or AIDS.

In some embodiments, the present disclosure provides a method of inducing an immune response in a subject in need thereof, the method comprising administering to the subject a therapeutically effective amount of a particle or a composition as described herein.

In some embodiments, the present disclosure provides a method of inducing an immune response vaccinating a subject in need thereof, the method comprising administering to the subject a therapeutically effective amount of a particle or a composition comprising an antigen as described herein.

In some embodiments, the method of inducing an immune response or vaccinating a subject comprises Hepatitis B vaccination, Hepatitis C vaccination, HIV vaccination, HPV vaccination, or Lyme disease vaccination.

In some embodiments, the method of inducing an immune response or vaccinating a subject comprises dust mite allergies vaccination.

EXAMPLES

General Methods

Materials

Alexa Fluor 647 Cadaverine (disodium salt) FITC-Annexin-V were purchased from Invitrogen (Carlsbad, Calif.). Carboxy terminated PLGA (50:50 Poly(DL-lactide-co-glycolide), (0.55-0.75 dL/g)) was purchased from Lactel, Adsorbable Polymers.

Analytical Methods $^1$H NMR spectra were recorded on a Bruker AVANCE-400 NMR spectrometer. Peptide-encapsulated NPs were prepared using the nanoprecipitation method.

The NP sizes and zeta potentials were obtained by quasi-electric laser light scattering using a ZetaPALS dynamic light-scattering detector (15 mW laser, incident beam ¼ 676 nm; Brookhaven Instruments). Electron microscopy (EM) was performed at the Harvard Medical School EM facility on a Tecnai™ G$^2$ Spirit BioTWIN EM. The size and zeta potential of the NPs were determined by Dynamic Light Scattering or DLS (Malvern Zetasize NanoZS90, Malvern Instruments Ltd., UK). NP samples for transmission electron microscopy (TEM) were stained with 1% uranyl acetate and imaged using a Tecnai G$^2$ Spirit BioTWIN microscope (FEI Company) operating at 80 kV.

Statistical analysis

All data are presented as their means, with either SD or SEM as indicated. Statistical significance was determined by a two-tailed Student's t test (a=0.05) assuming equal variance.

Animals

Animals were obtained from Charles River Laboratories or Dashuo Laboratory Animal Center. All in vivo studies were performed in accordance with National Institutes of Health animal care guidelines. The animal protocol was approved by Institutional Animal Care and Use Committees on animal care of Harvard Medical School, and Institutional Animal Care and Use Committee of Sichuan University. The animals were allowed free access to food pellets and water.

Cell Culture

Caco-2 cells were maintained in Dulbecco's Modified Eagle's Medium (DMEM; Invitrogen) with high glucose, 10% (v/v) fetal bovine serum (FBS; Sigma), and 1% non-essential amino acid, and incubated at 37° C., 95% relative humidity, and 5% $CO_2$.

Example 1a

Synthesis of Poly(Ester Amide) (PEA) Polymers Containing Phe (Phenylalanine) and Arg (Arginine)

The general scheme of the synthesis of Phe-Arg-PEAs is divided into the following three major steps (FIG. 1B and FIG. 5): 1) the preparation of di-p-toluenesulfonic acid salts of bis(L-phenylalanine)hexane diesters (Monomer I) and tetra-p-toluenesulfonic acid salts of bis(L-arginine) hexane diesters (Monomer II); 2) the preparation of di-p-nitrophenyl esters of sebacic acid (Monomer III); and 3) the synthesis of Phe-Arg-PEAs (IV) via solution polycondensation of I, II, and III. The amino acid diester monomers (I and II) were prepared via a solid-liquid reaction at high temperature. Di-p-nitrophenyl esters of sebacic acid (III) were prepared by reacting sebacoyl chloride with p-nitrophenol. All of the details for the synthesis of monomers (I, II, and III) can be found in previous reports (see, e.g., R. Katsarava, V. Beridze, N. Arabuli, D. Kharadze, C. C. Chu, C. Y. Won, *Journal of Polymer Science Part A: Polymer Chemistry* 1999, 37, 391-407; J. Wu, M. A. Mutschler, C.-C. Chu, *Journal of Materials Science: Materials in Medicine* 2011, 22, 469-479).

Phe-Arg-PEAs were prepared by polycondensation of the above monomers I, II, and III at five different ratios of I to II. The prepared polymers are summarized in Table S1. These Phe-Arg-PEAs are referred to as PEAx, where x is the molar percent of L-Phe diester monomer in the mixture of L-Phe diester and L-Arg diester monomers. For example, PEA25 indicates that the molar% of L-Phe diester monomer I in the copolymer is 25%, and the molar% of L-Arg diester monomer II in the copolymer is 75%. As an example, the synthesis of PEA-25, via solution polycondensation, was as follows. Monomer I (L-Phe diester, 0.25 mmol), monomer II (L-Arg diester, 0.75 mmol), and monomer III (Di-p-nitrophenyl esters of sebacic acid, 1.0 mmol) were added in 1.5 mL of dry DMSO, and mixed well by vortexing. The mixture solution was heated to 70° C., with stirring, to obtain a uniform mixture. Triethylamine (0.31 mL, 2.2 mmol) was added dropwise to the mixture at 70° C. with vigorous stirring until the monomers were completely dissolved. The solution color turned yellow within several minutes. The reaction vial was then kept at 70° C. for 12 h in a thermostat bath without stirring. The resulting polymer product was precipitated out by adding cold ethyl acetate. Then the polymer was purified twice using methanol to dissolve the polymer, followed by precipitation in cold ethyl acetate. The final product was dried in a vacuum at room temperature. All the prepared monomers and polymers were characterized by standard physicochemical methods including $^1$H-NMR, FTIR, DSC and solubility test. All PEAs are insoluble in water, and have high production yields (>80%) under optimized reaction conditions. The chemical structure of Phe-Arg-PEAs was confirmed by $^1$H-NMR spectra (FIGS. 6A-6F). The actual molar percentages of Phe in amino acid were calculated from the integration of $^1$H-NMR peaks as listed in Table 1.

TABLE 1

Theoretical and actual molar percentages of Phe in amino acid in different PEAs.

| | PEA10 | PEA25 | PEA50 | PEA75 | PEA90 |
|---|---|---|---|---|---|
| Theoretical molar percentages of Phe (%) | 10 | 25 | 50 | 75 | 90 |
| Actual molar percentages of Phe (%) | 13.7 | 31.0 | 53.8 | 77.8 | 94.3 |

The number in names of prepared PEA polymers (e.g., PEA10, PEA25, PEA50, PEA75, and PEA90) indicates the molar percent of L-Phe diester monomer in L-Phe and L-Arg diester monomers.

Example 1b

Synthesis of Poly(Ester Amide) (PEA) Polymers Containing Ala (Alanine) and Arg (Arginine)

The general scheme of the synthesis of Ala-Arg-PEAs is divided into the following three major steps (FIG. 17): 1) the preparation of di-p-nitrophenyl esters of suberic acid; 2) the preparation of di-p-toluenesulfonic acid salts of bis(alanine) hexane diesters and tetra-p-toluenesulfonic acid salts of bis(arginine) hexane diesters; and 3) the synthesis of Ala-Arg-PEAs (IV) via solution polycondensation of 1) and 2). All monomers were prepared according to the methods described in Example 11a.

Ala-Arg-PEAs were prepared by polycondensation of the above monomers at five different ratios of Ala and Arg containing monomers. The prepared polymers are summarized in Table 1a. Referring to FIG. 17, x=6, y1=6 and y2=6. Further, m represents the molar amount of Ala-containing monomer; and n represents the molar amount of Arg containing monomer, and m+n represents the molar amount of the suberic diester monomer. Polymers are named as Ala-Arg-z, z=100*m/(m+n), with z values: 10, 25, 50, 75, 90.

TABLE 1a

Molecular weight of prepared polymers

| | Mn | Mw | Mw/Mn |
|---|---|---|---|
| Ala-Arg-10 | 8930 | 11470 | 1.28 |
| Ala-Arg-25 | 9875 | 12830 | 1.30 |

TABLE 1a-continued

Molecular weight of prepared polymers

| | Mn | Mw | Mw/Mn |
|---|---|---|---|
| Ala-Arg-50 | 10040 | 13260 | 1.32 |
| Ala-Arg-75 | 9960 | 11550 | 1.16 |
| Ala-Arg-90 | 11790 | 14780 | 1.25 |

Exemplary protocol for the polycondensation reaction is as follows. Ala diester, Arg diester and di-p-nitrophenyl esters of suberic acid were mixed. The mixture solution in DMA was heated to 70° C., with stirring, to obtain a uniform mixture. Triethylamine was added dropwise to the mixture at 70° C. with vigorous stirring until the monomers were completely dissolved. The reaction vial was then kept at 70° C. for 12 h in a thermostat bath without stirring.

Example 2

Synthesis and Characterization of Nanoparticles

Preparation

The NPs were prepared with the five different PEAs described in Example 1a, or 1:1 wt % mixture of a PEA polymer and poly(lactic-co-glycolic acid) (PLGA).

The NPs were prepared using a simple and robust self-assembly nanoprecipitation method. To summarize, 10 mg of PEAs (or a mixture of equal amount of PEAs and PLGA), and 1 mg of insulin were dissolved in 1 mL of DMSO solvent. Next, the polymer and insulin solution was added dropwise into 20 mL aqueous solution containing 2 mg of coating protein, such as transferrin (TO or BSA. The NPs formed instantly upon mixing. The suspension was stirred for another 15 min at room temperature to maximize the surface protein capture. Subsequently, 0.2 mL of an aqueous solution containing 2 mg of Mrij 59 or DSPE-PEG2000 was added into the NPs solution, which was then stirred for another 5 minutes. NPs were washed twice in Amicon tubes (MWCO 100 kDa; Millipore) to remove remaining DMSO and free compounds with ice-cold water, and concentrated in 1 mL of phosphate-buffered saline (PBS) solution. For the preparation of NPs without surface-loaded proteins, the Mrij 59 was added immediately after the formation of the NPs. For the preparation of BSA-Au loaded NPs, 10% of the insulin or 10% of the BSA was replaced with BSA-Au in the formulation. The NPs were then prepared following the same procedure. For the preparation of NPs labeled with DiD dye, DiD was added in the DMSO at 0.1% (W/W) of the amount of polymers. For the preparation of NPs labeled with Alexa Fluor 647, PLGA polymer in the formulation (PLGA-PEA75 NPs) was substituted with Alexa Fluor 647-conjugated PLGA, which was synthesized according to the previous report (N. Kamaly, G. Fredman, M. Subramanian, S. Gadde, A. Pesic, L. Cheung, Z. A. Fayad, R. Langer, I. Tabas, O. C. Farokhzad, *Proc Natl Acad Sci USA* 2013, 110, 6506-6511).

Determination of the NP Structure

Figure 1C:
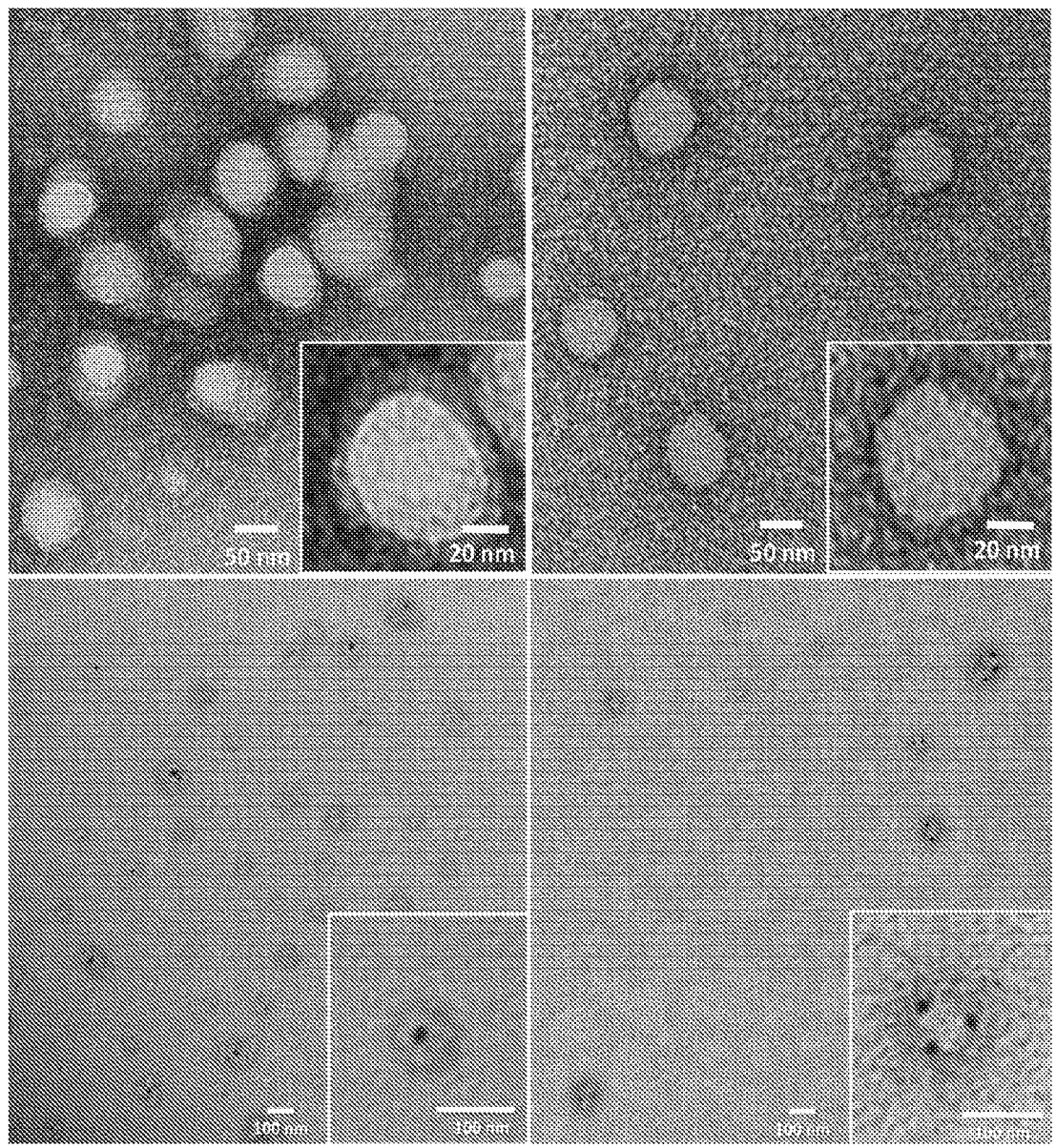
FIG. 1C contains TEM images of PEA75 nanoparticles (c) with and (d) without surface proteins; TEM image of PEA75 NPs with (e) inner or (f) surface loaded BSA-Au.

The NPs without a surface protein coating did not exhibit the core-shell structure (FIG. 1C, see segment (d)). To further clarify the NP structure, bovine serum albumin (BSA) conjugated with gold nanospheres (5 nm) (BSA-Au) were used in the NP formulation. When the BSA-Au was dissolved in DMSO and co-precipitated with the polymer (representing a therapeutic protein), it was completely encapsulated within the NPs (FIG. 1C, see segment (e)). By contrast, the BSA-Au was loaded on the NP surface when it was dissolved in the aqueous solution, representing a targeting protein (FIG. 1C, segment (f)).

Determination of the NP Hydrophobicity

Figure 2A:
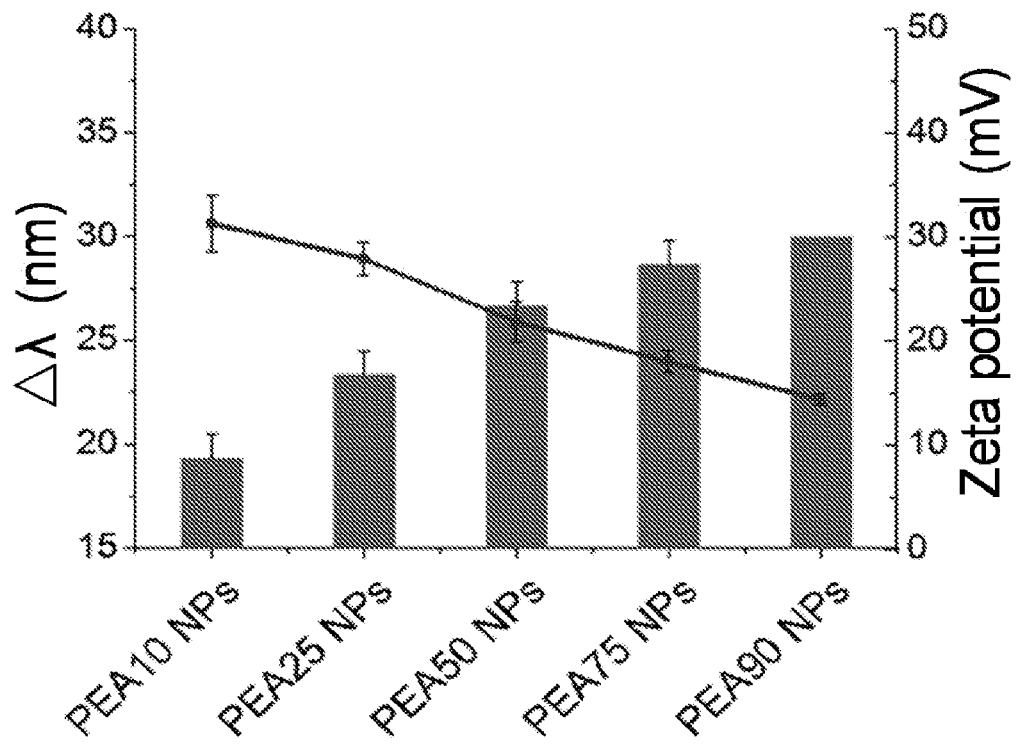
FIG. 2A is a plot of the zeta potential of different PEA NPs and the peak wavelength shift of CBB (Δλ) incubated with different NPs.

The hydrophobicity of the nanoparticles was determined with Coomassie Brilliant Blue (CBB) G-250 dye as previously described (see, e.g., T. Akagi, K. Watanabe, H. Kim, M. Akashi, *Langmuir* 2010, 26, 2406-2413). The NPs were prepared without insulin or surface-loaded proteins to rule out the influence of proteins. The protocol is as follows. 1 ml of NP solution, of different concentrations, was mixed with 1 ml of CBB solution (0.1 mM), and then the mixture was stirred for 20 min at room temperature. Free CBB was used as control. The absorption spectrum of CBB was monitored in a wavelength range of 400-800 nm to detect the shift of peak absorption wavelength, using a Varioskan Flash Multimode Reader (Thermo Fisher Scientific, USA). The results of the measurement of peak wavelength shift of CBB ($\Delta\lambda$) incubated with different NPs are shown in FIG. 2A.

Size, Shape, Polydispersity Index (PDI) and Zeta Potential

The resulting PEA and PLGA-PEA NPs had size of 80-110 nm. Size, polydispersity index (PDI) and zeta potential of different NPs are shown in Table 2.

TABLE 2

Size, polydispersity index (PDI) and zeta potential of different NPs

| Sample | Size (nm) | PDI | Zeta potential(mV) |
|---|---|---|---|
| PEA10 NPs | 108.8 ± 4.9 | 0.125 | 31.3 ± 2.7 |
| PEA25 NPs | 102.2 ± 3.7 | 0.167 | 27.9 ± 1.6 |
| PEA50 NPs | 99.3 ± 4.5 | 0.184 | 21.9 ± 2.0 |
| PEA75 NPs | 91.3 ± 4.6 | 0.184 | 18.0 ± 1.1 |
| PEA90 NPs | 101.2 ± 3.1 | 0.165 | 14.4 ± 0.5 |
| PLGA-PEA10 NPs | 102.1 ± 5.4 | 0.095 | 27.9 ± 1.6 |
| PLGA-PEA25 NPs | 107.8 ± 7.7 | 0.098 | 23.8 ± 0.8 |
| PLGA-PEA50 NPs | 108.2 ± 2.5 | 0.141 | 20.4 ± 1.2 |
| PLGA-PEA75 NPs | 90.3 ± 2.1 | 0.112 | 16.0 ± 1.3 |
| PLGA-PEA90 NPs | 81.5 ± 2.2 | 0.125 | 11.8 ± 0.8 |

Transmission electron microscopy (TEM) images showed that these NPs are spherical and exhibit a core-shell structure with a distinct protein coating (Figure FIG. 1C, segment (c)).

Figure 8:
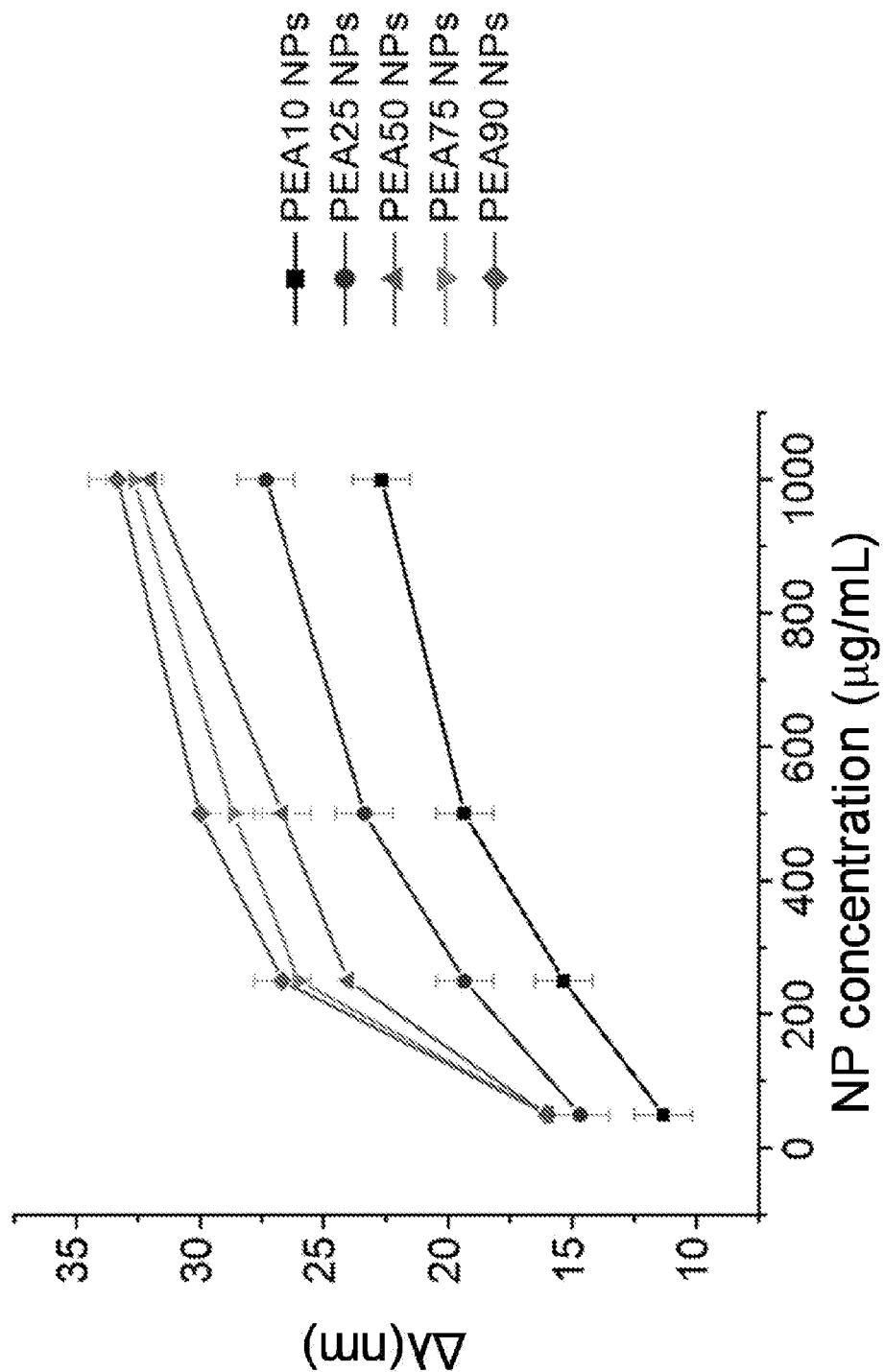
FIG. 8 is a plot of the changes in the wavelength of the maximum absorption of CBB incubated with different NPs at different concentrations.

As can be seen from data in Example 2 and Table 2, hydrophobicity and charge density of the PEAs can be tuned by changing the Phe/Arg ratio, and thus the NPs can also exhibit a broad range of properties. All prepared NPs possessed surface charges ranging from +11.8 to +31.3 mV (Table 2). The NPs with higher percentages of Arg had a higher zeta potential. Micro-environmental hydrophobicity of the PEA NPs was compared using Coomassie Brilliant Blue G-250 (CBB) as a polarity-sensitive probe. A bathochromic shift ($\Delta\lambda$) of absorption peak of CBB indicates an increase in micro-environmental hydrophobicity. NPs with higher Phe/Arg ratio exhibited larger shifts, suggesting higher hydrophobicity (FIGS. 2A and 8). Thus, the NPs with higher Phe/Arg ratios might possess a more compact matrix due to stronger hydrophobic interactions, while those with lower ratios might be less compact due to stronger electrostatic repulsion.

Example 3

Protein Encapsulation Efficiency, Release Kinetics, and Enzymatic Stability

For the quantification of encapsulation efficiency, fluorophore-labeled proteins were used for the preparation of NPs. FITC-labeled insulin and TRITC-labeled BSA were synthesized and purified according to the recommended protocol of the FITC/TRITC supplier (Invitrogen). FITC-labeled Tf (Invitrogen) was used as supplied. For the NP preparation, 10% of the corresponding proteins in the formulation were replaced with fluorescently labeled ones. After the preparation and washing processes, the NP suspension was ultra-centrifuged for 15 min. The pellet was re-suspended in $H_2O$, and then mixed with three-fold volume of DMSO. Fluorescent-labeled protein was measured using a Varioskan Flash Multimode Reader (Thermo Fisher Scientific, USA).

Figure 2B:
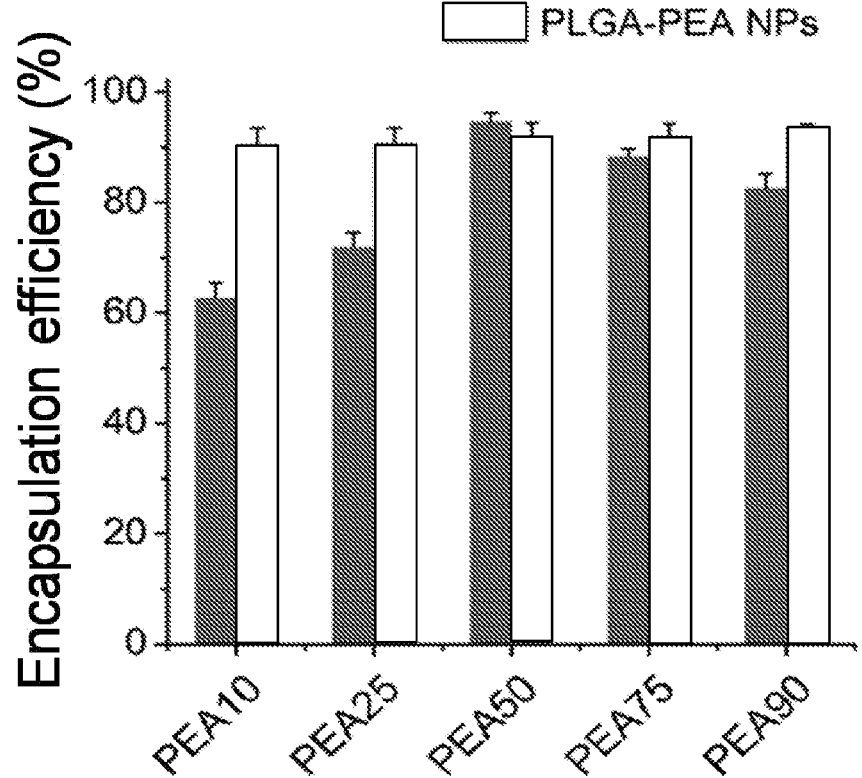
FIG. 2B is a plot of the encapsulation efficiency of interiorly loaded insulin for different NPs.
Figure 2C:
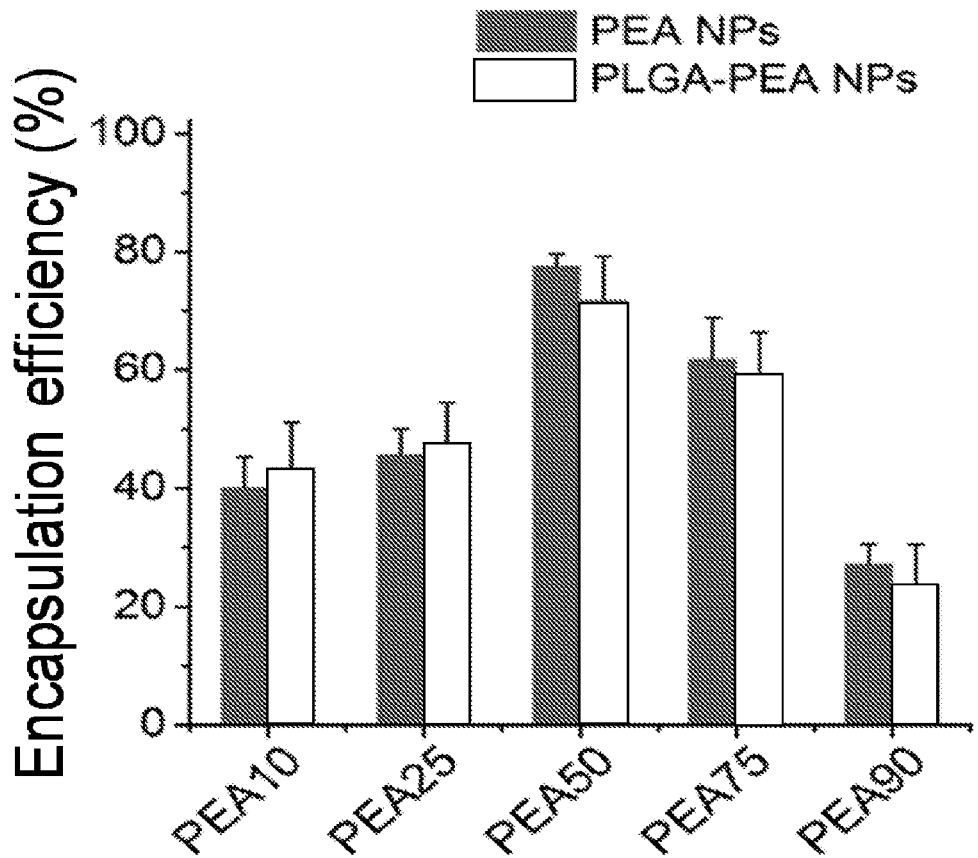
FIG. 2C is a plot of the encapsulation efficiency of surface-loaded Tf for different NPs.
Figure 9A:
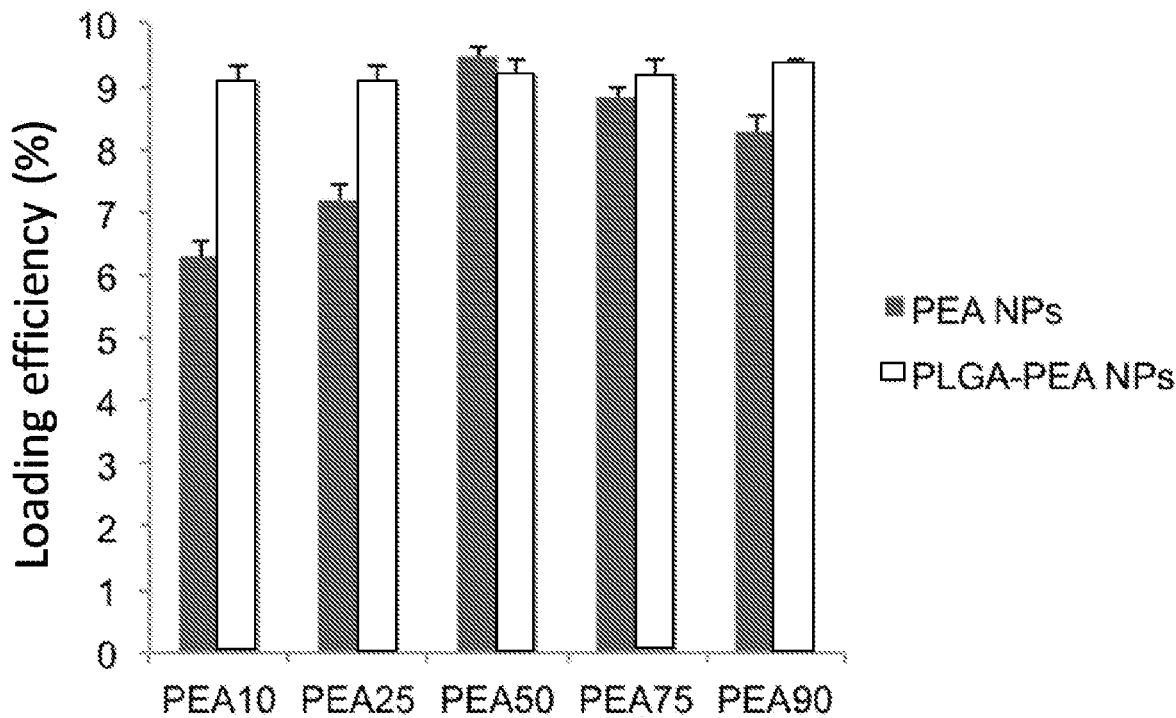
FIG. 9A is a plot of the loading efficiency of insulin into various PEA NPs and PLGA-PEA NPs.
Figure 9B:
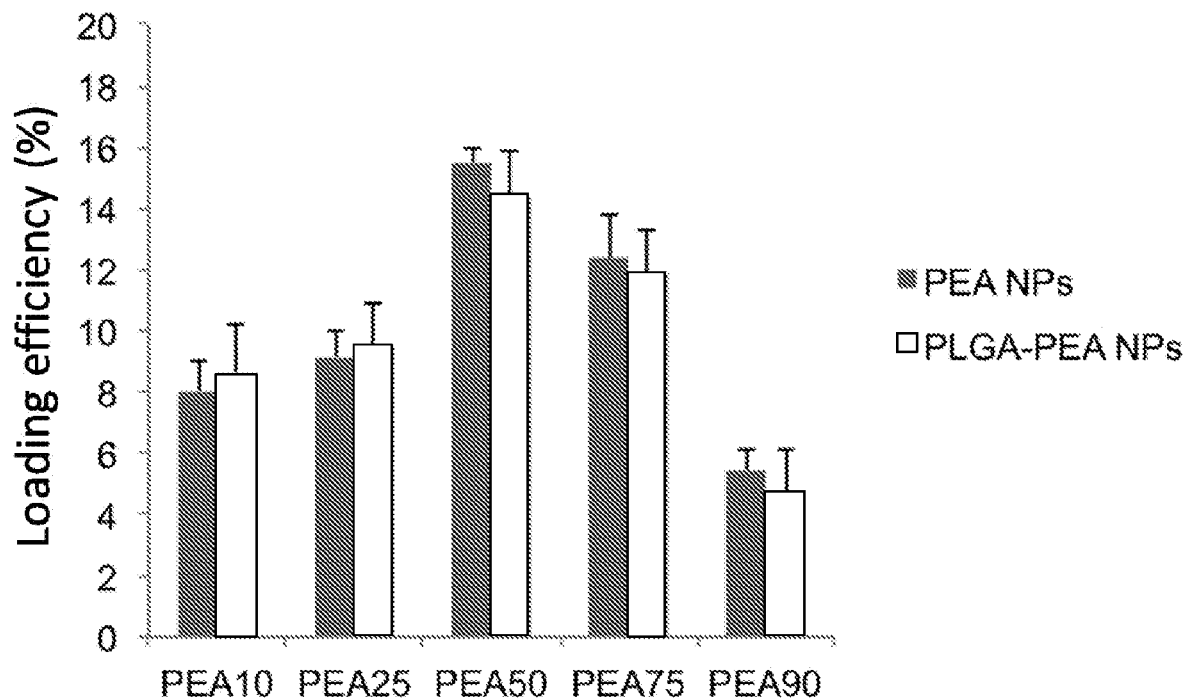
FIG. 9B is a plot of the loading efficiency Tf into various PEA NPs and PLGA-PEA NPs.
Figure 9C:
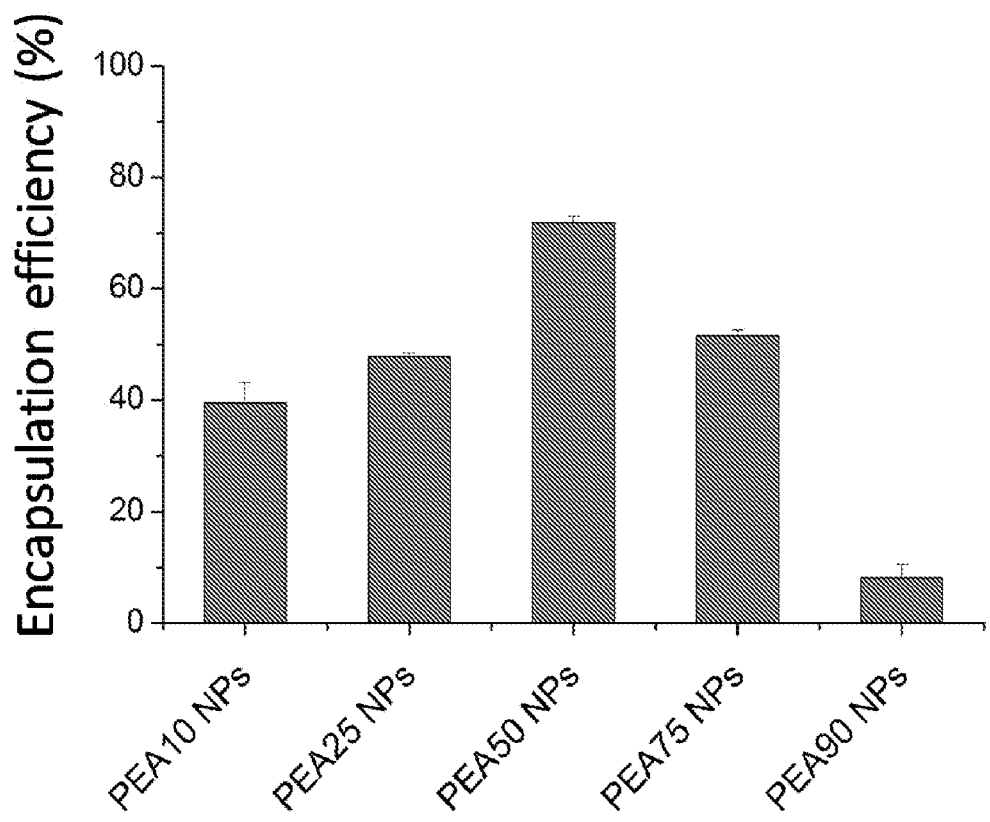
FIG. 9C is a plot of the encapsulation efficiency of BSA into various PEA NPs.

Among all the PEA NPs, PEA50 NPs had the highest EE (~95%) and LE (>9 wt %), while NPs with lower or higher Phe/Arg ratios had lower EE and LE with respect to interiorly loaded insulin (FIGS. 2B and 9A). These findings support the conclusion that that both the cationic and hydrophobic characteristics of PEAs may be important for their interaction with proteins. All PLGA-PEA NPs exhibited similar EE of insulin (~90%). The EE and LE of the surface-loaded Tf are shown in FIGS. 2C and 9B. A similar trend was observed for PEA NPs and PLGA-PEA NPs, thus the surface loading is mainly mediated by the interaction of PEAs with the Tf protein.

Release Kinetics

To determine the release kinetics, FITC-labeled insulin or Alexa-Fluor-488 labeled Tf was used for the NP preparation as described above. A suspension of NPs in PBS was aliquoted (1.5 mL) into semi permeable mini-dialysis tubes (Pierce). Mini-dialysis tubes with MWCO of 100 kDa were used for the insulin release study, and tubes with MWCO of 300 kDa were used for the Tf release study. The samples were dialyzed against frequently renewed PBS (pH 7.4) at 37° C. with gentle stirring. The release kinetics was also evaluated in simulated gastric fluid (SGF, pH=2.0), simulated intestinal fluid (SIF, pH=6.8). Continuous release of insulin in different pH environment was also evaluated by dialyzing the NPs against SGF (pH 2.0) for 2 h, subsequently followed by SIF (pH 6.8) for another 6 h and PBS (pH 7.4) for another 24 h. At a predetermined time, 0.1 mL of sample from within the dialysis tubes were withdrawn, and the NPs were disintegrated with DMSO. The fluorescence intensity of fluorescent-labeled protein was measured as described above. The release of DiD dye from the NPs was studied with the same procedure.

Figure 2D:
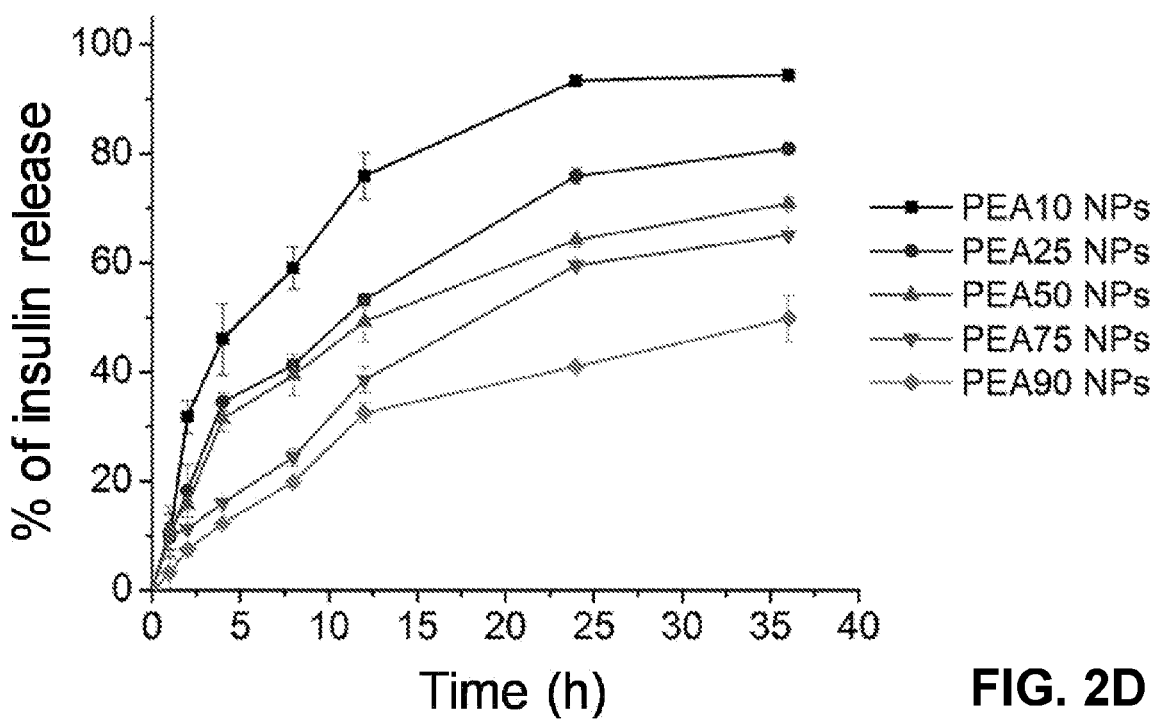
FIG. 2D is a plot of the release profile of insulin from different PEA NPs.
Figure 2E:
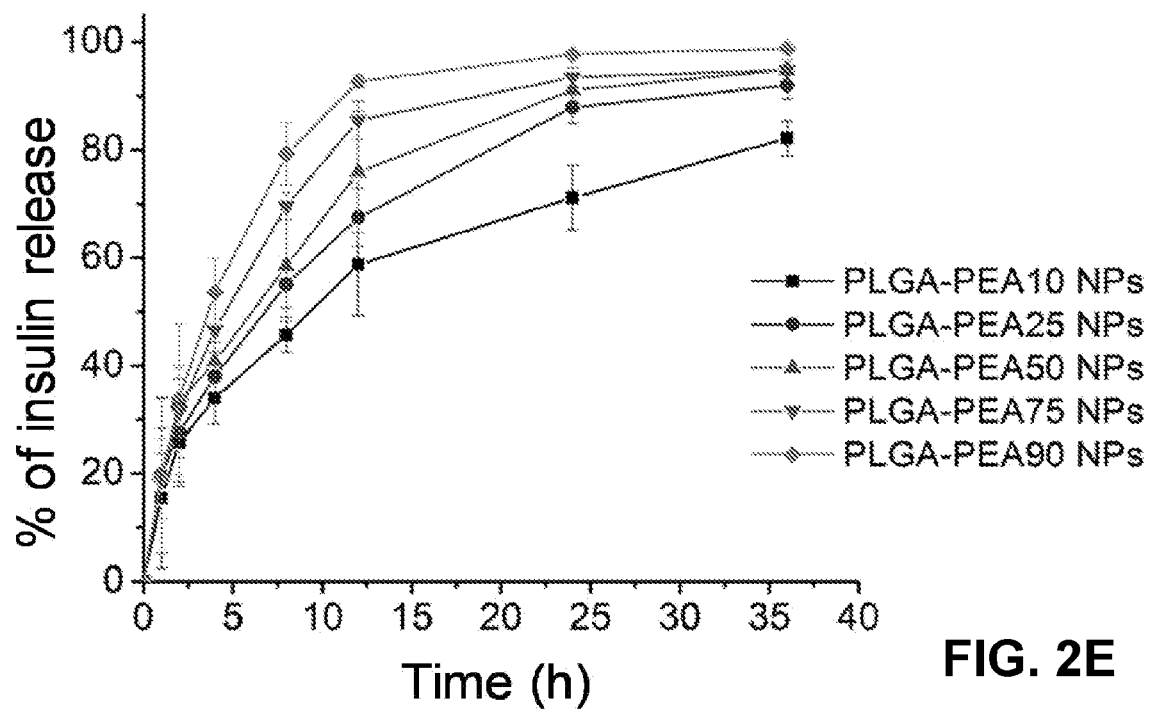
FIG. 2E is a plot of release profile of insulin from different PLGA-PEA NPs.
Figure 10A:
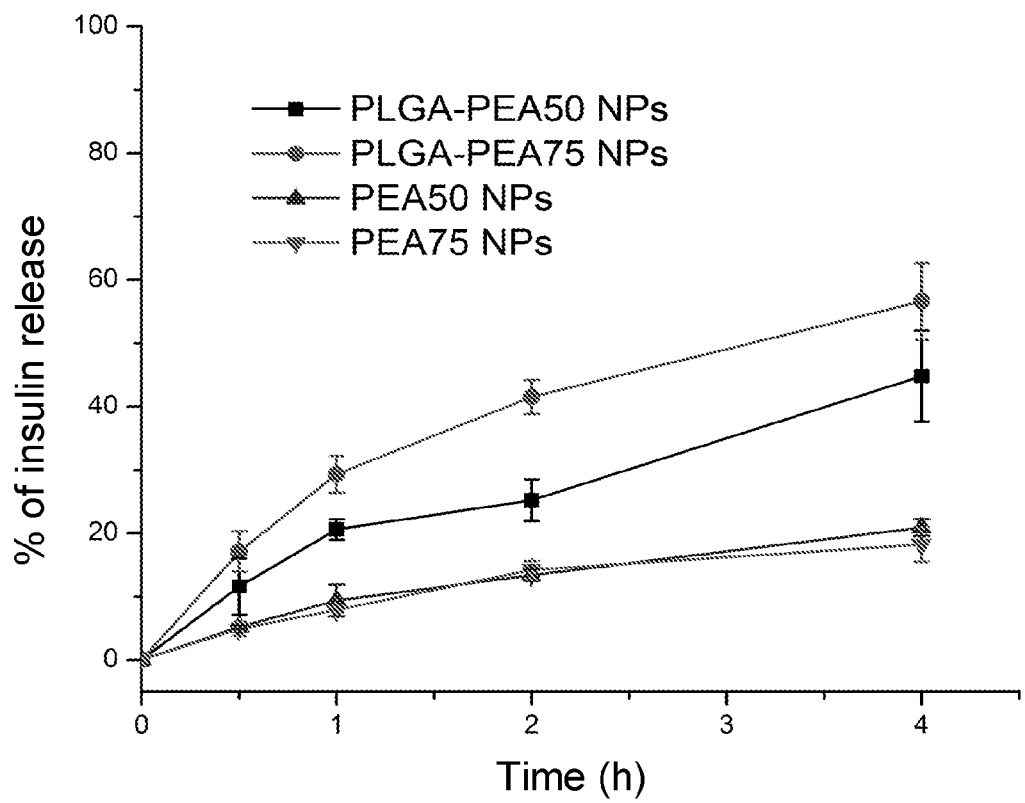
FIG. 10A is a plot of the release profile of insulin in simulated gastric fluid (pH=2.0).
Figure 10B:
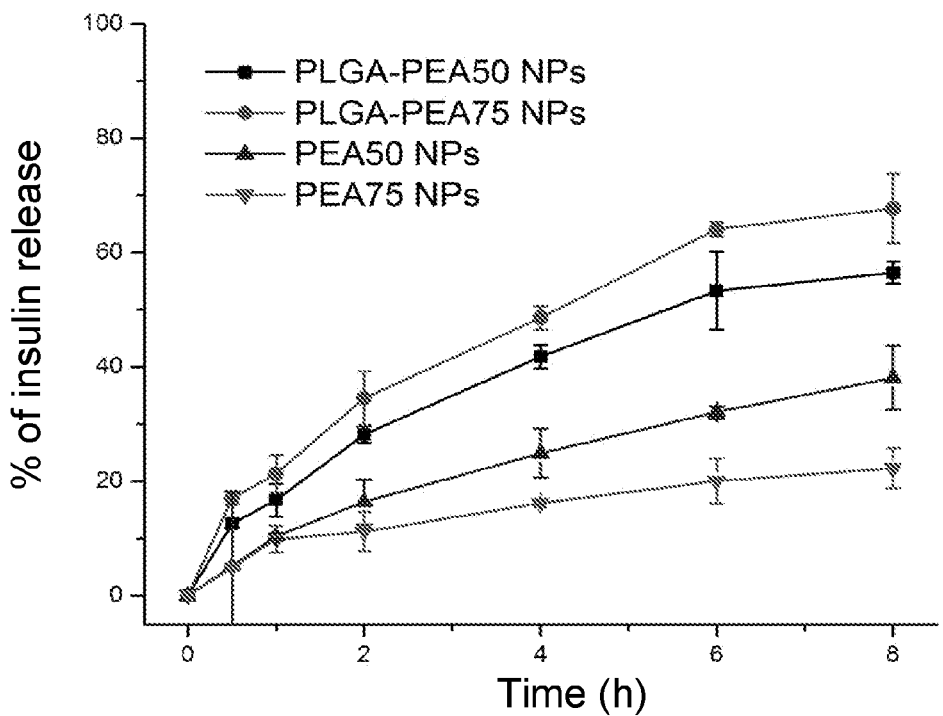
FIG. 10B is a plot of the release profile of insulin at simulated intestinal fluid (pH=6.8) for PEA50 NPs, PEA75 NPs, PLGA-PEA 50 NPs and PLGA-PEA 75 NPs.
Figure 10C:
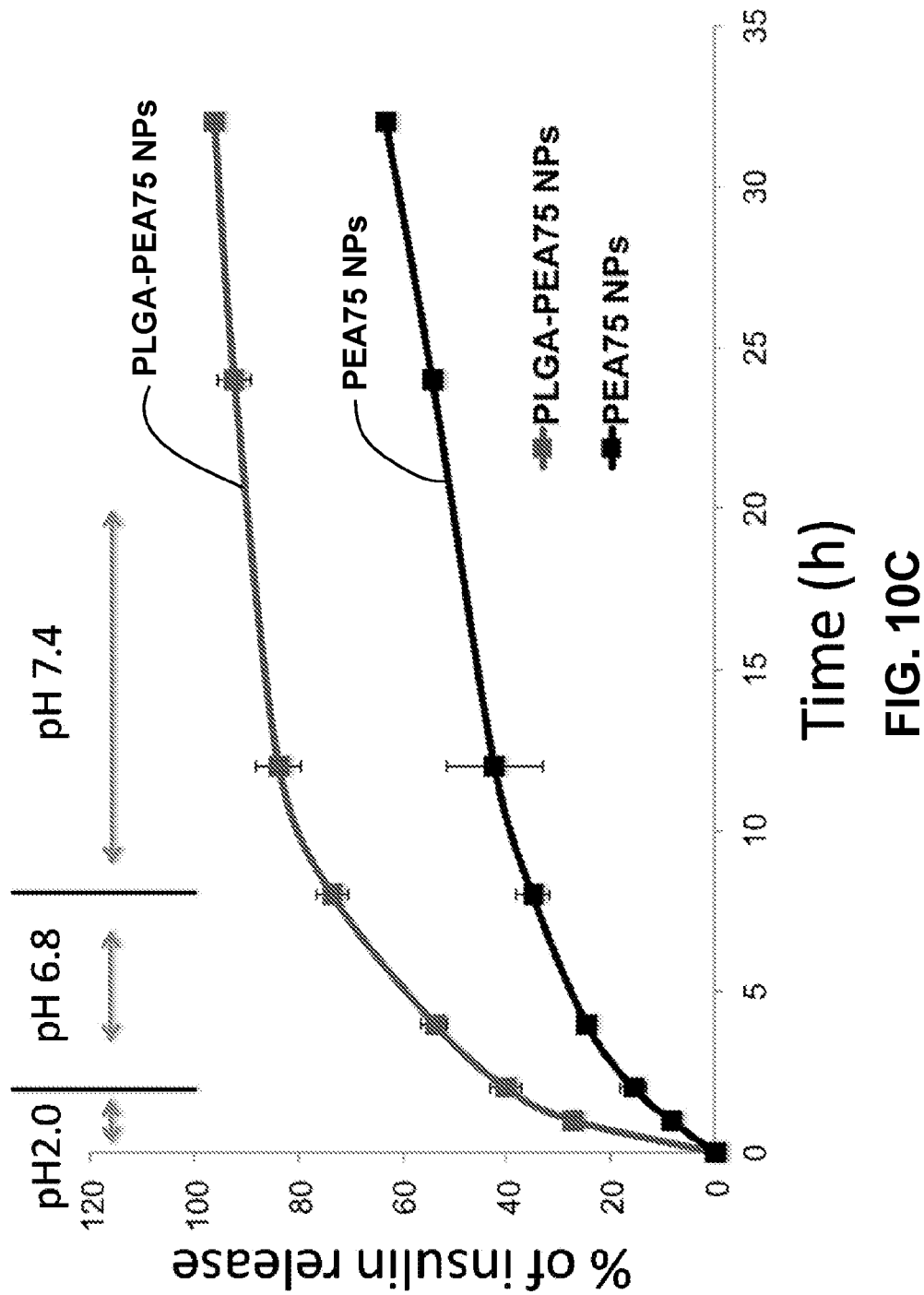
FIG. 10C is a plot of the release profile of insulin at continuous release of insulin in different pH environment by dialyzing the NPs against SGF (pH 2.0) for 2 h, subsequently followed by SIF (pH 6.8) for another 6 h and PBS (pH 7.4) for another 24 h.
Figure 10D:
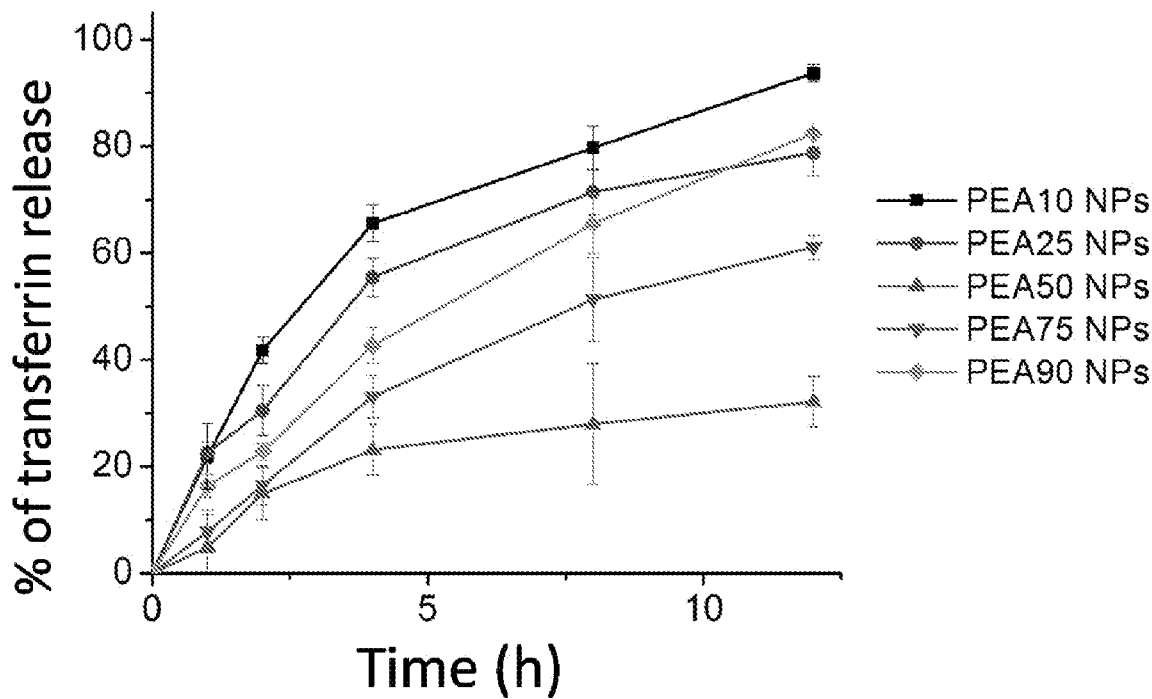
FIG. 10D is a plot of the release profile of Tf from different PEA NPs.
Figure 10E:
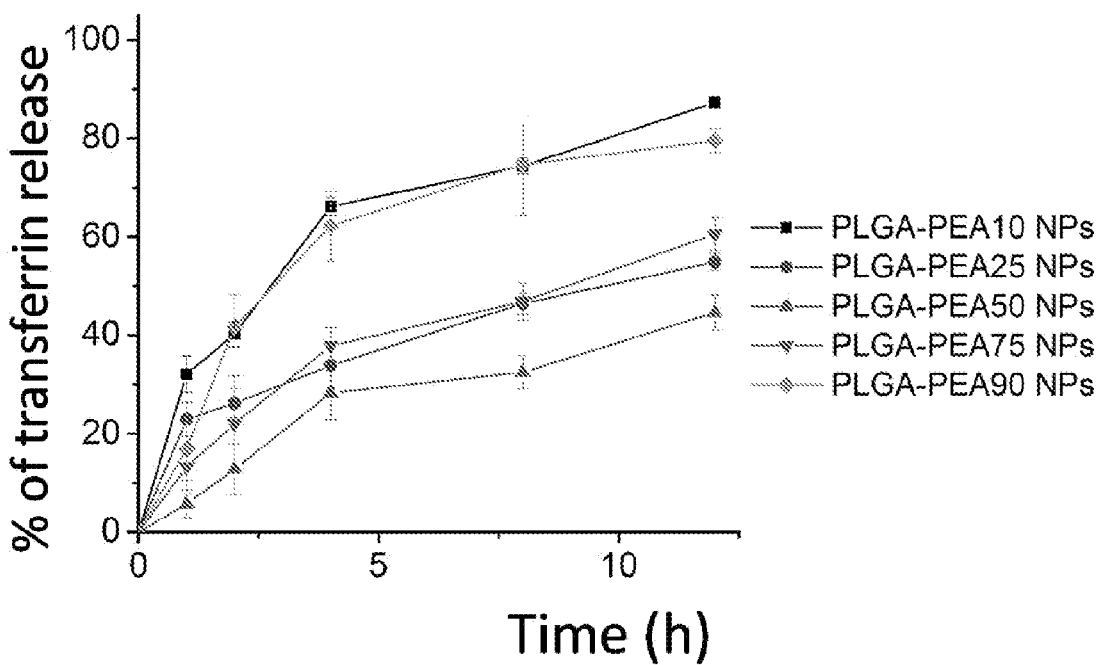
FIG. 10E is a plot of the release profile of Tf from different PLGA-PEA NPs.

The release profiles of insulin from PEA and PLGA-PEA NPs are shown in FIGS. 2D and 2E. For PEA NPs, slower release was observed for NPs with higher Phe/Arg ratio (FIG. 2D). Unexpectedly, the insulin release kinetics exhibited a completely opposite trend for PLGA-PEA NPs as compared to PEA NPs, with the release rate being slower for lower Phe/Arg ratio (FIG. 2E). The cationic characteristic of the PEA might have dual effects in influencing the release of insulin. In PEA NPs, stronger cationic properties can cause less compactness of the NP structure, and thus increasing the diffusion rate of insulin. The positive charge may also slow the release rate due to attraction for the negatively charged insulin. As PLGA might increase the compactness of highly cationic NPs by increasing the hydrophobicity and diluting the charge density, the charge interaction between PEA and insulin could then become the dominant factor in controlling protein release from the PLGA-PEA NPs. The NPs also exhibited sustained release in simulated gastric fluid, simulated intestinal fluid and fluid of different pH at sequential order (FIGS. 10A-10C). In addition, we also investigated the release profile of the surface-loaded Tf from the NPs (FIGS. 10D and 10E). Tf was released most slowly from NPs with PEA50 (either PEA or PLGA-PEA NPs). Since the release of Tf does not involve diffusion through the NP matrix, the release rate may be mainly controlled by the protein interactions with the surface of NPs.

Enzymatic Stability

To evaluate the enzymatic stability of insulin and Tf loaded on the NPs, enzymatic degradation studies of insulin and Tf were performed using simulated intestinal fluid (pH 6.8) with pancreatin (Sigma). To summarize the protocol, 0.2 mL of NP solution or free protein solution was mixed with 2 mL of simulated intestinal fluid containing bile salts (10 mM), lecithin (2 mM), and pancreatin (1 mg/mL), and then incubated at 37° C. Aliquots (100 µl) were withdrawn at specific time intervals, and added to 200 µl of DMSO containing 0.1% trifluoroacetic acid to terminate the enzymatic reaction and break down the NPs. The concentration of insulin or Tf was then quantified by reversed-phase HPLC (Agilent 1200 series, CA, USA). For insulin measurement, separation was achieved on a Diamosil C18 column (150 mm 4.6 mm, 5 mm) with mobile phase of acetonitrile-water (28:72, contained 0.2 M $Na_2SO_4$ and the pH was adjusted to 2.3 with phosphoric acid) and the detection wavelength was set at 214 nm. For Tf measurement, separation was achieved on a Diamosil C18 column (250 mm 4.6 mm, 5 mm), and gradient elution was carried out at a flow-rate of 1.0 ml/min with solvent A (0.1% trifluoroacetic acid (TFA) in deionized water) and solvent B (acetonitrile-water at 80:20), using a 25% B to 50% B linear gradient over a 15 min period. Elutes were monitored at a wavelength of 214 nm.

Figure 11A:
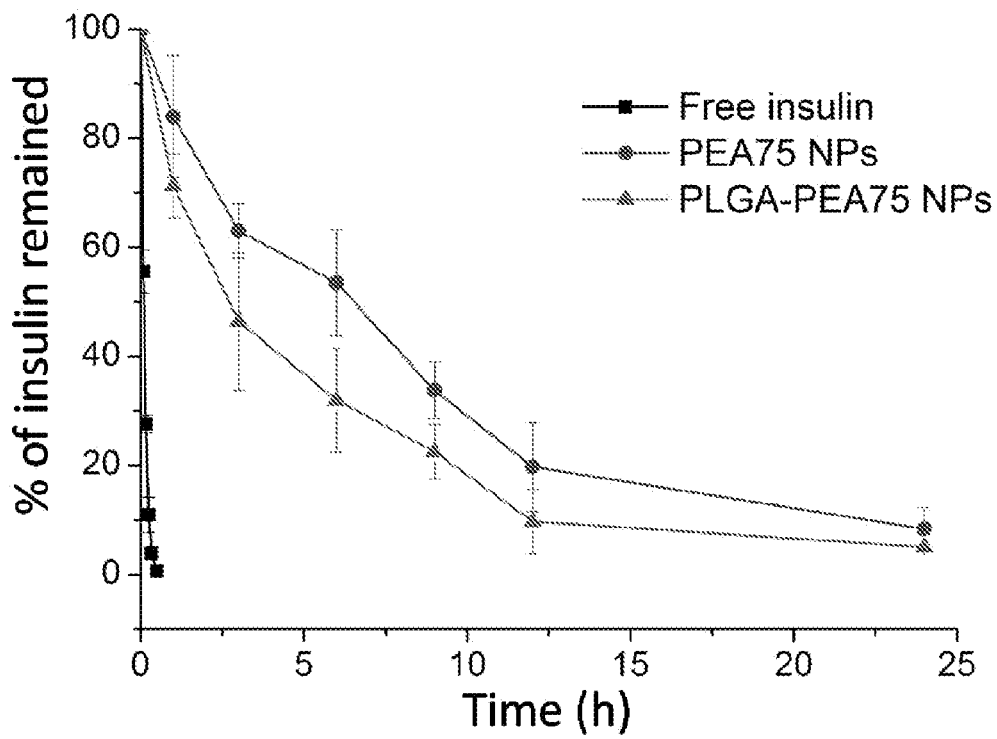
FIG. 11A is a plot of the enzymatic stability of free insulin or insulin encapsulated within PEA75 or PLGA-PEA75 NPs.
Figure 11B:
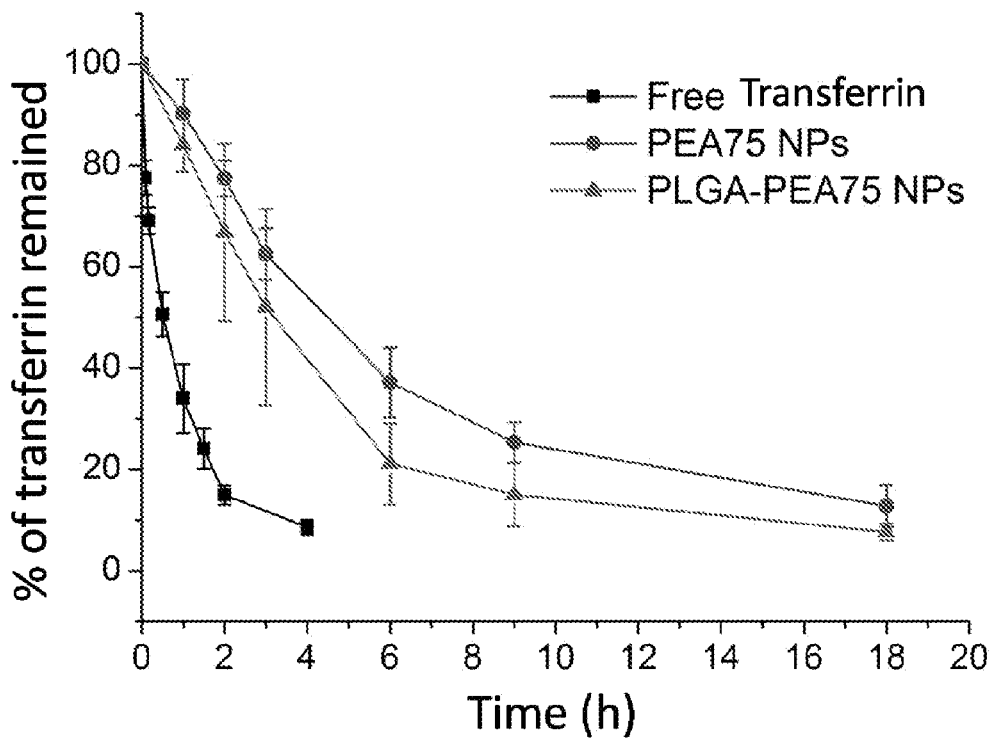
FIG. 11B is a plot of the enzymatic stability of free Tf or Tf loaded on PEA75 or PLGA-PEA75 NPs.

The enzymatic test with pancreatin showed that both insulin and Tf were well protected when loaded with the NPs (FIGS. 11A and 11B).

Example 4

In Vitro Cellular Internalization

For the cellular uptake study, Caco-2 cells were seeded into 96-well plates and cultured for 3 days. After that, the cells were incubated with BSA-, or Tf-coated NPs labeled with DiD, at a polymer concentration of 0.1 mg/mL for 3 hours. The cells were then washed with PBS three times, fixed with 4% paraformaldehyde, and stained with Hoechst (2 µg/ml) for nuclei identification. For the uptake mechanism study with endocytotic inhibitors, Caco-2 were first pre-incubated for 30 minutes with the inhibitors, and then treated with NPs for 3 hours in the presence of inhibitors. 5-(N-ethyl-N-isopropyl) amiloride (EIPA) was used as the macropinocytosis inhibitor, filipin as the caveolae-mediated endocytosis inhibitor, and chlorpromazine as the clathrin-mediated endocytosis inhibitor (Cayman Chemical) (see, e.g., D. Dutta, J. G. Donaldson, Cell Logist 2012, 2, 203-208). Images were acquired on an Inverted Fluorescence Microscope (Zeiss Axiovert 200) and analyzed using Fiji/Image-J software. For the uptake mechanism study with endocytic probes, Caco-2 cells were seeded on cover slips. Uptake experiments were conducted for 1 hour, with the addition of AF488-labeled Tf or AF488-labeled dextran (Life Technologies) (see, e.g., F. Duchardt, M. Fotin-Mleczek, H. Schwarz, R. Fischer, R. Brock, *Traffic* 2007, 8, 848-866). Cells were then stained with Hoechst33342 (2 μg/ml), and live cell images were recorded with an Inverted Fluorescence Microscope (Zeiss Axiovert 200).

Figure 3A:
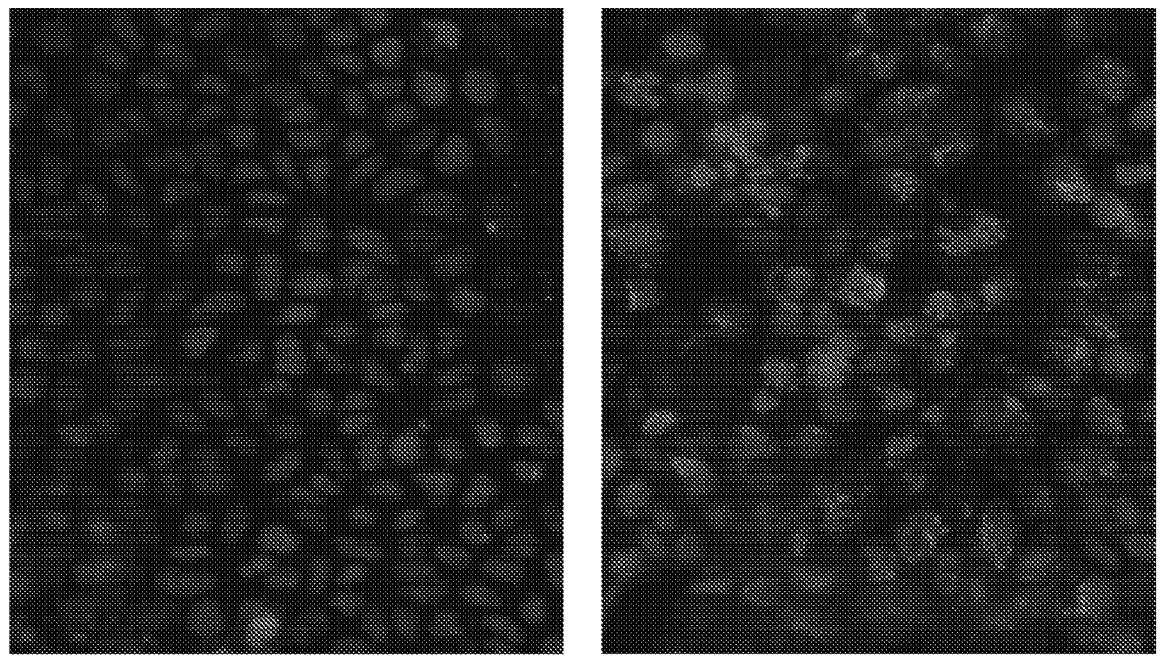
FIG. 3A contains fluorescence images of Caco-2 cells treated with BSA-coated vs. Tf-coated NPs labeled with fluorophore (red).
Figure 3B:
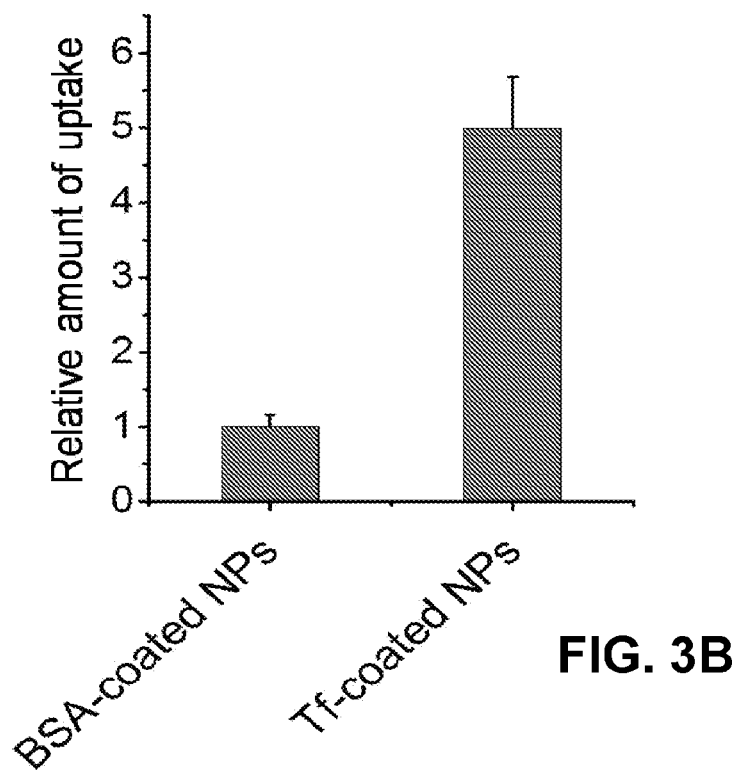
FIG. 3B is a plot of the results of quantitative analysis of the relative uptake of BSA- vs. Tf-coated NPs.
Figure 3C:
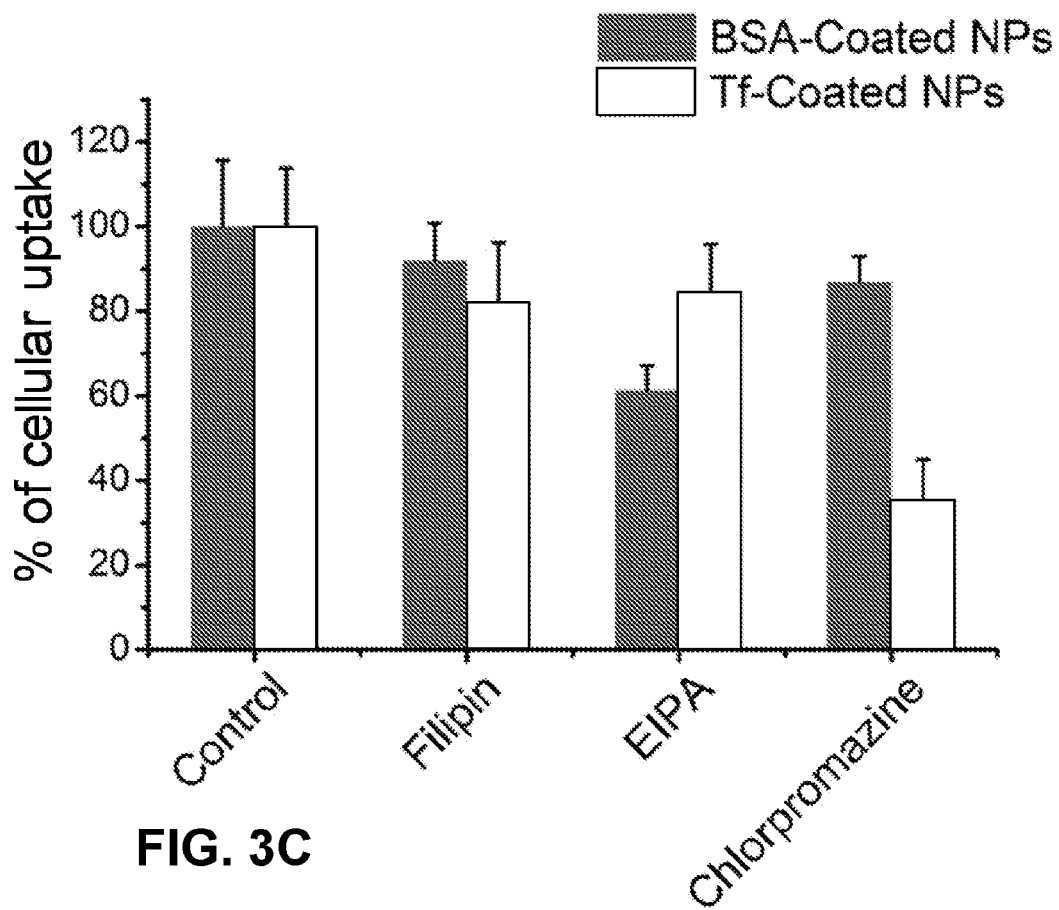
FIG. 3C is a plot of the relative inhibition of NP uptake with specific endocytotic inhibitors (* $p<0.05$ vs. control).
Figure 12:
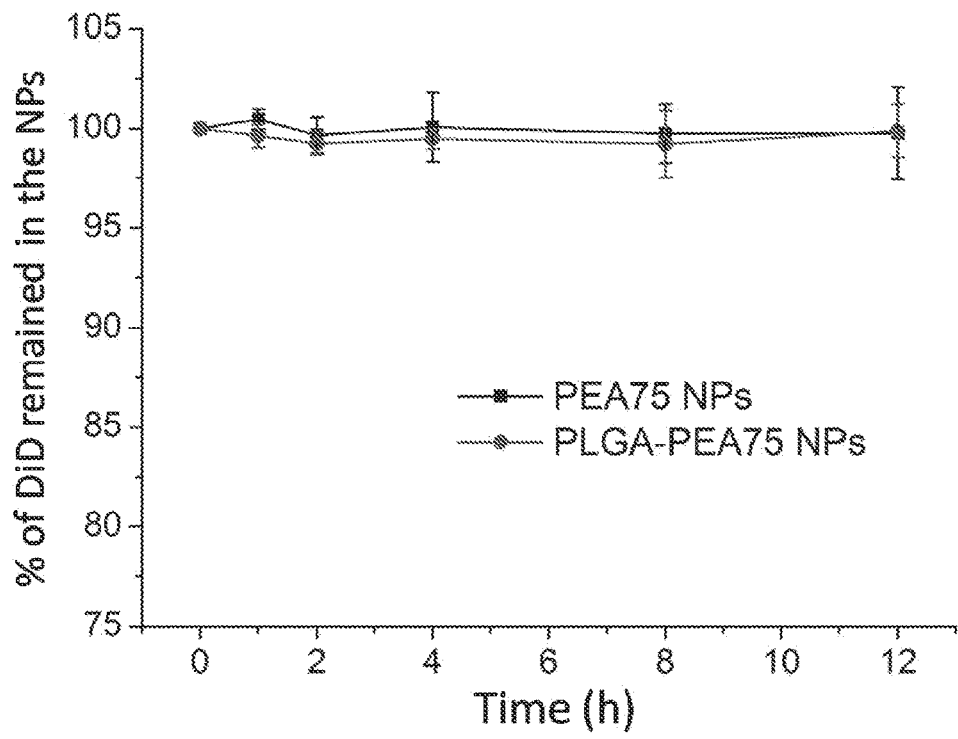
FIG. 12 is a plot of the release profile of DiD from PEA75 or PLGA-PEA75 NPs in cell culture medium within 12 h.

Cellular internalization of Tf-coated NPs was compared with BSA-coated NPs using Caco-2 cells. The PLGA-PEA NPs were loaded with DiD fluorescent dye, which excited no detectable release (FIG. 12). The uptake of Tf-coated NPs was ~5-fold higher than that of BSA-coated NPs (FIGS. 3A and 3B), suggesting the effectiveness of Tf in improving epithelial uptake of NPs. To examine internalization pathway, NPs were incubated with Caco-2 cells in presence of different specific inhibitors: 5-N-ethyl-N-isoproamiloride (EIPA), filipin, and chlorpromazine, for three pathways: macropinocytosis, and caveolae- and clathrin-mediated endocytosis, respectively (see, e.g., J. Zhang, X. Zhu, Y. Jin, W. Shan, Y. Huang, *Mol Pharm* 2014, 11, 1520-1532). The uptake was significantly reduced for BSA-coated NPs only treated with EIPA, indicating a major role of macropinocytosis (FIG. 3C). In comparison, the uptake of Tf-coated NPs was reduced by ~65% with chlorpromazine, inhibitor of clathrin-mediated endocytosis. For further validation, we co-incubated DiD-containing NPs with Alexa Fluor 488 (AF488)-labeled Tf or dextran, which are internalized by clathrin-mediated endocytosis and macropinocytosis, respectively.

Figure 14:
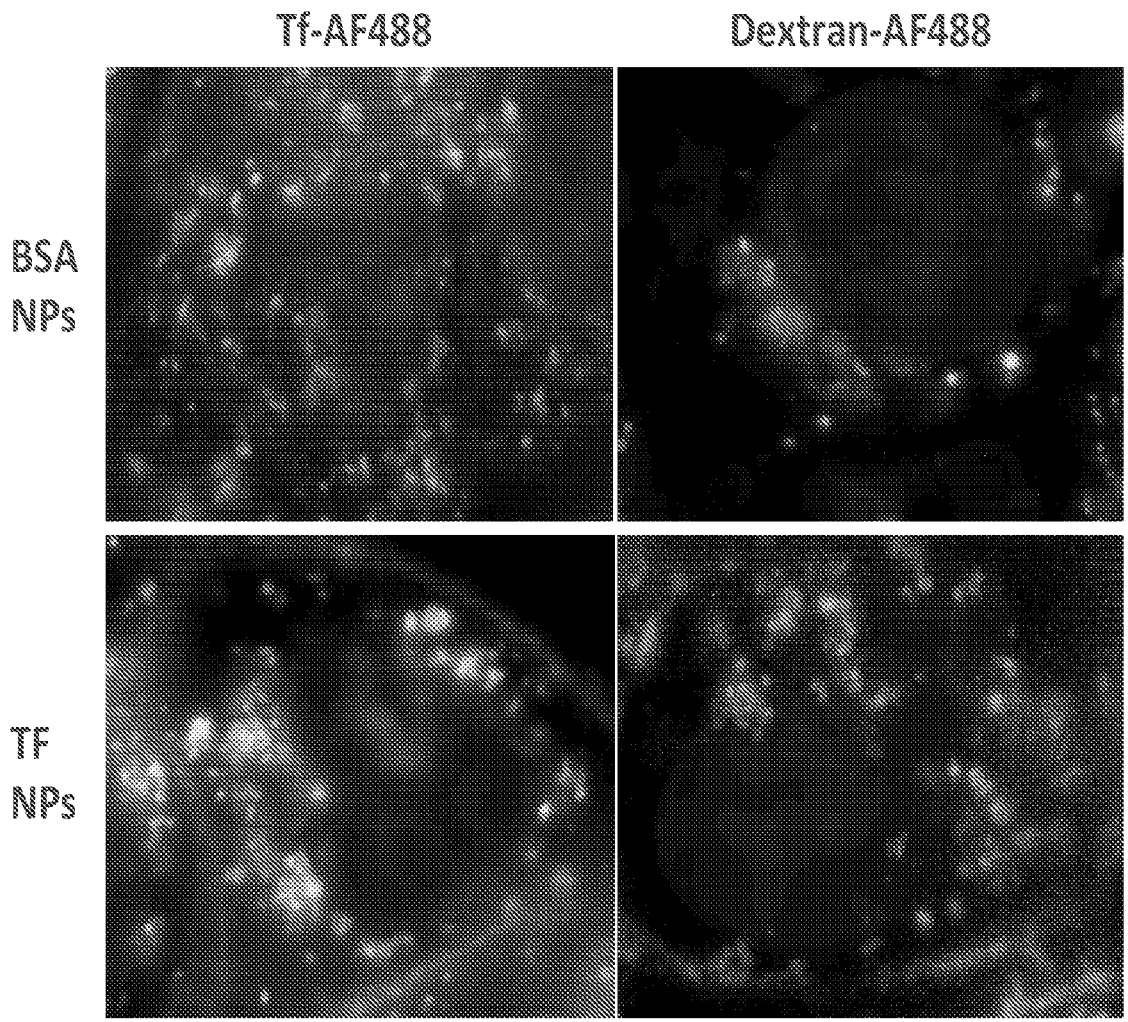
FIG. 14 contains fluorescence images showing co-localization analysis of fluorescently labeled BSA- or Tf-coated NPs (red) with AF488-Tf or AF488-dextran (green). Blue: nucleus.
Figure 15:
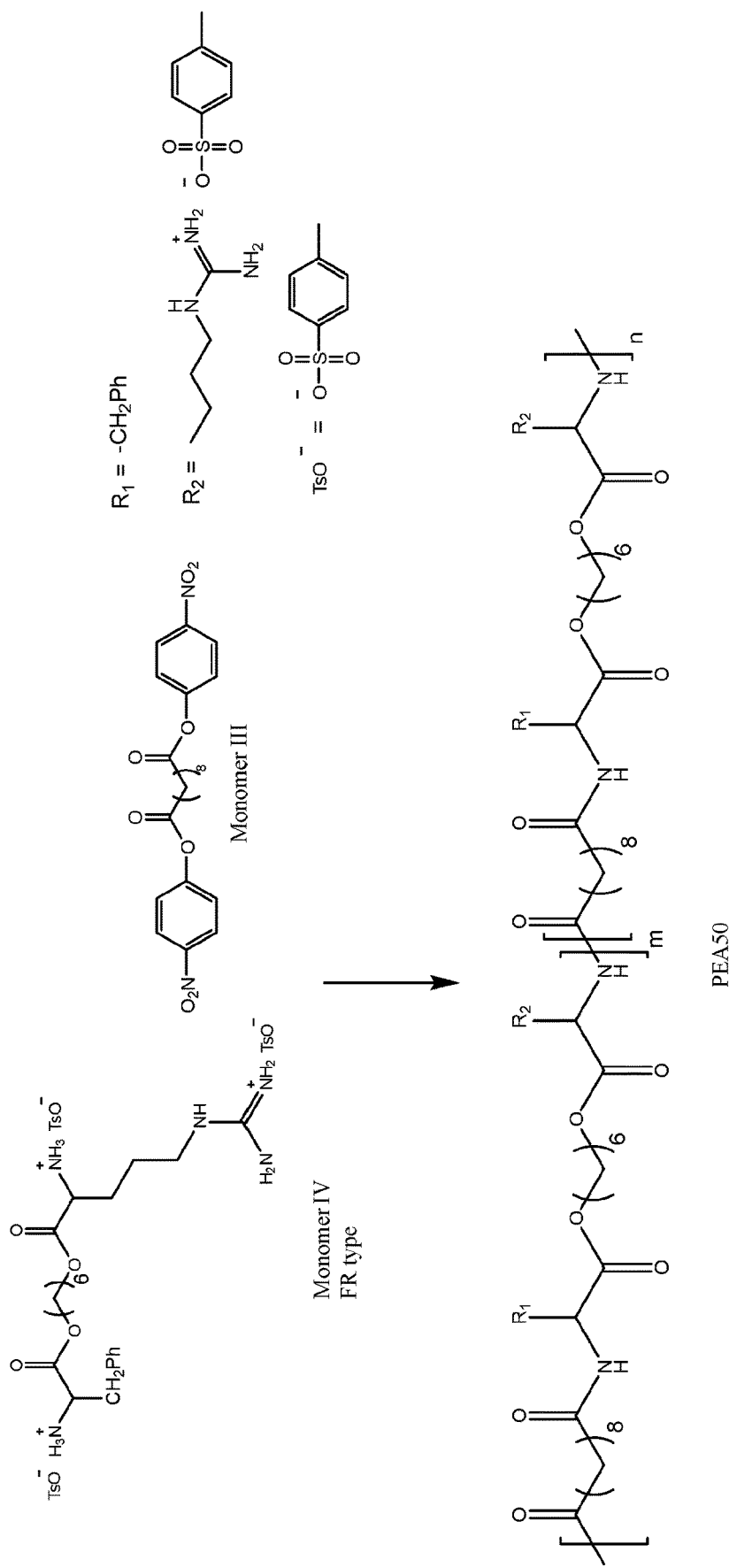
FIG. 15 contains scheme showing synthesis procedures for preparation of PEA50 polymer.
Figure 16:
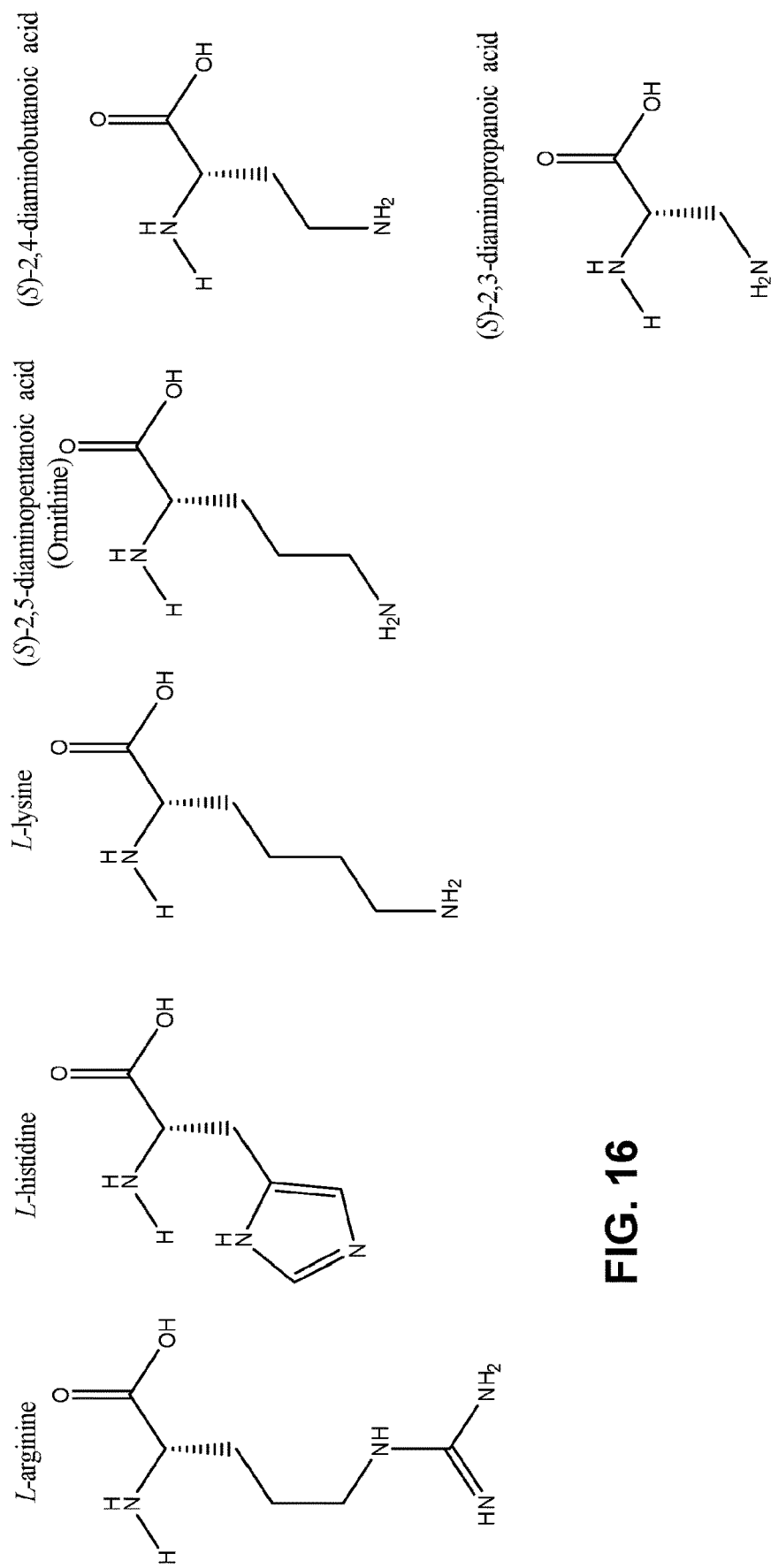
FIG. 16 contains formulae representing the chemical structures of representative natural and unnatural amino acids.

Tf-coated NPs were co-localized with AF488-Tf, whereas BSA-coated NPs were largely co-localized with the AF488-dextran (FIG. 14). Therefore, the Tf enhanced the epithelial internalization of the NPs by changing the uptake pathway via the specific ligand-receptor interaction. FIG. 14 shows co-localization analysis of fluorescently labeled BSA- or Tf-coated NPs (red) with AF488-Tf or AF488-dextran (green). Blue: nucleus. DiD-containing NPs were co-incubated with Alexa Fluor 488 (AF488)-labeled Tf or dextran, which are internalized by clathrin-mediated endocytosis and macropinocytosis, respectively. The internalized Tf-coated NPs were strongly co-localized with AF488-Tf, whereas BSA-coated NPs were largely colocalized with the AF488-dextran.

Example 5

In vitro Transepithelial Transport

Transepithelial transport of the NPs was studied using a Caco-2 cell monolayer, on a Transwell chamber with a polycarbonate membrane (3 μm in pore size, 0.33 cm² of cell growth area, Costar). Cells were seeded on the Transwell plates at a density of 3×10⁴ cells/well and cultured for 14-21 days before use. The monolayer integrity was checked by measuring the transepithelial electrical resistance (TEER) using a Millicell-ER system (Millipore Corporation, Bedford, Mass.), before and at the end of the experiment. Inserts with TEER values in the range of 800-1000 Ω/cm² were used for the transport experiments. Before the experiments, the cells were incubated in serum-free medium and allowed to equilibrate for 30 min at 37° C. The apical solution was then replaced with 100 μL of fluorescence-labeled NPs (at a polymer concentration of 300 μg/mL) in serum-free medium. For the Tf competitive blocking experiment, cells were incubated with Tf-coated NPs in the presence of an excess amount of free Tf (1 mg/mL). The cells were then incubated for 12 hours before measuring the NP concentration in the basolateral chamber. Each experiment was performed in triplicate.

Figure 3D:
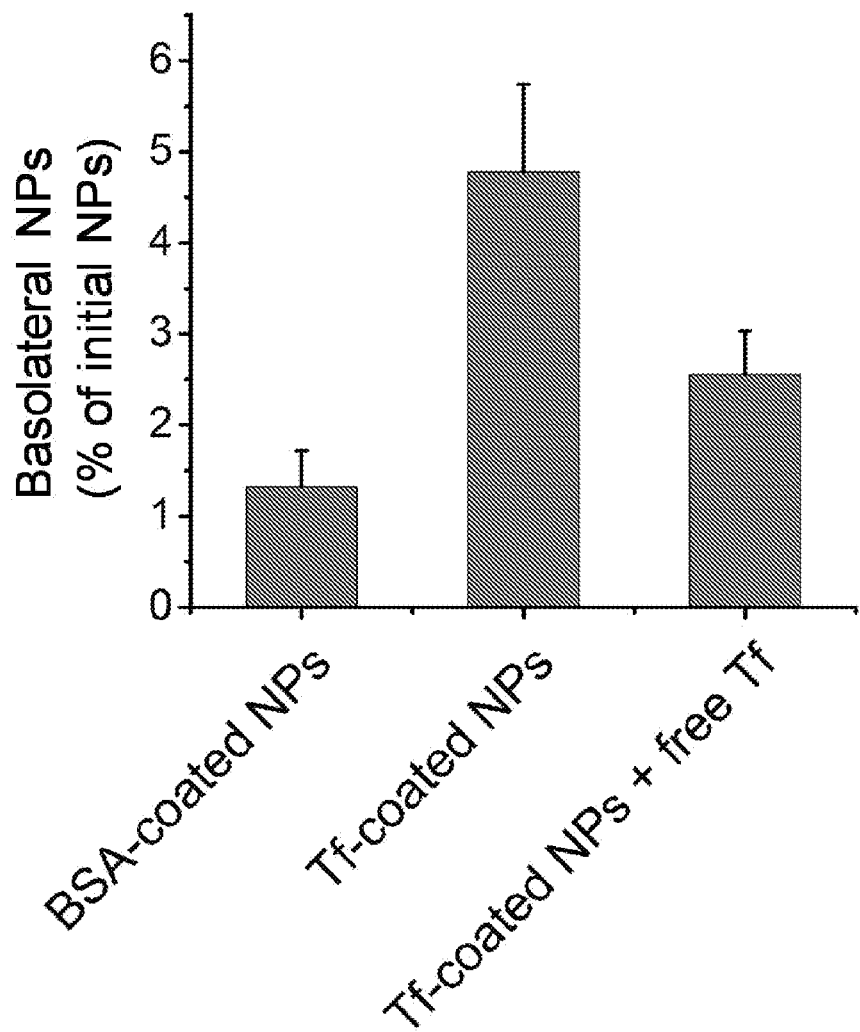
FIG. 3D is a plot of in vitro transepithelial transport of BSA- and Tf-coated NPs, and Tf-coated NPs with free Tf as a competitive blocking agent (n=4 per group).
Figure 13:
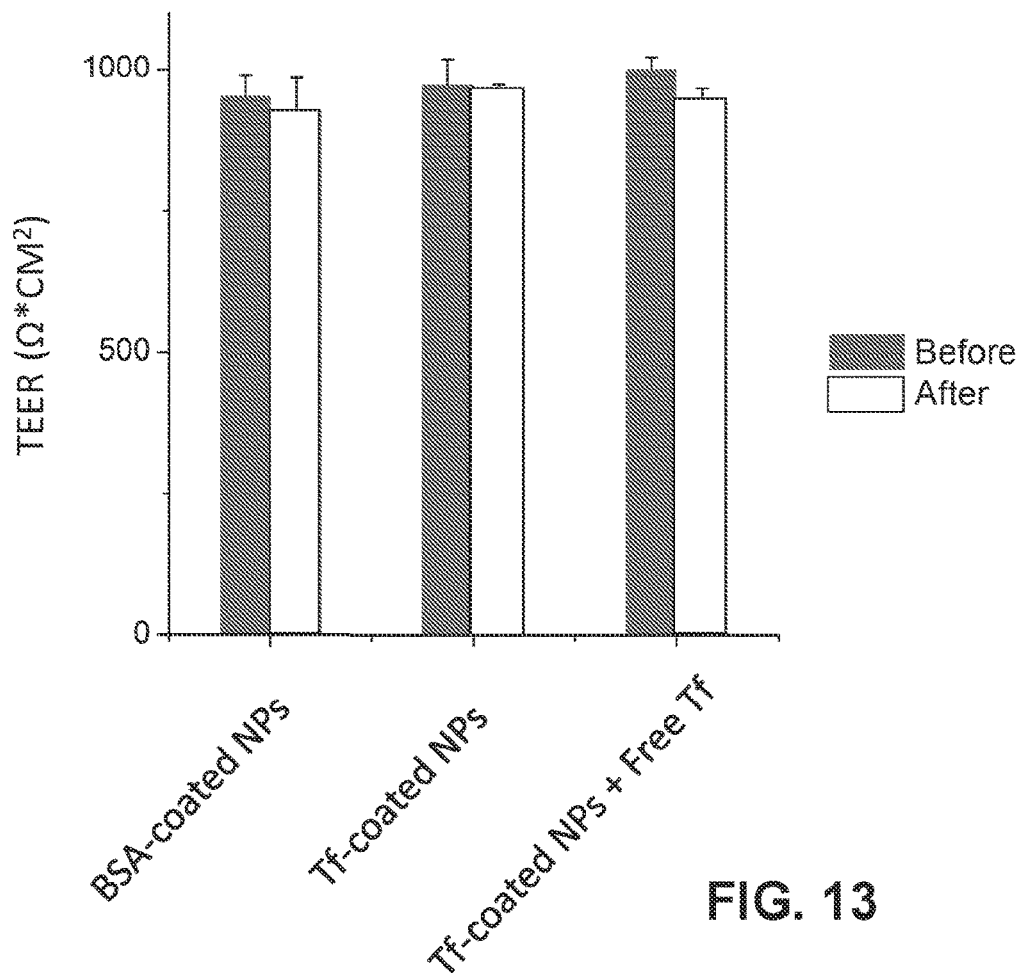
FIG. 13 is a plot of the transepithelial electrical resistance (TEER) values of the cell monolayers before and after the treatment of different samples.

In vitro transepithelial activity of NPs was evaluated by measuring their transport from apical to basolateral side of Caco-2 cell monolayers on Transwell® permeable supports. 4-fold greater fluorescence intensity was observed for Tf-coated NPs relative to BSA-coated NPs (FIG. 3D). Moreover, the amount of basolateral Tf-coated NPs was significantly reduced when co-incubated with free Tf as a competitive blocking agent. Thus, Tf in the outer layer of the nanoparticle plays important role in the transport of NPs. Besides, the NP treatment did not affect the integrity of the cell monolayer (see FIG. 13), thus the NP treatment of the cells didn't damage the cells (see, e.g., E. M. Pridgen, F. Alexis, T. T. Kuo, E. Levy-Nissenbaum, R. Karnik, R. S. Blumberg, R. Langer, O. C. Farokhzad, Sci. *Transl. Med.* 2013, 5, 213ra167). The TEER values of the cell monolayers were unaltered after treatment with BSA- or Tf-coated NPs, which means the NPs did not compromise the integrity of the cell monolayer during transport. Consequently, Tf-coated NPs can be successfully transported across the epithelium while avoiding the potential safety issues associated with the altering the permeability of the epithelium.

Example 6

In Vivo Transepithelial Transport

Figure 4A:
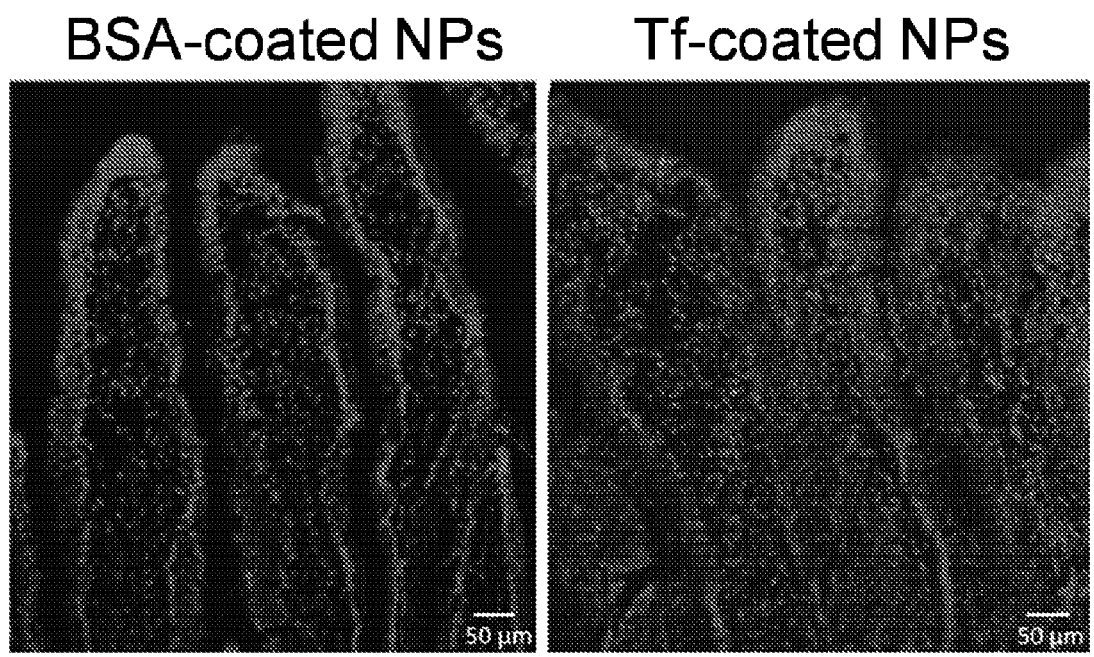
FIG. 4A contains fluorescence images of sections of mouse intestine after administration of BSA- or Tf-coated NPs (red). Cell nuclei were stained with DAPI (blue).

In vivo transport of Tf-coated NPs across intestinal epithelium of mouse was tested. FIG. 4A shows representative images of intestine sections. Advantageously, for the Tf-coated NPs, fluorescence signals were observed in epithelium and basolateral side of epithelial cells, indicating the successful transport of the NPs. Little signal of BSA-coated NPs was detected in the villi.

In Vivo Fluorescence Imaging of Nanoparticles

BALB/c mice (Dashuo Laboratory Animal Center) (n=3) were fasted overnight before experiments. Fluorescently labeled BSA-NPs and Tf-NPs (PLGA-PEA75 NPs prepared with Alexa Fluor 647 labeled PLGA) were administered to the mice by oral gavage. After 1.5 hour, the mice were euthanized with pentobarbital sodium (0.04 mg/kg). Intestinal tissue sections (jejunum) were frozen in Tissue-Tek OCT with liquid nitrogen. Cross sections of the tissue were obtained using a Leica CM1900 cryostat with a thickness of 12 μm. The tissue was then fixed with 4% PFA, stained with DAPI for nucleus detection, and visualized using confocal laser scanning microscopy (FV1000, Olympus, USA).

Example 7

Insulin Bioactivity

To study the bioactivity of insulin after the preparation and drug release process, NPs were allowed to release insulin in PBS for 2 hours at 37° C. Then the NPs were isolated from the released insulin by ultra-centrifugation. Sprague Dawley rats (Dashuo Laboratory Animal Center) (n=4 per group) were fasted overnight, and then administered the released insulin (2 U/kg) or original free insulin (2 U/kg) and saline, by subcutaneous injection. Blood glucose levels were measured with the AlphaTRAK blood glucose monitoring system (Abbott).

Figure 4B:
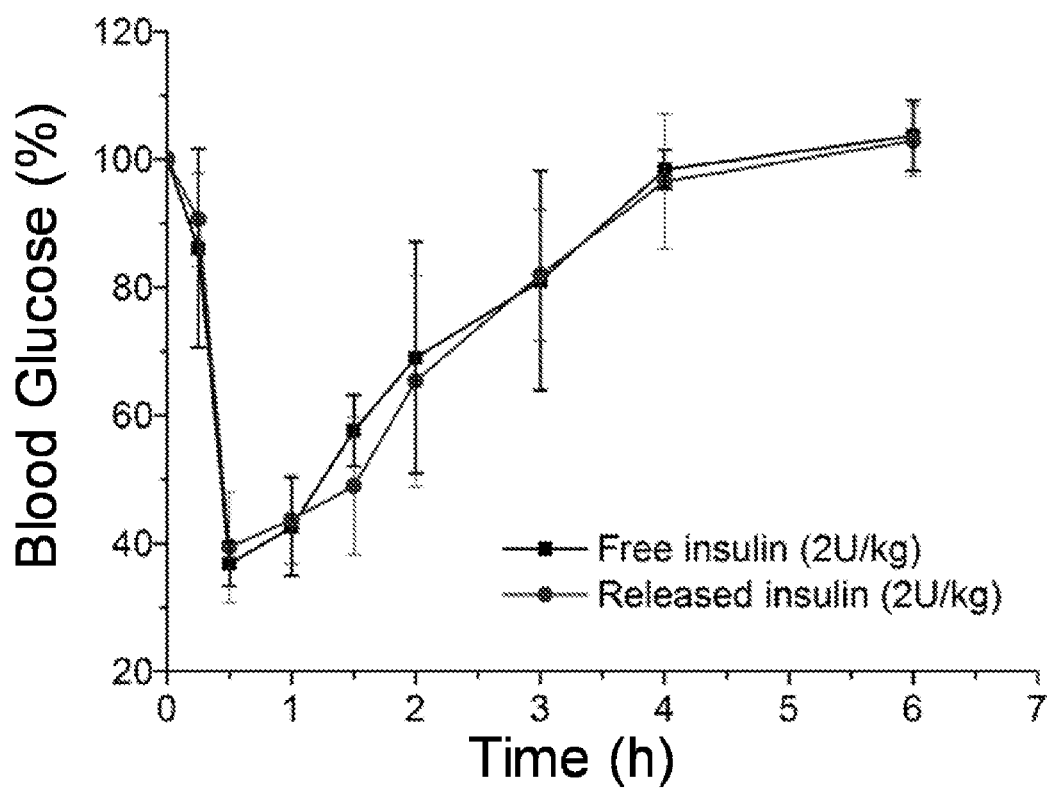
FIG. 4B is a plot of the blood glucose response of normal rats to free insulin or insulin released from the NPs (2 U/kg) (n=4).

The hyperglycemic effect, following the oral administration of insulin-loaded NPs, was tested on normal rats and diabetic mice. FIG. 4B indicated that the released insulin generated a hypoglycemic response analogous to an equivalent dose of free insulin solution after subcutaneous injection.

In Vivo Efficacy—Normal Rats

Figure 4C:
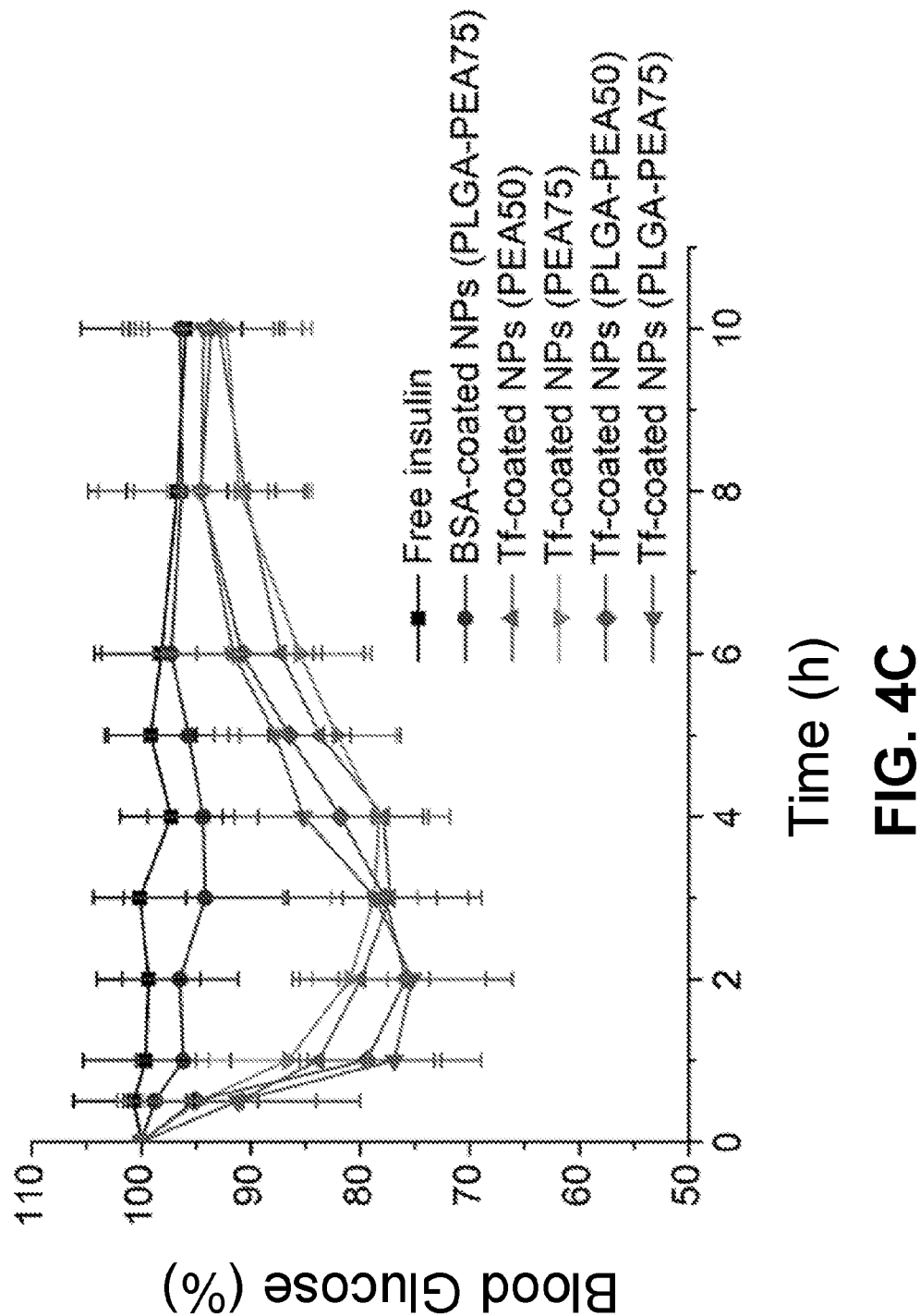
FIG. 4C is a plot of the blood glucose response of normal rats to free insulin solution, BSA-coated NPs, and Tf-coated NPs with different formulations following oral gavage (n=6).
Figure 4D:
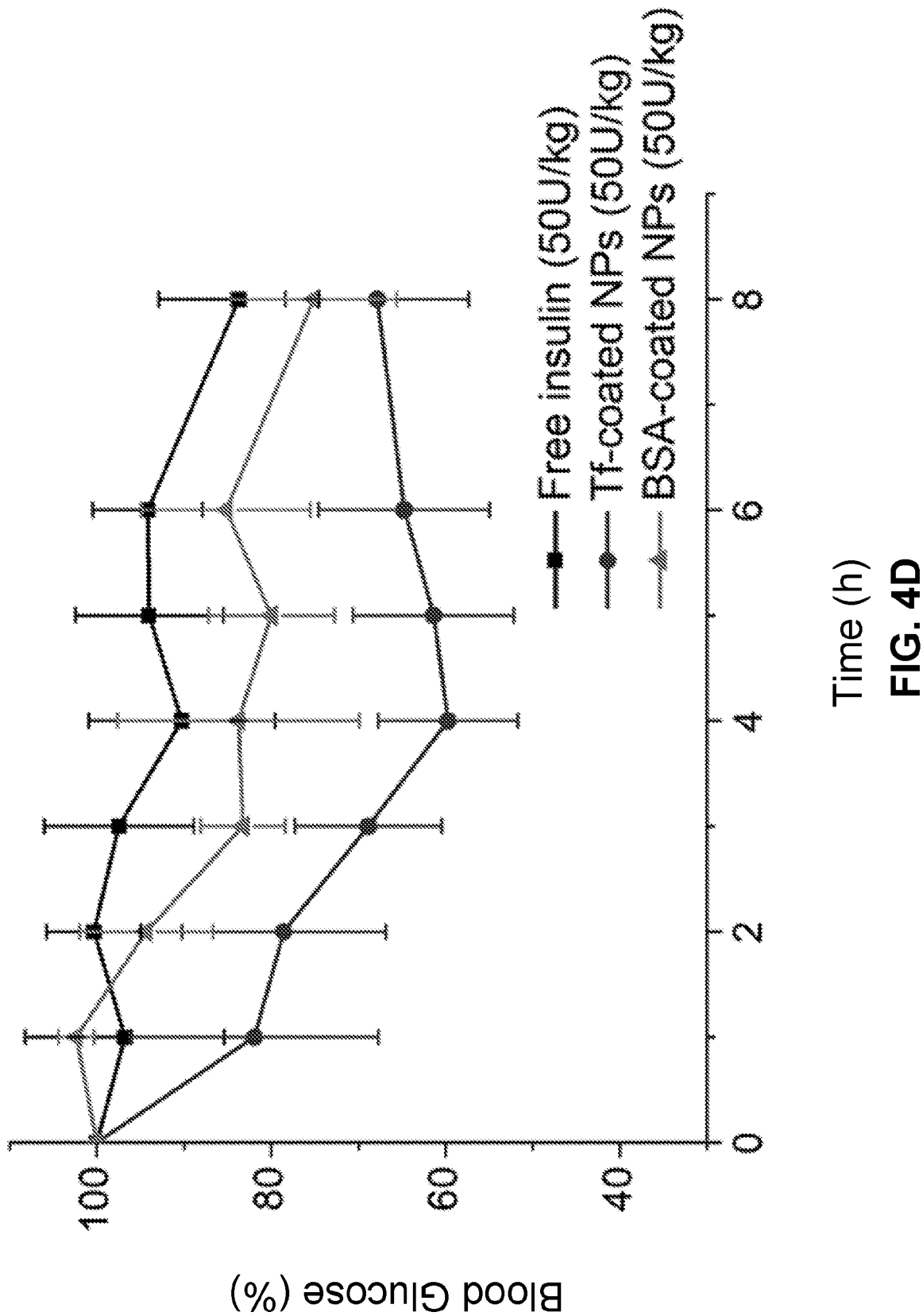
FIG. 4D is a plot of the blood glucose response of diabetic mice to free insulin solution, BSA-coated NPs, and Tf-coated NPs following oral administration (n=6, *$p<0.05$ vs. free insulin).

Sprague Dawley rats (n=6 per group) were fasted overnight before experiments, but allowed free access to water. The animals were administered Tf-coated NPs and BSA-coated NPs (PEA75) in PBS (1.5 mL per 100 g of body weight), at an insulin dose of 50 U/kg, by oral gavage. Tf-coated NPs were tested with four different formulations, including PEA50 NPs, PEA75 NPs, PLGA-PEA50 NPs, and PLGA-PEA75 NPs. As controls, saline and free insulin (50 U/kg) were administered by oral gavage. One group of animals was administered with insulin solution (2 U/kg) by subcutaneous (SC) injection, which was used for the calculation of relative pharmacological availability (PA %). The blood glucose levels were measured as described above, and the pharmacological availability for different formulations was calculated relative to the SC route. The hypoglycemic effect generated by BSA-coated NPs was not significantly different from free insulin (FIG. 4C). All four tested Tf-coated NPs elicited a significant hypoglycemic response, reducing glucose during the first 1-6 hours after administration as shown in Table 3.

TABLE 3

Pharmacodynamic parameters of different samples in normal rats.

| Samples | Route | Dose (U/kg) | Tmax (h) | AAC (%*h) | PA (%) |
|---|---|---|---|---|---|
| Tf-coated NPs (PEA50) | Oral | 50 | 3 | 125.5 | 5.41 |
| Tf-coated NPs (PEA75) | Oral | 50 | 4 | 122.7 | 5.29 |
| Tf-coated NPs (PLGA-PEA50) | Oral | 50 | 2 | 109.7 | 4.73 |
| Tf-coated NPs (PLGA-PEA75) | Oral | 50 | 2 | 106.7 | 4.60 |
| BSA-coated NPs(PLGA-PEA75) | Oral | 50 | 1 | 20.4 | 0.88 |
| Free Insulin | Subcutaneous injection | 2 | 0.5 | 92.8 | 100.0 |

AAC: area above the serum glucose concentration curve; PA: relative pharmacological availability.

It is worth noting that, despite the lasting of insulin release, the glucose levels in all these NP groups exhibited no significant difference relative to the control group at 8-10 hours post administration, which might be attributed to the systemic clearance of the NPs.

In Vivo Efficacy—Diabetic Mice

Hypoglycemic effect was also tested on mice with insulin-dependent (type I) diabetes mellitus.

For the evaluation of in vivo efficacy in diabetic animals, insulin-dependent (type 1) diabetes was induced in male BALB/c mice (Charles River Laboratories) by a single injection of streptozotocin solution (70 mg/ml) as previously described (see, e.g., 7. S. Arora, S. K. Ojha, D. Vohora, Global J. Pharmacol. 2009, 3, 81-84). Animals were considered to be diabetic if they had fasting glycemia higher than 16.0 mM one week after the injection. The diabetic mice (n=6 per group) were fasted overnight and then administered different samples by gavage, including saline, free insulin, Tf-coated NPs (PEA75), and BSA-coated NPs (PEA75) (insulin dose of 50 U/kg, 1.5 mL per 100 g of body weight). One group of animals was administered an insulin solution (5 U/kg) by subcutaneous (SC) injection. The blood glucose levels were measured as described above, and the pharmacological availability for different formulations was calculated relative to the SC route.

BSA-coated NPs only led to a mild hypoglycemic response with no significant difference from the control. Tf-coated NPs elicited a remarkable hypoglycemic response at the dose of 50 U/kg as shown in Table 4.

TABLE 4

Pharmacodynamic parameters of different samples in diabetic mice.

| Samples | Route | Dose (U/kg) | Tmax (h) | AAC (%*h) | PA (%) |
|---|---|---|---|---|---|
| Tf-coated NPs (PEA75) | Oral | 50 | 5 | 177.9 | 7.8 |
| BSA-coated NPs(PEA75) | Oral | 50 | 5 | 46.7 | 2.1 |
| Free Insulin | Subcutaneous injection | 5 | 1 | 227.5 | 100.0 |

AAC: area above the serum glucose concentration curve; PA: relative pharmacological availability.

Example 8

Characterization of Ala-Arg Nanoparticles

The Ala-Arg nanoparticles were prepared as described in Example 1b. Encapsulation efficacy (EE %) and loading efficacy (LE %) of the nanoparticles prepared from the Ala-Arg polymers with respect to BSA and docetaxel payloads are summarized in Tables 5a, 5b and 5c.

TABLE 5a

Protein loading capability (inside NP), 20 wt. % BSA was used

| | Encapsulation Efficacy (EE %) | Loading Efficacy (LE %) |
|---|---|---|
| Ala-Arg-10 | 85% | 17% |
| Ala-Arg-25 | 85% | 17% |
| Ala-Arg-50 | 90% | 18% |
| Ala-Arg-75 | 80% | 16% |
| Ala-Arg-90 | 75% | 15% |

TABLE 5b

Protein loading capability (on NP surface), 10 wt % BSA was used

| | Encapsulation Efficacy (EE %) | Loading Efficacy (LE %) |
|---|---|---|
| Ala-Arg-10 | 30% | 6% |
| Ala-Arg-25 | 35% | 7% |
| Ala-Arg-50 | 50% | 10% |
| Ala-Arg-75 | 60% | 12% |
| Ala-Arg-90 | 65% | 13% |

TABLE 5c

Docetaxel (DTX) loading capability (inside NP), 20 wt % DTX and 20% BSA were used

| | Encapsulation Efficacy (EE %) | Loading Efficacy (LE %) |
|---|---|---|
| Ala-Arg-10 | 30% | 6% |
| Ala-Arg-25 | 35% | 7% |

TABLE 5c-continued

Docetaxel (DTX) loading capability (inside NP), 20 wt % DTX and 20% BSA were used

|  | Encapsulation Efficacy (EE %) | Loading Efficacy (LE %) |
|---|---|---|
| Ala-Arg-50 | 50% | 10% |
| Ala-Arg-75 | 60% | 12% |
| Ala-Arg-90 | 65% | 13% |

Figure 18:
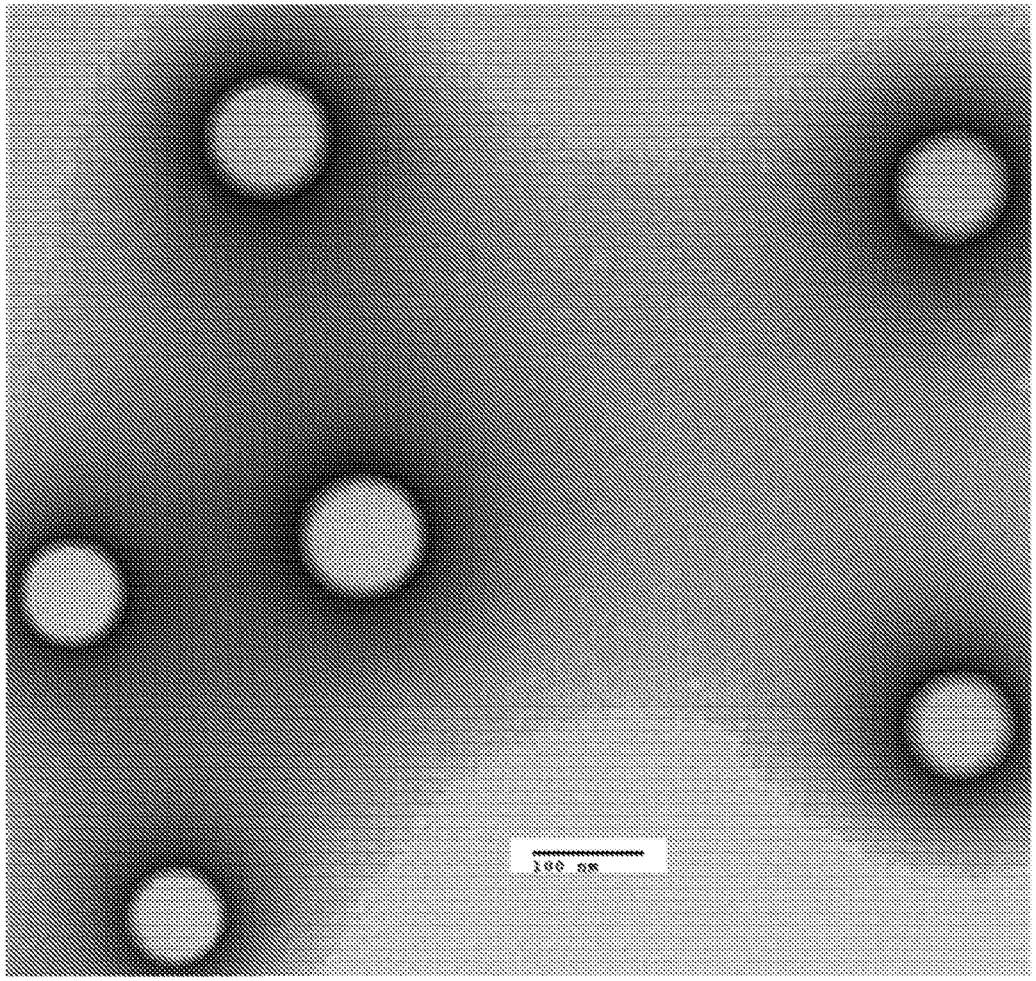
FIG. 18 is a TEM image of Ala-Arg-50 with 15% BSA loaded on surface and inside NP, respectively.

FIG. 18 shows TEM image of Ala-Arg-50 with 15% BSA loaded on surface and inside NP, respectively. NP size is around 100 nm.

REFERENCES 1. a) R. Katsarava, V. Beridze, N. Arabuli, D. Kharadze, C. C. Chu, C. Y. Won, Journal of Polymer Science Part A: Polymer Chemistry 1999, 37, 391-407; b) J. Wu, M. A. Mutschler, C.-C. Chu, Journal of Materials Science: Materials in Medicine 2011, 22, 469-479.
2. N. Kamaly, G. Fredman, M. Subramanian, S. Gadde, A. Pesic, L. Cheung, Z. A. Fayad, R. Langer, I. Tabas, O. C. Farokhzad, Proc Natl Acad Sci U S A 2013, 110, 6506-6511.
3. T. Akagi, K. Watanabe, H. Kim, M. Akashi, Langmuir 2010, 26, 2406-2413.
4. D. Dutta, J. G. Donaldson, Cell Logist 2012, 2, 203-208
5. F. Duchardt, M. Fotin-Mleczek, H. Schwarz, R. Fischer, R. Brock, Traffic 2007, 8, 848-866
6. H. T. McMahon, E. Boucrot, Nat Rev Mol Cell Biol 2011, 12, 517-533.
7. S. Arora, S. K. Ojha, D. Vohora, Global J. Pharmacol. 2009, 3, 81-84.
8. J. Zhang, X. Zhu, Y. Jin, W. Shan, Y. Huang, Mol Pharm 2014, 11, 1520-1532.
9. E. M. Pridgen, F. Alexis, T. T. Kuo, E. Levy-Nissenbaum, R. Karnik, R. S. Blumberg, R. Langer, O. C. Farokhzad, Sci. Transl. Med. 2013, 5, 213ra167.
10. B. Leader, Q. J. Baca, D. E. Golan, Nat. Rev. Drug Discov. 2008, 7, 21-39.
11. T. Vermonden, R. Censi, W. E. Hennink, Chem. Rev. 2012, 112, 2853-2888.
12. R. Mo, T. Jiang, J. Di, W. Tai, Z. Gu, Chem. Soc. Rev. 2014, 43, 3595-3629.
13. E. M. Pridgen, F. Alexis, O. C. Farokhzad, Clin Gastroenterol Hepatol 2014, 12, 1605-1610.
14. E. M. Pridgen, F. Alexis, T. T. Kuo, E. Levy-Nissenbaum, R. Karnik, R. S. Blumberg, R. Langer, O. C. Farokhzad, Sci. Transl. Med. 2013, 5, 213ra167.
15. S. Frokjaer, D. E. Otzen, Nat. Rev. Drug Discov. 2005, 4, 298-306.
16. J. Wu, N. Kamaly, J. Shi, L. Zhao, Z. Xiao, G. Hollett, R. John, S. Ray, X. Xu, X. Zhang, P. W. Kantoff, O. C. Farokhzad, Angew. Chem. Int. Ed. 2014, 53, 8975-8979.
17. a) D. T. Wiley, P. Webster, A. Gale, M. E. Davis, Proc Natl Acad Sci U S A 2013, 110, 8662-8667; b) Z. B. Zhu, S. K. Makhija, B. Lu, M. Wang, A. A. Rivera, M. Preuss, F. Zhou, G. P. Siegal, R. D. Alvarez, D. T. Curiel, Virology 2004, 325, 116-128; c) H. Kawabata, R. Yang, T. Hirama, P. T. Vuong, S. Kawano, A. F. Gombart, H. P. Koeffler, J Biol Chem 1999, 274, 20826-20832.
18. J. Wu, C.-C. Chu, J. Mater. Chem. B 2013, 1, 353-360.
19. B. Leader et al., Nature Reviews 2008, 7, 21-39.
20. G. Stewart, Clinical Reviews in Allergy and Immunology 1995, 13, 135-150.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A nanoparticle comprising
a core comprising a poly(ester amide) polymer comprising a repeating unit of Formula (Ia):

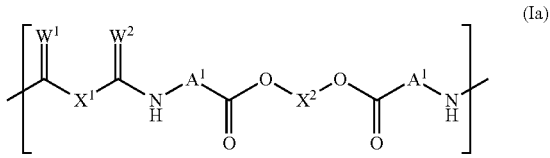

and a repeating unit of Formula (Ib):

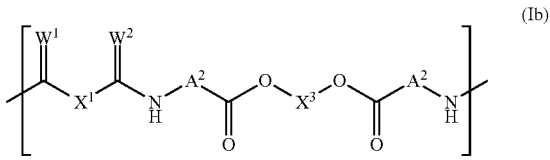

wherein:

each $X^1$ is $C_{1-100}$ alkylene, $C_{2-100}$ alkenylene, or $C_{2-100}$ alkynylene, each of which is optionally substituted with 1, 2, or 3 substituents independently selected from the group consisting of: halo, —CN, $R^1$, $OR^1$, $NR^1R^2$, —(C=O)$R^2$, —(C=O)$OR^2$, —(C=O)$NR^1R^2$, and —S(O)$_m R^2$;

$X^2$ is $C_{1-100}$ alkylene, $C_{2-100}$ alkenylene, or $C_{2-100}$ alkynylene, each of which is optionally substituted with 1, 2, or 3 substituents independently selected from the group consisting of: halo, —CN, $R^1$, $OR^1$, $NR^1R^2$, —(C=O)$R^2$, —(C=O)$OR^2$, —(C=O)$NR^1R^2$, and —S(O)$_m R^2$;

$X^3$ is $C_{1-100}$ alkylene, $C_{2-100}$ alkenylene, or $C_{2-100}$ alkynylene, each of which is optionally substituted with 1, 2, or 3 substituents independently selected from the group consisting of: halo, —CN, $R^1$, $OR^1$, $NR^1R^2$, —(C=O)$R^2$, —(C=O)$OR^2$, —(C=O)$NR^1R^2$, and —S(O)$_m R^2$;

each $R^1$ is H, $C_{1-6}$ alkyl, $C_{2-6}$ alkenyl, $C_{2-6}$ alkynyl, $C_{3-10}$ cycloalkyl, $C_{6-10}$ aryl, 5-10-membered heteroaryl, or 4-10-membered heterocycloalkyl, each of which is optionally substituted with 1, 2, or 3 substituents independently selected from the group consisting of OH, $NO_2$, CN, halo, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thiol, $C_{1-6}$ alkylthio, $C_{1-6}$ alkylsulfinyl, $C_{1-6}$ alkyl sulfonyl, carboxy, $C_{1-6}$ alkylcarbonyl, and $C_{1-6}$ alkoxycarbonyl;

each $R^2$ is H, $C_{1-6}$ alkyl, $C_{2-6}$ alkenyl, $C_{2-6}$ alkynyl, $C_{3-10}$ cycloalkyl, $C_{6-10}$ aryl, 5-10-membered heteroaryl, or 4-10-membered heterocycloalkyl, each of which is optionally substituted with 1, 2, or 3 substituents independently selected from the group consisting of OH, $NO_2$, CN, halo, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thiol, $C_{1-6}$ alkylthio, $C_{1-6}$ alkylsulfinyl, $C_{1-6}$ alkyl sulfonyl, carboxy, $C_{1-6}$ alkylcarbonyl, and $C_{1-6}$ alkoxycarbonyl;

each m is 0, 1 or 2;

each $W^1$ is O, S, or NH;

each $W^2$ is O, S, or NH;

each $A^1$ is a hydrophobic aminoacid residue; and each $A^2$ is a cationic aminoacid residue;

a payload molecule within the core; and a surface layer comprising a targeting ligand that binds or reacts selectively with a receptor on the outside surface of a cell.

2. The nanoparticle of claim 1, wherein the repeating unit of Formula (Ia) has Formula (IIa)

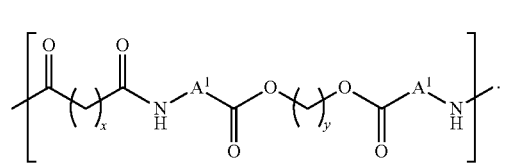

and the repeating unit of Formula (Ib) has Formula (IIb):

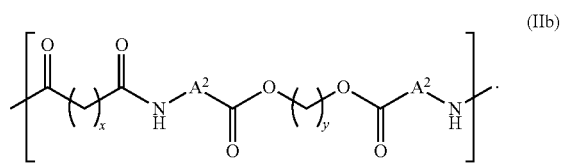

3. The nanoparticle of claim 2, wherein x is an integer from 2 to 10 and y is an integer from 2 to 8.

4. The nanoparticle of claim 1, wherein $A^1$ is selected from the group of the following Formulae:

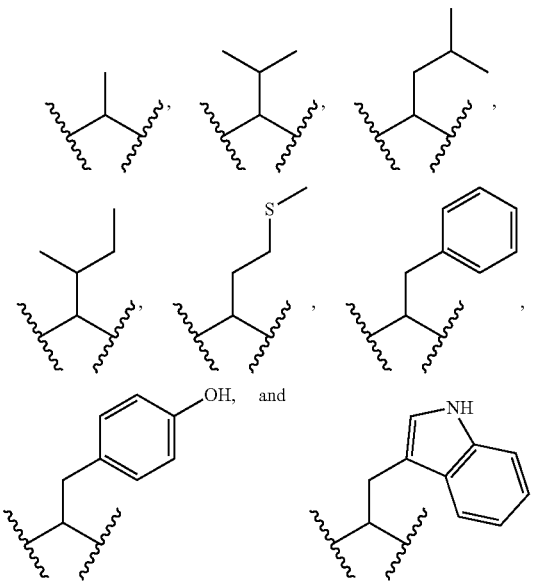

5. The nanoparticle of claim 1, wherein $A^2$ is selected from the group of the following Formulae:

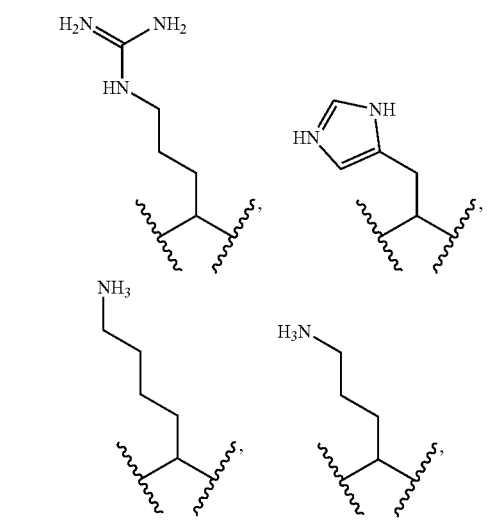

-continued

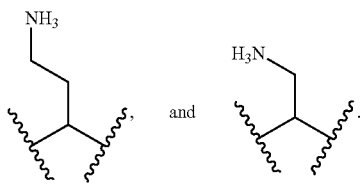

6. The nanoparticle of claim 1, wherein the repeating unit of Formula (Ia) has Formula (IIa) or Formula (IIId):

(IIIa)

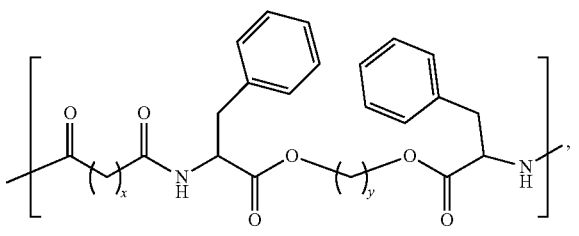

(IIId)

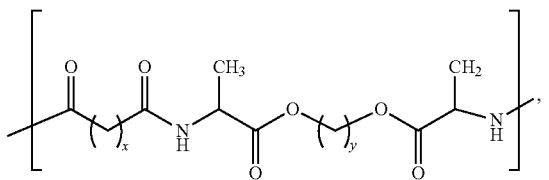

wherein x is 4, 6 or 8 and y is 6, and the repeating unit of Formula (Ib) has Formula (IIIb):

(IIIb)

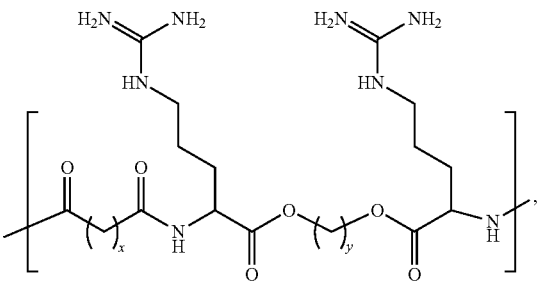

wherein x is 4, 6 or 8 and y is 6.

7. The nanoparticle of claim 1, wherein the payload molecule is selected from a therapeutic protein, a chemotherapeutic agent, and an antigen.

8. The nanoparticle of claim 1, wherein the targeting ligand that binds or reacts selectively with a receptor on the outside surface of a cell further promotes transcytosis or endocytosis of the particle.

9. A method of preparing a nanoparticle of claim 1, the method comprising:
   obtaining a first solution of the poly(ester amide) polymer comprising a repeating unit of Formula (Ia) and a repeating unit of Formula (Ib) as recited in claim 1 in a water-miscible solvent;
   obtaining a second aqueous solution comprising the targeting ligand that binds or reacts selectively with a receptor on the outside surface of a cell; and
   mixing the first solution with the second aqueous solution to form an aqueous suspension comprising the nanoparticle of claim 1.

10. A composition comprising the nanoparticle of claim 1 and a pharmaceutically acceptable carrier.

\* \* \* \* \*

UNITED STATES PATENT AND TRADEMARK OFFICE
CERTIFICATE OF CORRECTION

PATENT NO. : 11,123,304 B2
APPLICATION NO. : 16/483170
DATED : September 21, 2021
INVENTOR(S) : Farokhzad et al.

Page 1 of 1

It is certified that error appears in the above-identified patent and that said Letters Patent is hereby corrected as shown below:

On the Title Page

On page 2, Column 1 under item (57) (Abstract), Line 2, delete

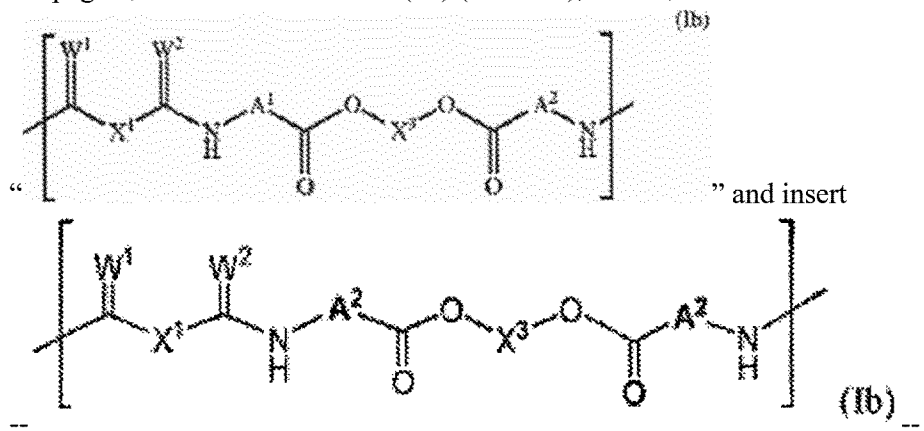

" and insert

In the Claims

In Column 67, Lines 60-65 (approx.), in Claim 2, delete

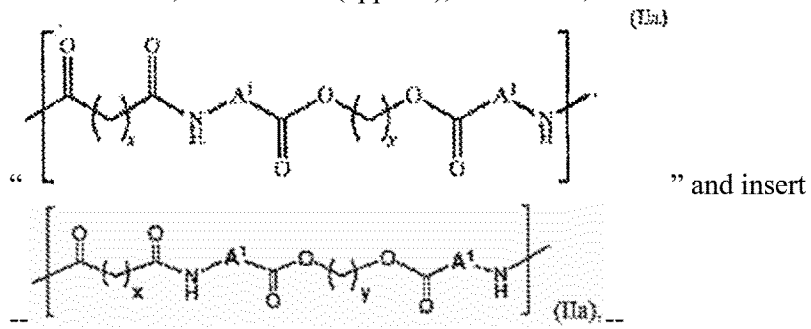

" and insert

Signed and Sealed this
Twenty-first Day of June, 2022

Katherine Kelly Vidal
Director of the United States Patent and Trademark Office

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Ova257-264

<400> SEQUENCE: 1

Ser Ile Ile Asn Phe Glu Lys Leu
1               5
```